(12) United States Patent
Taniguchi et al.

(10) Patent No.: US 9,498,189 B2
(45) Date of Patent: Nov. 22, 2016

(54) ULTRASOUND DIAGNOSTIC IMAGING APPARATUS AND ULTRASOUND DIAGNOSTIC IMAGING METHOD

(71) Applicant: KONICA MINOLTA, INC., Tokyo (JP)

(72) Inventors: Tetsuya Taniguchi, Hachioji (JP); Kenji Suzuki, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 586 days.

(21) Appl. No.: 13/959,411

(22) Filed: Aug. 5, 2013

(65) Prior Publication Data

US 2014/0046187 A1 Feb. 13, 2014

(30) Foreign Application Priority Data

Aug. 10, 2012 (JP) ................... 2012-178125

(51) Int. Cl.
*A61B 8/14* (2006.01)
*A61B 8/08* (2006.01)
(Continued)

(52) U.S. Cl.
CPC ........... *A61B 8/5269* (2013.01); *A61B 8/4461* (2013.01); *A61B 8/463* (2013.01); *A61B 8/5253* (2013.01); *G01S 15/8995* (2013.01); *A61B 8/4405* (2013.01)

(58) Field of Classification Search
CPC .. A61B 8/4405; A61B 8/4461; A61B 8/463; A61B 8/5253; A61B 8/5269; G01S 15/8995
See application file for complete search history.

(56) References Cited

U.S. PATENT DOCUMENTS

| | | | |
|---|---|---|---|
| 6,210,328 B1 | 4/2001 | Robinson et al. |
| 6,579,238 B1 | 6/2003 | Simopoulos et al. |
| 2001/0014773 A1 | 8/2001 | Jago |

(Continued)

FOREIGN PATENT DOCUMENTS

| | | | |
|---|---|---|---|
| JP | 2004500915 A | 1/2004 |
| JP | 2004522515 A | 7/2004 |

(Continued)

OTHER PUBLICATIONS

Japanese Office Action (and English translation thereof) dated Dec. 22, 2015, issued in counterpart Japanese Application No. 2012-178125.

*Primary Examiner* — Mark Remaly
(74) *Attorney, Agent, or Firm* — Holtz, Holtz & Volek PC

(57) ABSTRACT

Described is an ultrasound diagnostic imaging apparatus which includes an ultrasound probe and which generates ultrasound image data sets for displaying an ultrasound image. The ultrasound diagnostic imaging apparatus includes a transmitting unit which performs ultrasound scanning for a plurality of times so that a part of or all of scan regions overlap in a plurality of different directions, an image processing unit which generates a plurality of ultrasound image data sets according to the receive signals and an anisotropic aspect evaluation unit which evaluates an anisotropic aspect of ultrasound wave reflection in the subject according to at least either of the ultrasound image data sets and the receive signals. In the ultrasound diagnostic imaging apparatus, the image processing unit generates synthetic image data in which the plurality of ultrasound image data sets are synthesized according to an evaluation result of the anisotropic aspect evaluation unit.

20 Claims, 35 Drawing Sheets

(51) Int. Cl.
 *G01S 15/89* (2006.01)
 *A61B 8/00* (2006.01)

(56) References Cited

U.S. PATENT DOCUMENTS

2003/0097069 A1* 5/2003 Avinash .............. G06T 5/002
 600/447
2010/0160783 A1 6/2010 Halmann et al.
2011/0015524 A1 1/2011 Suzuki et al.
2011/0118599 A1 5/2011 Osumi
2012/0157850 A1 6/2012 Sumi et al.

FOREIGN PATENT DOCUMENTS

| JP | 2005125082 A | 5/2005 |
| JP | 2011-078792 A | 4/2011 |
| JP | 2011-125690 A | 6/2011 |
| JP | 2012071115 A | 4/2012 |
| WO | 2009118798 A1 | 10/2009 |

* cited by examiner

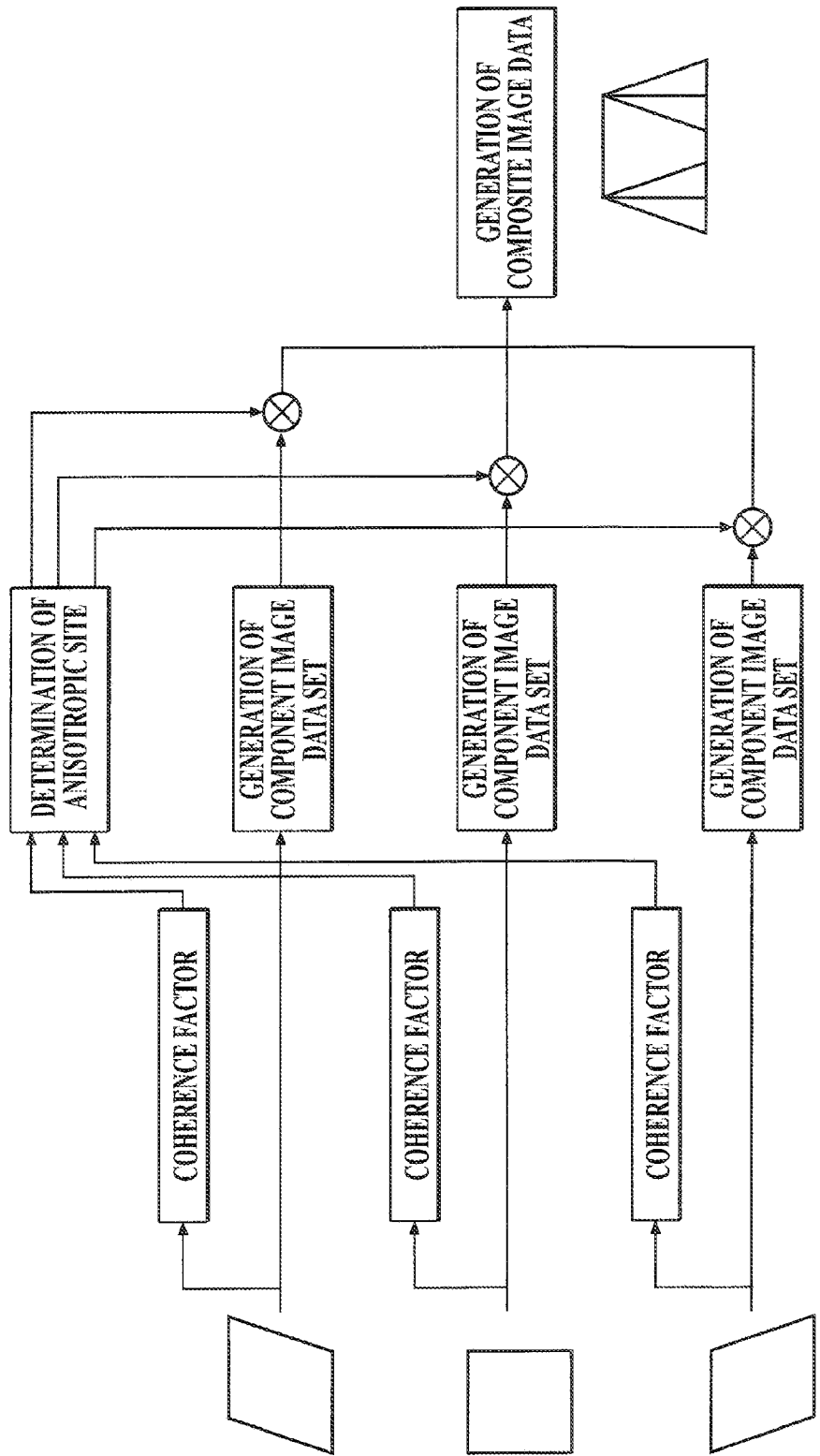

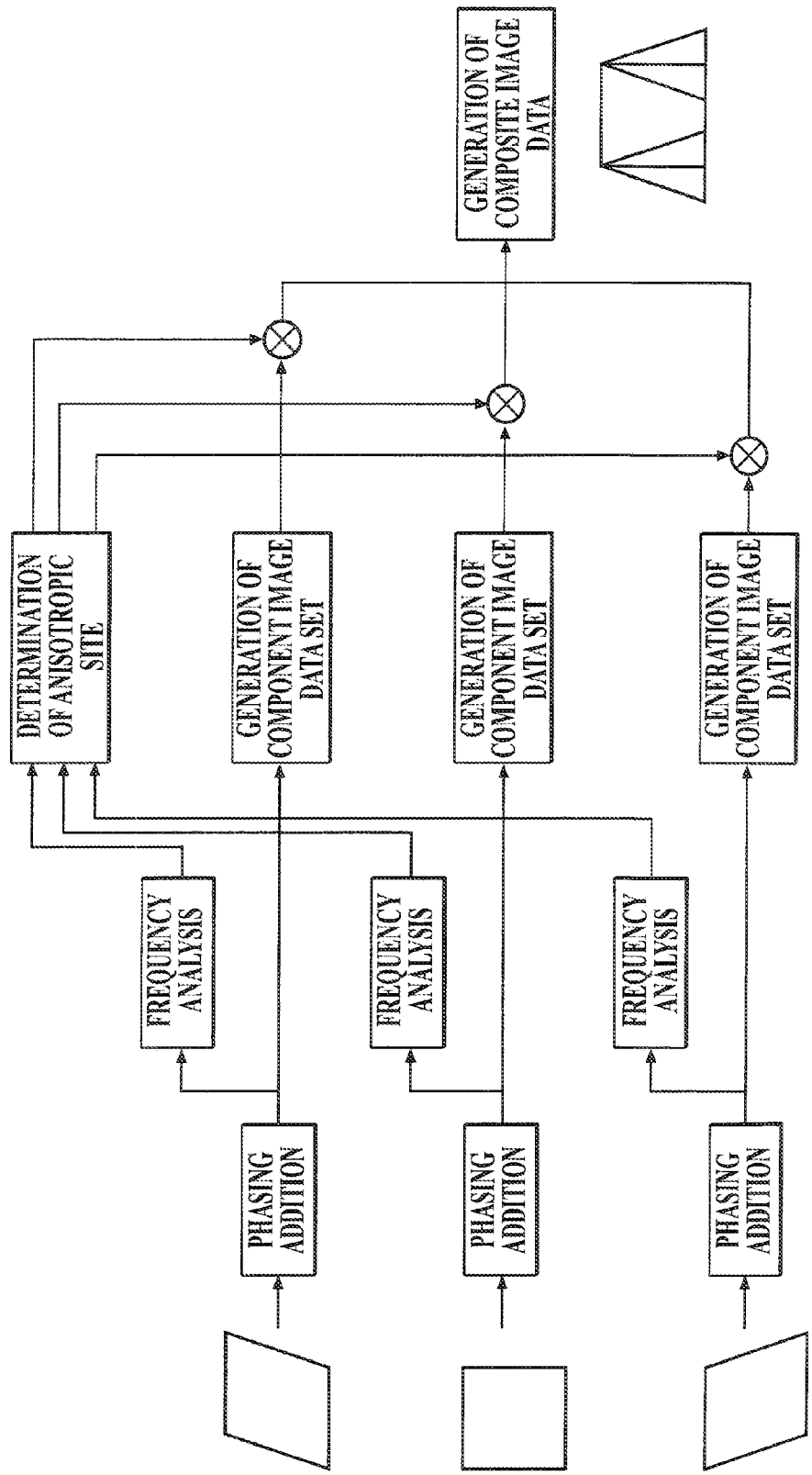

ULTRASOUND DIAGNOSTIC IMAGING APPARATUS AND ULTRASOUND DIAGNOSTIC IMAGING METHOD

BACKGROUND OF THE INVENTION

1. Field of the Invention

The present invention relates to an ultrasound diagnostic imaging apparatus and an ultrasound diagnostic imaging method.

2. Description of Related Art

Conventionally, ultrasound diagnostic imaging apparatuses including ultrasound probes with a plurality of transducers aligned therein are known. Such ultrasound diagnostic imaging apparatuses perform transmission and reception of ultrasound waves with respect to a subject such as a living body, generate ultrasound image data according to signals obtained from the received ultrasound waves and display ultrasound images in the image display apparatuses based on the generated ultrasound image data. Ultrasound diagnosis using such apparatuses can be repeatedly performed because real time subject conditions such as heart beat and fetus movement can be obtained with simple operation by touching the body surface of a subject with an ultrasound probe and such operation is noninvasive and safe.

However, images obtained by these ultrasound diagnostic imaging apparatuses includes various noises and speckles that occur due to interference of the receive signals obtained from the ultrasound waves in addition to information relating to tissues in subjects. These noises and speckles become obstacles for correctly grasping the position and shapes at the borders of tissues in subjects.

In recent years, as a processing method for reducing the noises and speckles, for example, a spatial compounding method is suggested in JP 2011-78792 and JP 2011-125690. In the spatial compounding method, transmitting and receiving of ultrasound waves are performed in a plurality of different directions at the same time with respect to the same part in a subject and average weighting is performed with respect to the obtained plurality of ultrasound image data sets. In such way, for example, in a case where N sheets of ultrasound image data sets are obtained, noises and speckles are reduced by the square root of N in the synthetic image formed by the N sheets of ultrasound image data sets being synthesized.

Moreover, according to the spatial compounding method, visibility of specular interfaces can be improved. That is, for example, with respect to a curved interface between a soft tissue and a bone, a strong reflection ultrasound waves can be obtained when the direction of the ultrasound beam formed of the transmission ultrasound waves is strictly at a right angle. However, the intensity of the reflection ultrasound waves can be greatly reduced just by the direction of the ultrasound beam shifting by few degrees from the right angle with respect to the interface. Often times, the interfaces between soft tissues and bones are curved, and therefore, only parts of such curved interfaces can be visualized clearly when ultrasound scanning is performed only in one direction as in the conventional methods. However, according to the spatial compounding method, interface images can be obtained from a plurality of different angles and curved interfaces can be visualized continuously for a greater view.

SUMMARY OF THE INVENTION

The conventional spatial compounding method is useful to some extent with respect to interfaces and tissues having specular reflection characteristics such as the interfaces between soft tissues and bones and having great reflection intensity. However, the conventional spatial compounding method is not satisfactory for visualizing anisotropic sites in soft tissues showing specular reflection characteristics but the reflection intensity not being as intensive as bone surfaces due to their fibrous structure, such as tendons and ligaments in skeletal muscles.

Visualization of anisotropic sites in soft tissues is very important for accurately determining raptures, damages and sprain fractures in observation of an anterior talofibular ligament and such like in the area of orthopedics. Thus, improvements are needed.

The present invention is made in view of the above problems and an object of the present invention is to provide an ultrasound diagnostic imaging apparatus and an ultrasound diagnostic imaging method which can clearly visualize an anisotropic site.

In order to realize the above object, an ultrasound diagnostic imaging apparatus reflecting one aspect of the present invention is an ultrasound diagnostic imaging apparatus which includes an ultrasound probe which obtains receive signals by driving a plurality of transducers and performing transmission and reception of ultrasound waves to and from a subject and which generates ultrasound image data sets for displaying an ultrasound image wherein the receive signals are converted into luminescence in the ultrasound image data, and the ultrasound diagnostic imaging apparatus includes a transmitting unit which performs ultrasound scanning for a plurality of times so that a part of or all of scan regions overlap by driving the plurality of transducers and performing the transmission and reception of the ultrasound waves in a plurality of directions, the directions being different from each other, an image processing unit which generates a plurality of ultrasound image data sets according to the receive signals obtained as a result of the transmitting unit performing the ultrasound scanning, and an anisotropic aspect evaluation unit which evaluates an anisotropic aspect of ultrasound wave reflection in the subject according to at least either of the ultrasound image data sets and the receive signals, and the image processing unit generates synthetic image data in which the plurality of ultrasound image data sets are synthesized according to an evaluation result of the anisotropic aspect evaluation unit.

Preferably, the image processing unit synthesizes the plurality of ultrasound image data sets by a synthesis method according to the evaluation result of the anisotropic aspect evaluation unit.

Preferably, the anisotropic aspect evaluation unit detects an anisotropic site showing the anisotropic aspect of ultrasound wave reflection, and the image processing unit applies different synthesis methods for a part where the anisotropic site is detected by the anisotropic aspect evaluation unit and a part other than the part where the anisotropic site is detected when generating the synthetic image data.

Preferably, a depth rate of a receive focal point with respect to an aperture formed of the transducers of the receive signals which are to be used for performing phasing addition is set to 0.8 or smaller.

Preferably, if a depth rate of a receive focal point with respect to an aperture formed of the transducers of the receive signals which are to be used for performing phasing addition is set to a receive F value and a depth rate of a transmission focal point with respect to an aperture formed of the transducers for transmitting the ultrasound waves is set to a transmission F value, a rate of the transmission F value with respect to the receive F value is set to 3 or greater.

Preferably, the transmitting unit sets a transmission/reception condition for performing the transmission and reception of the ultrasound waves according to the evaluation result of the anisotropic aspect evaluation unit and performs the ultrasound scanning under the set transmission/reception condition, and the image processing unit generates the synthetic image data in which a plurality of ultrasound image data sets generated from receive signals obtained as a result of performing the ultrasound scanning under the set transmission/reception condition.

Preferably, the transmitting unit sets a direction in which the transmission and reception of the ultrasound waves are to be performed as the transmission/reception condition to be set according to the evaluation result of the anisotropic aspect evaluation unit.

Preferably, the transmitting unit sets the number of scan regions in which the ultrasound scanning is to be performed as the transmission/reception condition to be set according to the evaluation result of the anisotropic aspect evaluation unit.

Preferably, the transmitting unit sets the transducers of the receive signals to be used to performing phase addition as the transmission/reception condition to be set according to the evaluation result of the anisotropic aspect evaluation unit.

Preferably, a depth rate of a receive focal point with respect to an aperture formed of the transducers of the receive signals to be used for performing phasing addition is set to 0.8 or smaller after the transmission/reception condition is set.

Preferably, if a depth rate of a receive focal point with respect to an aperture formed of the transducers for the receive signals which are to be used for performing phasing addition is set to a receive F value and a depth rate of a transmission focal point with respect to an aperture formed of the transducers for transmitting the ultrasound waves is set to a transmission F value, a rate of the transmission F value with respect to the receive F value is set to 3 or greater after the transmission/reception condition is set.

Preferably, the anisotropic aspect evaluation unit calculate a luminescence difference at an overlapping part in the scan regions of two ultrasound image data sets among the plurality of ultrasound image data sets and evaluates an anisotropic aspect of a part where the calculated luminescence difference is equal to a predetermined threshold or greater.

Preferably, the anisotropic aspect evaluation unit calculates a coherence factor, which is a rate of a coherence sum with respect to an incoherence sum, based on the receive signals respectively obtained by the transducers, the receive signals being obtained by the plurality of transducers and not yet subjected to phase addition.

Preferably, the anisotropic aspect evaluation unit performs anisotropic aspect evaluation by detecting that a specific frequency component is continuously included the receive signals.

Preferably, the anisotropic aspect evaluation unit performs anisotropic aspect evaluation by detecting that a predetermined waveform pattern is included in waveforms of the receive signals on which envelope detection is performed.

Preferably, the anisotropic aspect evaluation unit calculates a luminescence difference at an overlapping part in the scan regions of two ultrasound image data sets among the plurality of ultrasound image data sets and performs anisotropic aspect evaluation based on a size of the calculated luminescence difference.

Preferably, the anisotropic aspect evaluation unit performs spatial frequency analysis with respect to the ultrasound image data sets and performs anisotropic aspect evaluation based on results of the spatial frequency analysis.

Preferably, the anisotropic aspect evaluation unit performs anisotropic aspect evaluation by detecting that a predetermined anisotropic site image pattern is included in the ultrasound image data sets.

Preferably, the anisotropic aspect evaluation unit performs edge detection with respect to the ultrasound image data sets and performs anisotropic aspect evaluation based on a fact that an edge of a predetermined length are extracted continuously as a result of the edge detection.

Preferably, the anisotropic aspect evaluation unit calculates a correlation coefficient of two ultrasound image data sets among the plurality of ultrasound image data sets by a predetermined correlation operation and performs anisotropic aspect evaluation based on the calculated correlation coefficient.

Preferably, the anisotropic aspect evaluation unit executes a plurality of types of evaluation methods for anisotropic aspect evaluation, and the image processing unit generates the synthetic image data according to an anisotropic aspect evaluation result on condition that the anisotropic aspect evaluation is performed by applying at least a predetermined number of types of evaluation methods among the plurality of types of evaluation methods.

Preferably, the transmitting unit sets a transmission/reception condition for performing the transmission and reception of the ultrasound waves according to an anisotropic aspect evaluation result of the anisotropic aspect evaluation unit and performs the ultrasound scanning under the set transmission/reception condition, and the image processing unit generates the synthetic image data by synthesizing a plurality of ultrasound image data sets generated from receive signals obtained as a result of performing the ultrasound scanning under the set transmission/reception condition by a synthesis method according to an anisotropic aspect evaluation result of the anisotropic aspect evaluation unit.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 14 is an explanatory diagram of a processing flow of the $1^{st}$ example of spatial compounding;

FIG. 15 is an explanatory diagram of a processing flow of the $2^{nd}$ example of spatial compounding;

DESCRIPTION OF THE PREFERRED EMBODIMENTS

Figure 1:
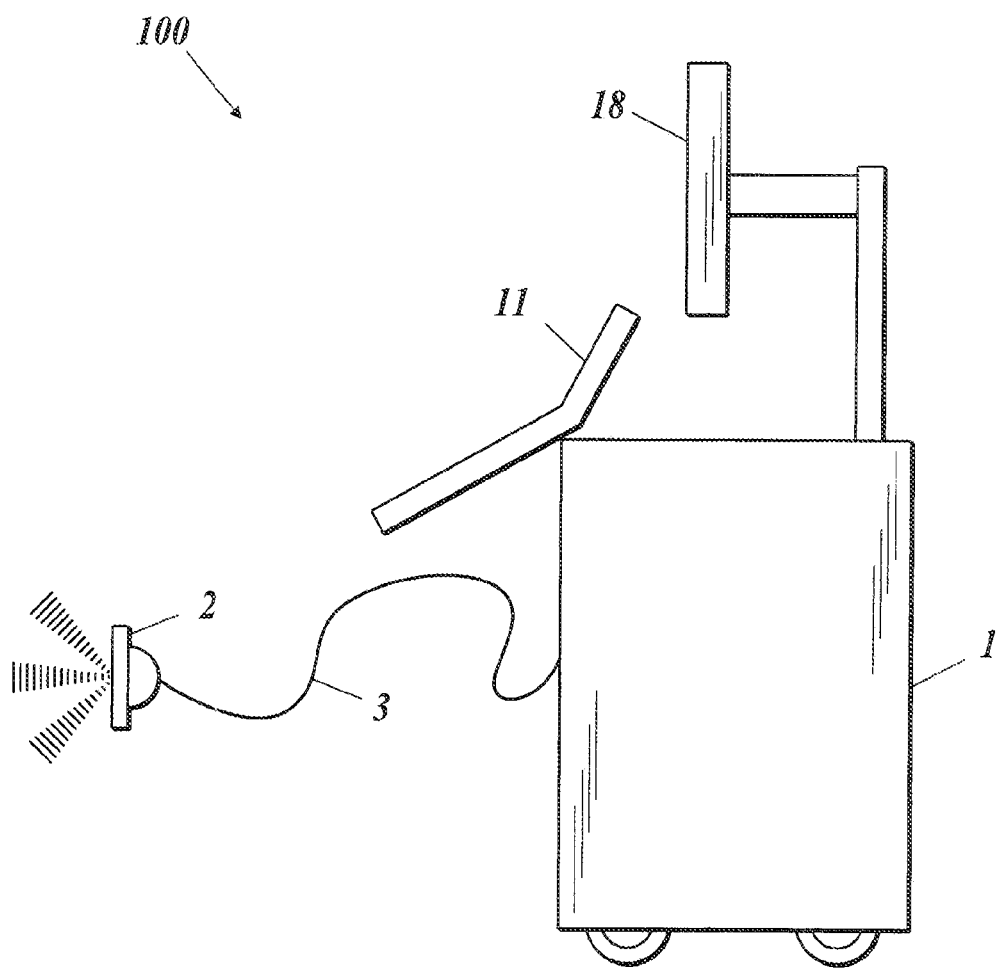
FIG. 1 is a diagram showing an outer configuration of an ultrasound diagnostic imaging apparatus.

Hereinafter, the ultrasound diagnostic imaging apparatus according to the embodiment will be described with reference to the drawings. The scope of the present invention is not limited to the examples shown in the drawings. In the following descriptions, like reference numerals are used for the like functions and configurations, and similar descriptions are omitted.

As shown in FIG. 1, the ultrasound diagnostic imaging apparatus 100 includes an ultrasound diagnostic imaging apparatus main body 1 and an ultrasound probe 2. The ultrasound probe 2 transmits ultrasound waves (transmission ultrasound waves) into a subject such as a living object (not shown) and also receives reflected waves that reflected off inside the subject (reflection ultrasound waves: echo). The ultrasound diagnostic imaging apparatus main body 1 is connected with the ultrasound probe 2 via a cable 3. By the ultrasound diagnostic imaging apparatus main body 1 transmitting driving signals which are electric signals to the ultrasound probe 2, the ultrasound probe 2 is made to transmit the transmission ultrasound waves to the subject. Further, the ultrasound diagnostic imaging apparatus main body 1 visualizes the inside condition of the subject as an ultrasound image based on the received signals which are electric signals that are generated in the ultrasound probe 2 according to the reflection ultrasound waves reflected off inside the subject and received by the ultrasound probe 2.

The ultrasound probe 2 includes transducers 2a formed of piezo-electric devices (see FIG. 2), and the plurality of transducers 2a are arranged in one dimensional array in an orientation direction (scanning direction), for example. In the embodiment, for example, an ultrasound probe 2 having 192 transducers 2a is used. Here, the transducers 2a may be arranged in two dimensional array. Further, the number of transducers 2a can be set arbitrarily. In the embodiment, a linear scanning type electronic scanning probe is used as the ultrasound probe 2 to perform ultrasound scanning of linear scanning method. However, either of a sector scanning type and a convex scanning type can also be used.

Figure 2:
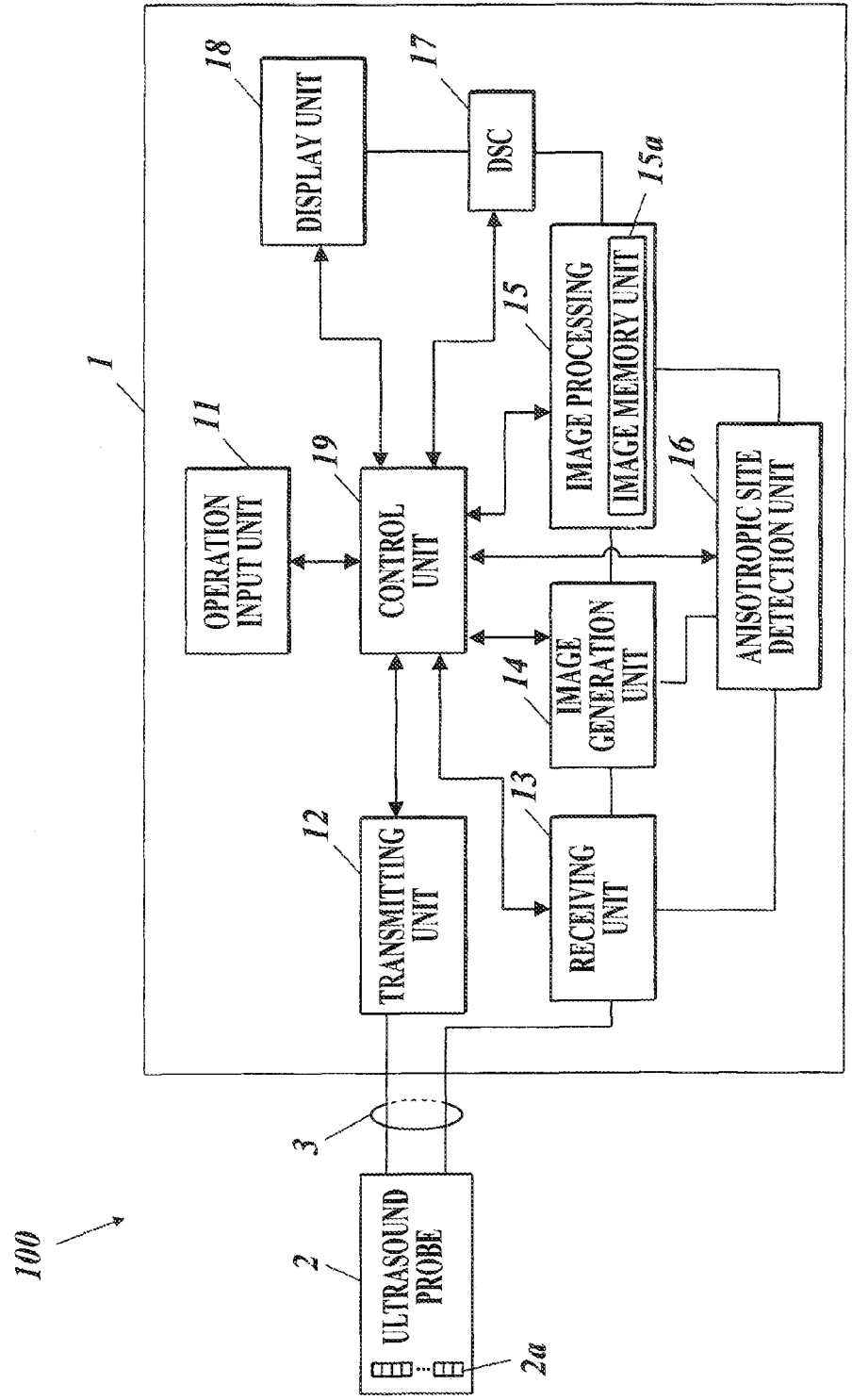
FIG. 2 is a block diagram showing a schematic configuration of the ultrasound diagnostic imaging apparatus.

As shown in FIG. 2, the ultrasound diagnostic imaging apparatus main body 1 includes an operation input unit 11, a transmitting unit 12, a receiving unit 13, an image generation unit 14, an image processing unit 15, an anisotropic site detection unit 16, a DSC (Digital Scan Converter) 17, a display unit 18 and a control unit 19, for example.

The operation input unit 11 includes various types of switches, buttons, a track-ball, a mouse, a key board and the like for inputting a command for instructing start of diagnosis, data such as personal information of a subject and various types of parameters for displaying an ultrasound image on the display unit 18, and the operation input unit 11 outputs operation signals to the control unit 19.

The transmitting unit 12 is a circuit to make the ultrasound probe 2 generate transmission ultrasound waves by supplying driving signals which are electronic signals to the ultrasound probe 2 via the cable 3 in compliance with the control of the control unit 19. For example, the transmitting unit 12 includes a clock generation circuit, a delay circuit and a pulse generating circuit. The clock generation circuit is a circuit for generating a clock signal which determines the transmission timing and a transmission frequency of a driving signal. The delay circuit is a circuit for setting a delay time for each of the individual paths corresponding to the transducers 2a, and for concentrating the transmission beam (transmission beam forming) formed of transmission ultrasound waves by delaying the transmission of the driving signal for the set delay time, and setting the angle of the transmission beam (steering). The pulse generating circuit is a circuit for generating pulse signals as driving signals at a predetermined cycle. The transmitting unit 12 which is configured as described above, for example, generates transmission ultrasound waves by driving a continuous part of (for example, 64) the plurality of transducers 2a (for example, 192) which are aligned in the ultrasound probe 2. Then, the transmitting unit 12 performs scanning by shifting the transducers 2a, which is to be driven, in the orientation direction every time transmission ultrasound waves are to be generated. Further, the transmitting unit 12 can perform ultrasound scanning in a plurality of scan regions of different angles by performing scanning while changing the angle of the transmission beam.

The receiving unit 13 is a circuit for receiving receive signals which are electric signals from the ultrasound probe 2 via the cable 3 in compliance with the control of the control unit 19. The receiving unit 13 is provided with an amplifier, an A/D conversion circuit and a phasing addition circuit, for example. The amplifier is a circuit for amplifying the receive signals at a preset amplification factor for each of the individual paths corresponding to the transducers 2a. The A/D conversion circuit is a circuit for performing analog/digital conversion (A/D conversion) of the amplified receive signals. The phasing addition circuit is a circuit for adjusting time phases of the receive signals to which A/D conversion is performed by applying the delay time to each of the individual paths corresponding to the transducers 2a and generating sound ray data by adding the adjusted receive signals (phase addition). In other words, the phasing addition circuit generates sound ray data by performing receiver beam forming with respect to the receive signals of the transducers 2a.

The image generation unit 14 can generate B-mode image data by performing envelope detection, logarithmic compression and the like on the sound ray data from the receiving unit 13 and performing luminance conversion by adjusting the dynamic range and gain. In other words, B-mode image data is data where intensity of receive signals is expressed in luminance.

In the embodiment, the image generation unit 14 may generate A-mode image data, M-mode image data or image data of Doppler method other than B-mode image data.

The image processing unit 15 includes an image memory unit 15a constituted of a semiconductor memory such as a DRAM (Dynamic Random Access Memory). The image processing unit 15 stores B-mode image data output from the image generation unit 14 in the image memory unit 15a in frame units. The image data in frame units may be called ultrasound image data or frame image data. In the embodiment, ultrasound image data sets are generated respectively for the plurality of scan regions of different angles and the generated ultrasound image data sets are stored in the image memory 15a in the manner as described above. The ultrasound image data set of each scan region may be called a component image data set. In the component image data sets of the plurality of scan regions, the scan regions overlap partially or entirely. The image processing unit 15 can perform the spatial compounding by which synthetic image data is obtained by synthesizing overlapped scan region parts in the plurality of the obtained component image data sets. According to the synthetic image data obtained by the spatial compounding, various noises which occur during the process of transmission and receiving of ultrasound waves and speckles due to interference of the receive signals can be reduced. The image processing unit 15 outputs the synthetic image data generated as described above to the DSC 17.

The anisotropic site detection unit 16 evaluates the anisotropic aspect of the ultrasound wave reflection in a subject on the basis of receive signals, sound ray data and ultrasound image data sets and detects the anisotropic site in the subject. That is, the anisotropic site detection unit 16 functions as an anisotropic aspect evaluating unit. Anisotropic site is a site in soft tissue that shows a specular reflection characteristic although the reflection intensity is not as intense as a bone surface due to being fibrous, such as tendons and ligaments in skeletal muscles in a subject. If the anisotropic site detection unit 16 detects an anisotropic site in a subject, this detection result is given to the control unit 19. Functions of the anisotropic site detection unit 16 will be described in detail later.

The DSC 17 converts the synthetic image data received by the image processing unit 15 into an image signal of television signal scan mode and outputs the image signal to the display unit 18.

As for the display unit 18, display apparatuses such as a LCD (Liquid Crystal Display), a CRT (Cathode-Ray Tube) display, an organic EL (Electronic Luminescence) display, an inorganic EL display or a plasma display can be applied. The display unit 18 displays an ultrasound image on the display screen according to the image signal output from the DSC 17. Here, in the embodiment, a 15 inch LCD equipped with a white color or a full-color LED (Light-Emitting Diode) backlight is used. In this case, for example, the configuration may be such that the ultrasound image data can be analyzed to adjust the luminescence of the LED. One screen may be divided into a plurality of regions and the luminescence adjustment can be performed on each of the regions. Alternatively, the luminescence adjustment of the LED can be performed for the screen as a whole. The screen size to be applied to the display unit 18 can be arbitrarily set.

The control unit 19 includes a CPU (Central Processing Unit), a ROM (Read Only Memory) and a RAM (Random Access Memory), for example. The control unit 19 reads out and opens various types of programs such as a system program stored in the ROM in the RAM and collectively controls the operations of the components in the ultrasound diagnostic imaging apparatus 100 in compliance with the opened programs.

The ROM is configured of a non-volatile memory such as a semiconductor or the like, and stores a system program corresponding to the ultrasound diagnostic imaging apparatus 100, various types of processing programs which can be executed on the system program and various types of data such as a gamma table and the like. These programs are stored in the forms of program codes which can be read by a computer and the CPU sequentially executes the operations according to the program codes.

The RAM forms a work area in which various types of programs to be executed by the CPU and data relating to these programs are to be stored temporarily.

Next, the synthetic image data which is to be generated by the ultrasound diagnostic imaging apparatus 100, configured as described above, performing the spatial compounding will be described.

Figure 3:
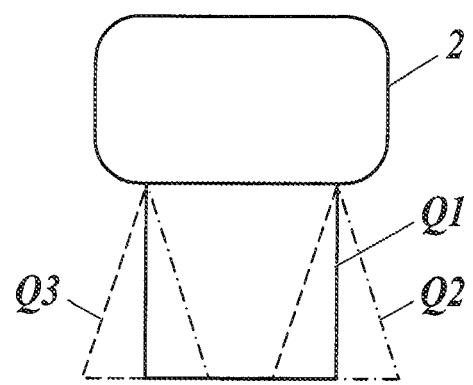
FIG. 3 is an explanatory diagram of scan regions to be scanned by ultrasound waves.

In conventional spatial compounding, as shown in FIG. 3, a component image data set of the scan region. Q1 is obtained by performing scanning by shifting the angle of the transmission beam output from the ultrasound probe 2 in the perpendicular direction with respect to the orientation direction (steering angle 0°) and also a component image data set of the scan region Q2 and a component image data set of the scan region Q3 are obtained by performing scanning by shifting the steering angle in the right and left for a predetermined angle (for example, 10°). At least a part in each of the scan regions Q1 to Q3 is overlapped with one another. Then, the component image data sets of the scan regions Q1 to Q3 are synthesized at the same rate to obtain synthetic image data. In such way, a good quality ultrasound image with reduced noise and speckles can be obtained.

The above mentioned anisotropic site has a strong directionality in its reflectance property. Therefore, if the anisotropic site is at a position not directly facing the transmission direction of the transmission beam, the reflection ultrasound waves which reflected off this anisotropic site are to be out of the receiving range of the ultrasound probe 2. As a result, an ultrasound image in which the anisotropic site is missing is to be obtained.

Figure 4A:
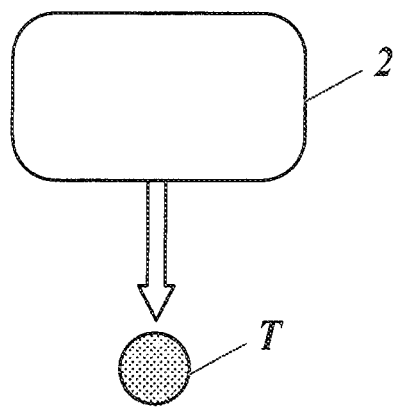
FIG. 4A is an explanatory diagram of a reflectance property of ultrasound waves.
Figure 4B:
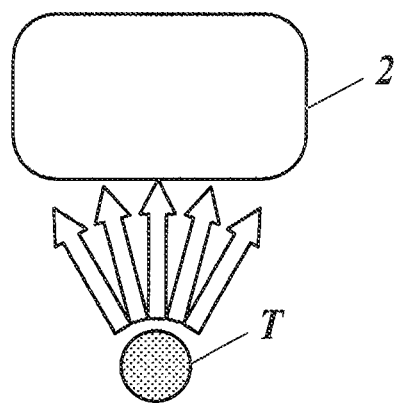
FIG. 4B is an explanatory diagram of a reflectance property of ultrasound waves.
Figure 5A:
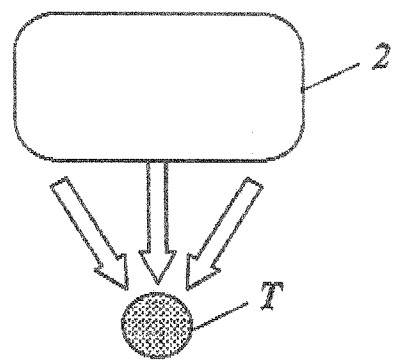
FIG. 5A is an explanatory diagram of a reflectance property of ultrasound waves.
Figure 5B:
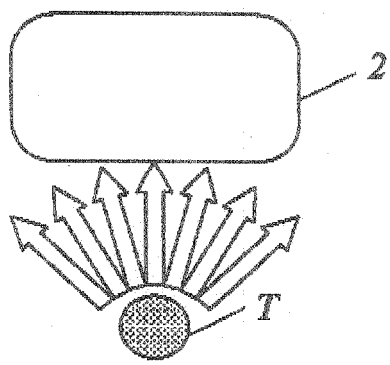
FIG. 5B is an explanatory diagram of a reflectance property of ultrasound waves.

In particular, for example, if ultrasound waves are transmitted to the body tissues where majority of them show no directionality as shown in FIG. 4A, the ultrasound waves reflect scattering in isotropic manner as shown in FIG. 4B. Therefore, most of the reflected ultrasound waves reflected off the body tissue T can be received by the ultrasound probe 2 and an ultrasound image in which the body tissue T is not missing can be obtained. Also, if the spatial compounding is to be performed by scanning a plurality of scan regions having different angles as shown in FIG. 5A, most of the reflection ultrasound waves reflected off the body tissue T are to be received by the ultrasound probe 2 as shown in FIG. 5B. Therefore, a good quality ultrasound image with reduced noises and speckles wherein the body tissue T is clearly shown can be obtained.

Figure 6A:
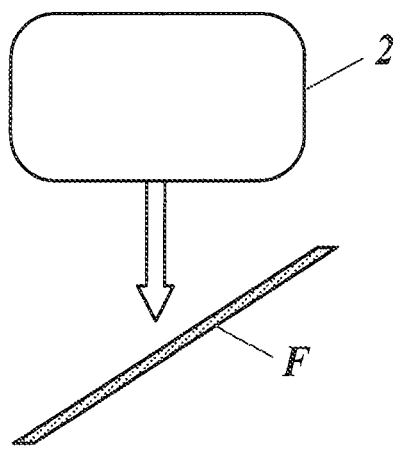
FIG. 6A is an explanatory diagram of a reflectance property of ultrasound waves.
Figure 6B:
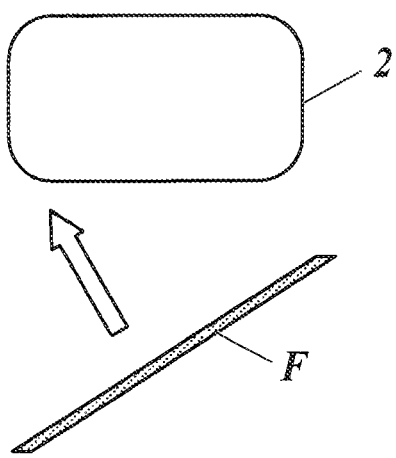
FIG. 6B is an explanatory diagram of a reflectance property of ultrasound waves.
Figure 7:
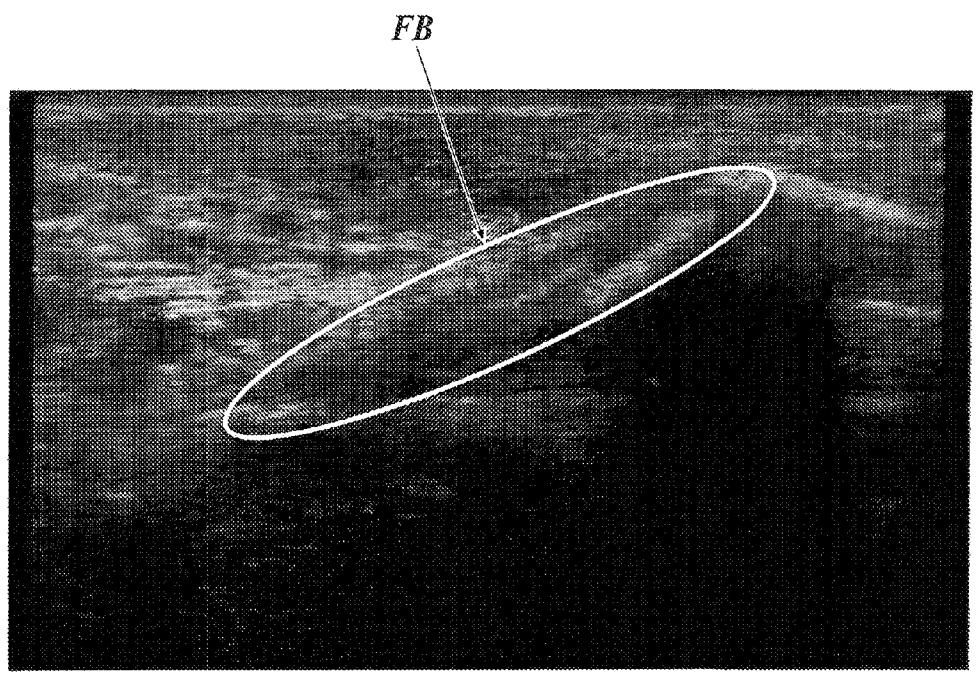
FIG. 7 is an explanatory diagram of an ultrasound image showing an anterior talofibular ligament and its surrounding.

On the other hand, if ultrasound waves are transmitted to the anisotropic site F which is a fibrous tissue such as a ligament or a tendon as shown in FIG. 6A, the ultrasound waves reflects with a constant directionality as shown in FIG. 6B. Therefore, most of the reflection ultrasound waves which reflected off the anisotropic site F are not received by the ultrasound probe 2, and an ultrasound image with bad visibility in which the anisotropic site F is missing is to be obtained. FIG. 7 is an ultrasound image of an anterior talofibular ligament, which is an anisotropic site, and its surrounding. As shown in FIG. 7, because most of the reflection ultrasound waves reflected off the anterior talofibular ligament FB are not received by the ultrasound probe 2, the anterior talofibular ligament FB is not clearly shown, and for example, it is difficult to make diagnosis whether the anterior talfoibular ligament FB is ruptured or the like.

Figure 8A:
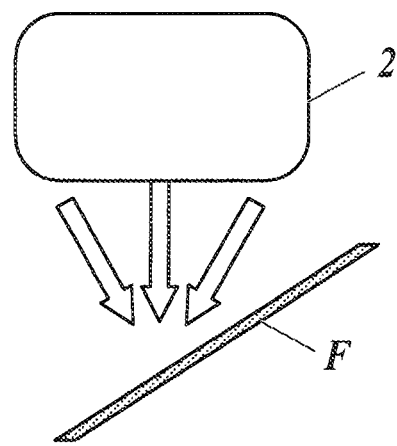
FIG. 8A is an explanatory diagram of a reflectance property of ultrasound waves.
Figure 8B:
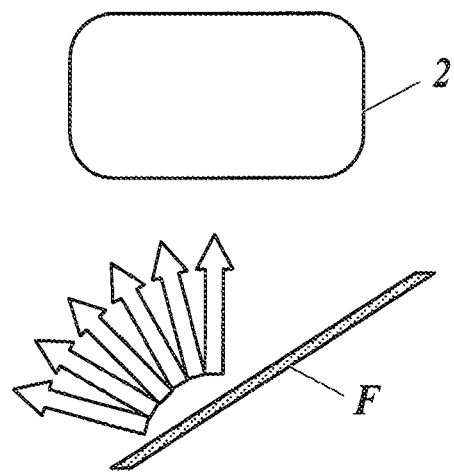
FIG. 8B is an explanatory diagram of a reflectance property of ultrasound waves.
Figure 9:
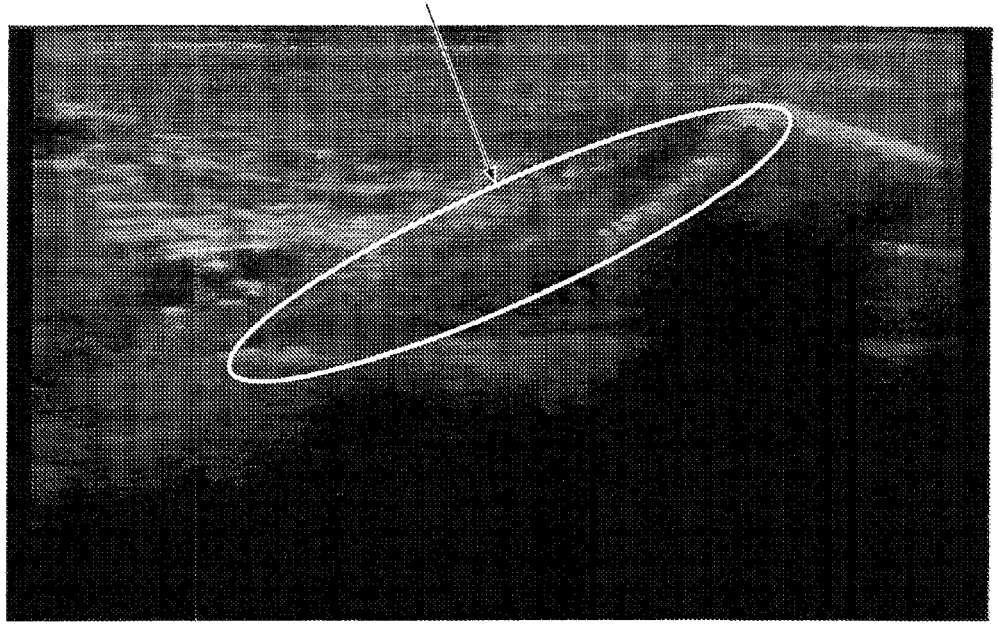
FIG. 9 is an explanatory diagram of an ultrasound image showing an anterior talofibular ligament and its surrounding obtained by conventional spatial compounding.

Moreover, if the spatial compounding is to be performed by scanning a plurality of scan regions having different angles as shown in FIG. 8A, although most of the reflection ultrasound waves are to be received depending on the transmission direction of the transmission beam, very small amount of the reflection ultrasound waves are to be received by the ultrasound probe 2 in other directions as shown in FIG. 8B. Therefore, as a result of performing the spatial compounding, the anisotropic site F is darker comparing to the tissue around the anisotropic site F and a good quality ultrasound image cannot be obtained. FIG. 9 is an ultrasound image of an area around an anterior talofibular ligament obtained by performing a conventional spatial compounding. As shown in FIG. 9, noises and speckles are reduced in the part other than the anterior talofibular ligament FB; however, because the received amount of the reflection ultrasound waves reflected off the anterior talofibular ligament FB is small, the anterior talofibular ligament FB is shown dark comparing to the surrounding tissue. Therefore, it is difficult to make diagnosis on the anterior talofibular ligament FB.

In response to the above problems, in the embodiment, the anisotropic site detection unit 16 can evaluate the anisotropic aspect (directional dependency) of ultrasound wave reflection in a subject and by appropriately performing spatial compounding according to the evaluation result, a good quality ultrasound image can be obtained. The evaluation of anisotropic aspect may be an evaluation of anisotropic direction or may be an evaluation of anisotropic level, for example. Both the direction and level may be evaluated.

In particular, first, if the spatial compounding is to be performed in the component image data sets obtained by scanning a plurality of scan regions, the synthesis method of the component image data sets used when generating synthetic image data is set so as to correspond with the direction of the anisotropic site which is detected.

Figure 10:
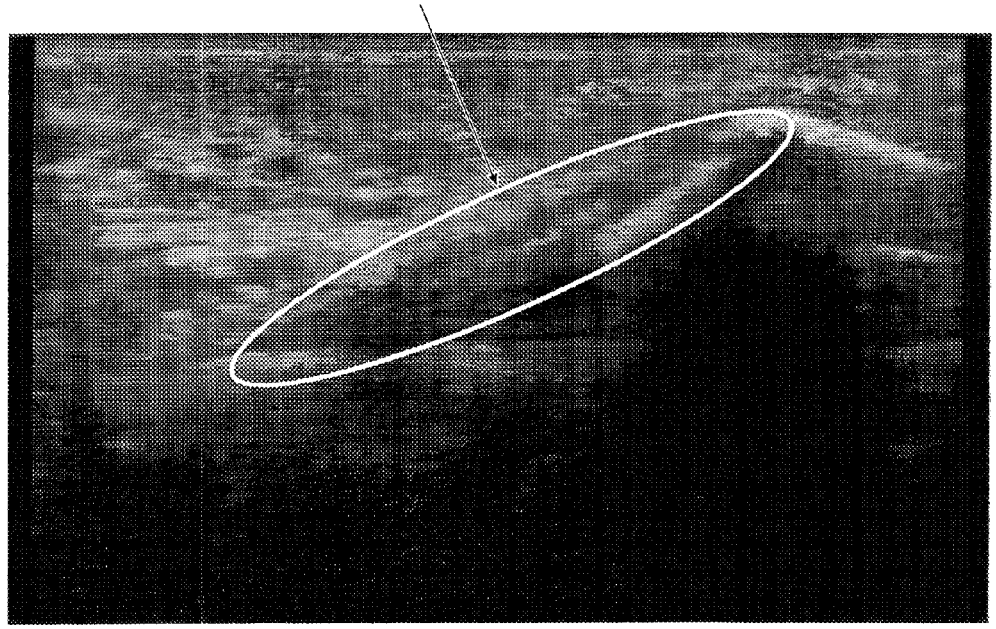
FIG. 10 is an explanatory diagram of an ultrasound image showing an anterior talofibular ligament and its surrounding obtained by spatial compounding according to the embodiment.

For example, scanning is performed at three steering angles of 0°, +10° and −10° and component image data sets of three scan regions are obtained. Then, the component image data set which best visualizes the anisotropic site is specified in a manner as described later. In other words, the direction of the anisotropic site is specified by evaluating the anisotropic aspect of the ultrasound wave reflection in a subject. As the synthesis method to be set, the spatial compounding is performed by weighting each of the obtained component image data sets of the three scan regions, and synthetic image data is generated. For example, in a case where weighting is to be carried out to each of the obtained component image data sets of the three scan regions, the spatial compounding is to be performed by carrying out larger rate weighting to those component image data sets that visualize the anisotropic site clearer; such as, the weighting rates being set to 50% and 40% for the two component image data sets in which the anisotropic site is clearly visualized and the weighting rate being set to 10% for the other component image dataset. The weighting rate for each component image data set can be set arbitrarily. FIG. 10 is a synthetic image obtained by performing the spatial compounding; wherein, among the component image data sets obtained by carrying out scanning at three different steering angles of 0°, +10 and −10°, weighting is set to 50% for the component image data set obtained by carrying out scanning at the steering angle 0°, weighting is set to 10% for the component image data set obtained by carrying out scanning at the steering angle +10° and weighting is set to 40% for the component image data set obtained by carrying out scanning at the steering angle −10°. According to such case, when compared with the ultrasound images of the anterior talofibular ligament FB shown in FIGS. 7 and 9, it is clearly shown that the ultrasound image of the anterior talofibular ligament FB in FIG. 10 is clearer. With such good quality ultrasound image, diagnosis can be more accurate.

In the above example, weighting rate is set for each of the plurality of component image data sets when the spatial compounding is to be performed. However, the spatial compounding may be performed after edge enhancement processing is performed on component image data sets which clearly visualize the anisotropic site as the synthesis method.

Secondly, the anisotropic aspect of the ultrasound wave reflection is evaluated for each of the component image data sets obtained by carrying out scanning in a plurality of scan regions having predetermined steering angles to detect the direction of the anisotropic site, and the transmission/reception conditions of ultrasound waves are set according to the detected direction of the anisotropic site. The transmission/reception conditions of ultrasound waves are, for example, the steering angles and the number of scan regions applied when obtaining the component image data sets. Alternatively, the transmission/reception conditions of ultrasound waves can be set by changing the aperture for receiving ultrasound waves by setting the transducers of receive signals to be used for performing phasing addition. More in particular, the aperture can be enlarged by changing the channel of the aperture for receiving signals to 72 channels from 64 channels at the time when the anisotropic site is detected, for example.

Figure 11:
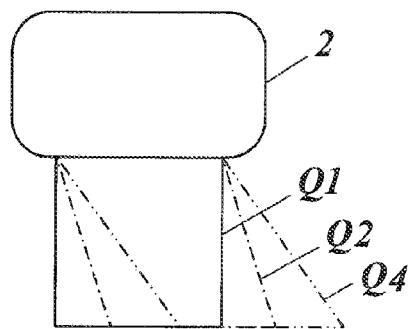
FIG. 11 is an explanatory diagram of scan regions to be scanned by ultrasound waves.
Figure 12:
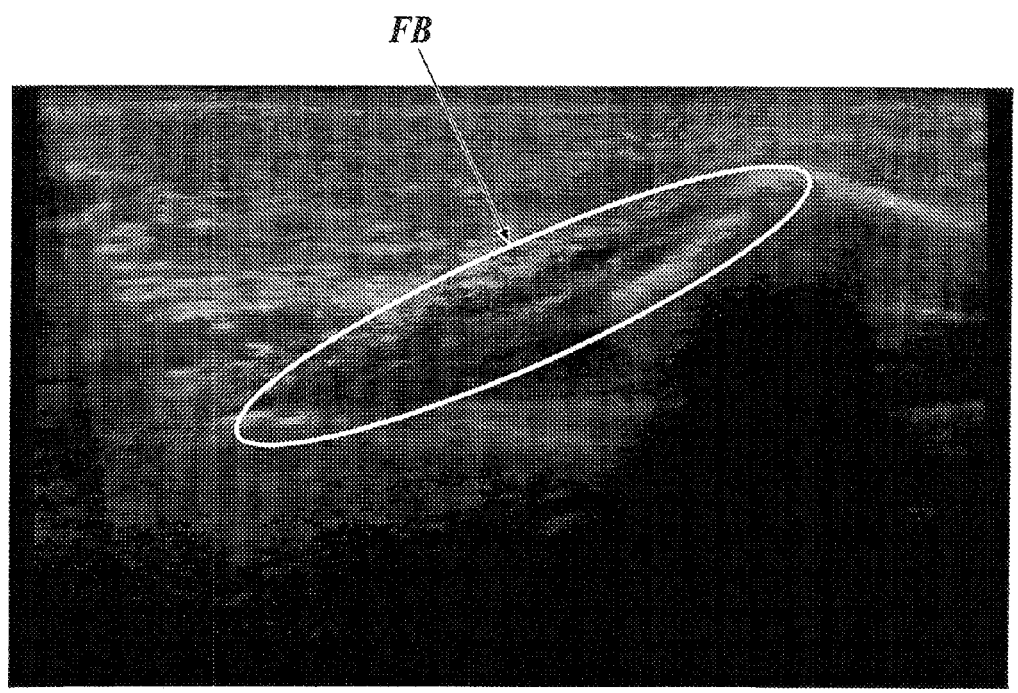
FIG. 12 is an explanatory diagram of an ultrasound image showing an anterior talofibular ligament and its surrounding obtained by spatial compounding according to the embodiment.

As shown in FIG. 3, component image data sets of three scan regions Q1 to Q3 are obtained by carrying out scanning at three different steering angles which are 0°, +10° and −10°. The anisotropic aspects of ultrasound wave reflection are evaluated in these component image data sets to specify the direction of the anisotropic site. Here, it is assumed that the component image data set of the scan region Q2 where scanning is carried out at the steering angle −10° clearly visualizes the anisotropic site. In such case, as a process for setting the transmission/reception conditions of ultrasound waves, component image data sets of three scan regions Q1, Q2 and Q4 are newly obtained by carrying out scanning at three steering angles of 0°, −10° and −20° as shown in FIG. 11. Then, the spatial compounding is performed for the component image data sets which are obtained after changing the steering angles and synthetic image data is generated. FIG. 12 is a synthetic image obtained by performing the spatial compounding for the component image data sets obtained by carrying out scanning at the steering angles of 0°, −10° and −20°. When this image is compared to the ultrasound images of the anterior talofibular ligament FB shown in FIGS. 7 and 9, it is clearly shown that the ultrasound image of the anterior talofibular ligament FB in FIG. 12 is clearer. Therefore, a good quality ultrasound image in which the anisotropic site is clearly shown can also be obtained by the spatial compounding performed in a manner as described above.

Figure 13:
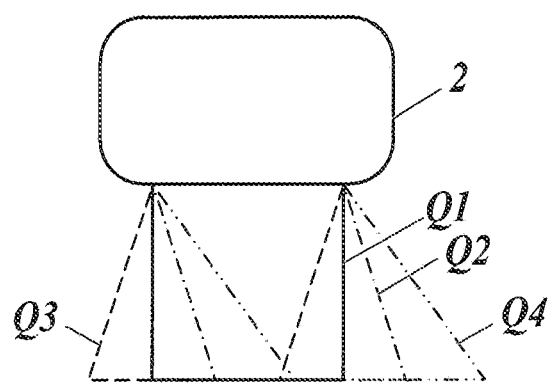
FIG. 13 is an explanatory diagram of scan regions to be scanned by ultrasound waves.

Alternatively, the spatial compounding may be performed in a manner as described below. That is, component image data sets of three scan region Q1, Q2 and Q3 are obtained by carrying out scanning at the steering angles of 0°, +10° and −10°. Then, the anisotropic aspects of ultrasound wave reflection are evaluated in the component image data sets and the direction of the anisotropic site is specified. Here, it is assumed that the component image data set of the scan region Q2 obtained by carrying out scanning at the steering angle −10° clearly visualizes the anisotropic site. In such case, as a process for setting the transmission/reception conditions of ultrasound waves, component image data sets of four scan regions Q1 to Q4 are newly obtained by carrying out scanning at the steering angles of 0°, +10°, −10° and −20° as shown in FIG. 13. Then, the spatial compounding is performed on the newly obtained component image data sets and synthetic image data is generated. In such manner, a good quality ultrasound image which clearly visualizes the anisotropic site can also be obtained.

Moreover, when generating synthetic image data with the newly obtained component image data sets after the transmission/reception conditions being set as described above, the synthesis method may be set according to the detected direction of the anisotropic site.

As for the evaluation of the anisotropic aspect of ultrasound wave reflection in a subject, evaluation may be performed in frame units, that is, every time a synthetic image data set is generated or may be performed at predetermined intervals (for example, every 30 frames).

Next, the spatial compounding performed by the ultrasound diagnostic imaging apparatus 100 according to the embodiment will be described.

First, the 1$^{st}$ example of spatial compounding will be described with reference to FIG. 14.

In the 1$^{st}$ example of spatial compounding, synthetic image data is generated as described below. The anisotropic site detection unit 16 calculates coherence factors on the basis of receive signals of scan regions obtained by the receiving unit 13. Then, the anisotropic site detection unit 16 determines the position of an anisotropic site from the coherence factors. In such way, the anisotropic site detection unit 16 evaluates the anisotropic aspect of ultrasound wave reflection. When the component image data sets of the scan regions are generated, the image processing unit 15 performs the spatial compounding by carrying out weighting of the component image data sets according to the determination result of the position of the anisotropic site obtained by the anisotropic site detection unit 16 to generate synthetic image data.

Coherence factor is a parameter which indicates the quality of a signal obtained by performing phasing addition to receive signals. The coherence factor is calculated by the rate of coherent sum with respect to incoherent sum, and a signal is in a good quality as the value is larger. That is, as the direction of a scan region approaches the angle facing the direction of the anisotropic site, more reflection ultrasound waves from the anisotropic site can be received. Therefore, a high coherence factor can be obtained.

More particularly, the coherence factors can be obtained in a manner as described below.

The anisotropic site detection unit 16 performs phasing addition of the receive signals after A/D conversion obtained from individual paths respectively corresponding to the transducers 2a. The receive signal Φ(t) after phasing addition can be expressed by the following formula (1). In the following formula (1), t expresses a reference time, Δt$_i$ expresses each delay time with respect to each of the reference times of channels 1 to N corresponding respectively to the plurality for transducers 2a used when receiving reflection ultrasound waves, S$_i$(t+Δt$_i$) expresses the size of a received signal of each channel at the timing delayed from the reference time t for the delay time Δt$_i$, that is, the size of the received signal after phasing is performed.

[Formula 1]

$$\phi(t) = \left| \sum_i S_i(t + \Delta t_i) \right| \quad (1)$$

Then, the anisotropic site detection unit 16 calculates the coherent sum CS(t) by raising the receive signal after phasing addition obtained as above to the second power.

Next, the anisotropic site detection unit 16 calculates an incoherent sum. Incoherent sum can be obtained by raising each of the receive signals after phasing of the channels 1 to N to the second power and by adding the obtained results and multiplying the obtained sum by the number of channels (N). In other words, the incoherent sum IS(t) can be expressed by the following formula (2).

[Formula 2]

$$IS(t) = N \sum_i |S_i(t + \Delta t_i)|^2 \quad (2)$$

The anisotropic site detection unit 16 can calculate a coherence factor CF(t) by the following formula (3) according to the coherent sum CS(t) and the incoherent sum IS(t) which are obtained as described above.

$$CF(t)=CS(t)/IS(t) \quad (3)$$

As described above, when the coherence factors of the scan regions are obtained, it is clearly shown that the coherence factors are different between the scan regions with respect to the position corresponding to the anisotropic site when the anisotropic site exists in a scan region because the steering angles are different for the scan regions. In other words, because the anisotropic site is a fibrous tissue such as a tendon or a ligament, if a plurality of scan regions are compared to each other by their coherence factors, the differences appear in linear manners or in curved manners. With these differences, the anisotropic site detection unit 16 can determine the position of the anisotropic site. In a case where the anisotropic site exists in a scan region, the part where the coherence factor is low appears in a linear manner or in a curved manner in the scan region, and thereby, the position of the anisotropic site can be determined. Further, by the anisotropic site detection unit 16 determining the scan region having the high coherence factor at the position corresponding to the anisotropic site among the plurality of scan regions, the scan region which best visualizes the anisotropic site can be specified. As a result of determining the anisotropic site as described above, the anisotropic site detection unit 16 sets the weighting rate for each of the scan regions. After the component image data sets of the scan regions are generated, the image processing unit 15 carries out weighting for each component image data set according to the weighting rate of the corresponding scan region set by the anisotropic site detection unit 16, and synthesizes the weighted component image data sets to generate synthetic image data.

Here, in the $1^{st}$ example of spatial compounding described above, the position of the anisotropic site is determined by calculating the coherence factors of the component image data sets, using the whole component image data set, and the scan region which best visualizes the anisotropic site is specified. However the position of the anisotropic site may be determined by other examples of spatial compounding described below and coherence factors of the parts corresponding to the determined anisotropic site may be calculated to specify the scan region which best visualizes the anisotropic site.

Next, the $2^{nd}$ example of spatial compounding will be described with reference to FIG. 15.

In the $2^{nd}$ example of spatial compounding, synthetic image data is generated in a manner as described below. The anisotropic site detection unit 16 performs frequency analysis based on the sound ray data generated by the phasing addition circuit of the receiving unit 13. The anisotropic site detection unit 16 determines the position of the anisotropic site from the frequency analysis results. In such way, the anisotropic site detection unit 16 evaluates the anisotropic aspects of ultrasound wave reflection. The image processing unit 15 generates component image data sets of the scan regions, and thereafter, performs the spatial compounding by carrying out weighting of the component image data sets according to the determination result of the position of the anisotropic site obtained by the anisotropic site detection unit 16 to generate synthetic image data.

Figure 16A:
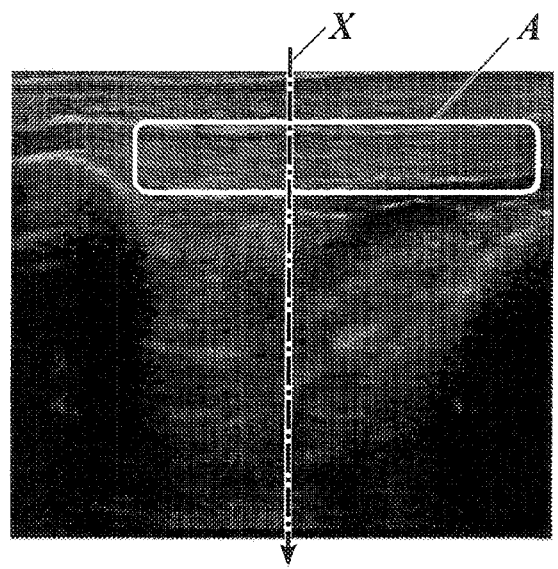
FIG. 16A is an explanatory diagram of a characteristic of sound ray data at an anisotropic site.
Figure 16B:
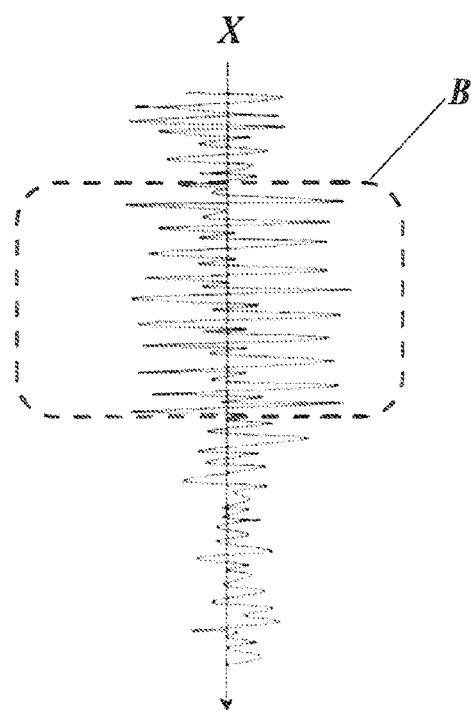
FIG. 16B is an explanatory diagram of a characteristic of sound ray data at an anisotropic site.

The anisotropic site such as a tendon or a ligament is formed of aligned plurality of fibrous tissues. When such anisotropic site is to be visualized by transmitting and receiving ultrasound waves, there are some cases where the image appears as stripes as shown in the part enclosed with a line A in FIG. 16A. Such unique pattern is called "fibrillar-pattern". Because this "fibrillar-pattern" has certain regularity, the part shown by the dot-dashed line X in FIG. 16A includes a unique signal waveform as expressed in the area enclosed with dotted line B in FIG. 16B. In the $2^{nd}$ example of spatial compounding, the anisotropic site is specified by extracting the parts showing this unique signal waveform by analyzing the frequency components of sound ray data. In such way, the anisotropic site detection unit 16 can determine the position of the anisotropic site. Further, the anisotropic site detection unit 16 determines the scan region having great signal intensity at the position corresponding to the anisotropic site among the plurality of scan regions to specify the scan region best visualizes the anisotropic site. As a result of the anisotropic site detection unit 16 determining the anisotropic site as described above, the weighting rates of the scan regions are set. The image processing unit 15 generates the component image data sets of the scan regions, and thereafter, carries out weighting of the component image data sets according to the weighting rates of their respective scan regions which are set by the anisotropic site detection unit 16 and synthesizes the weighted component image data sets to generate synthetic image data.

Figure 17:
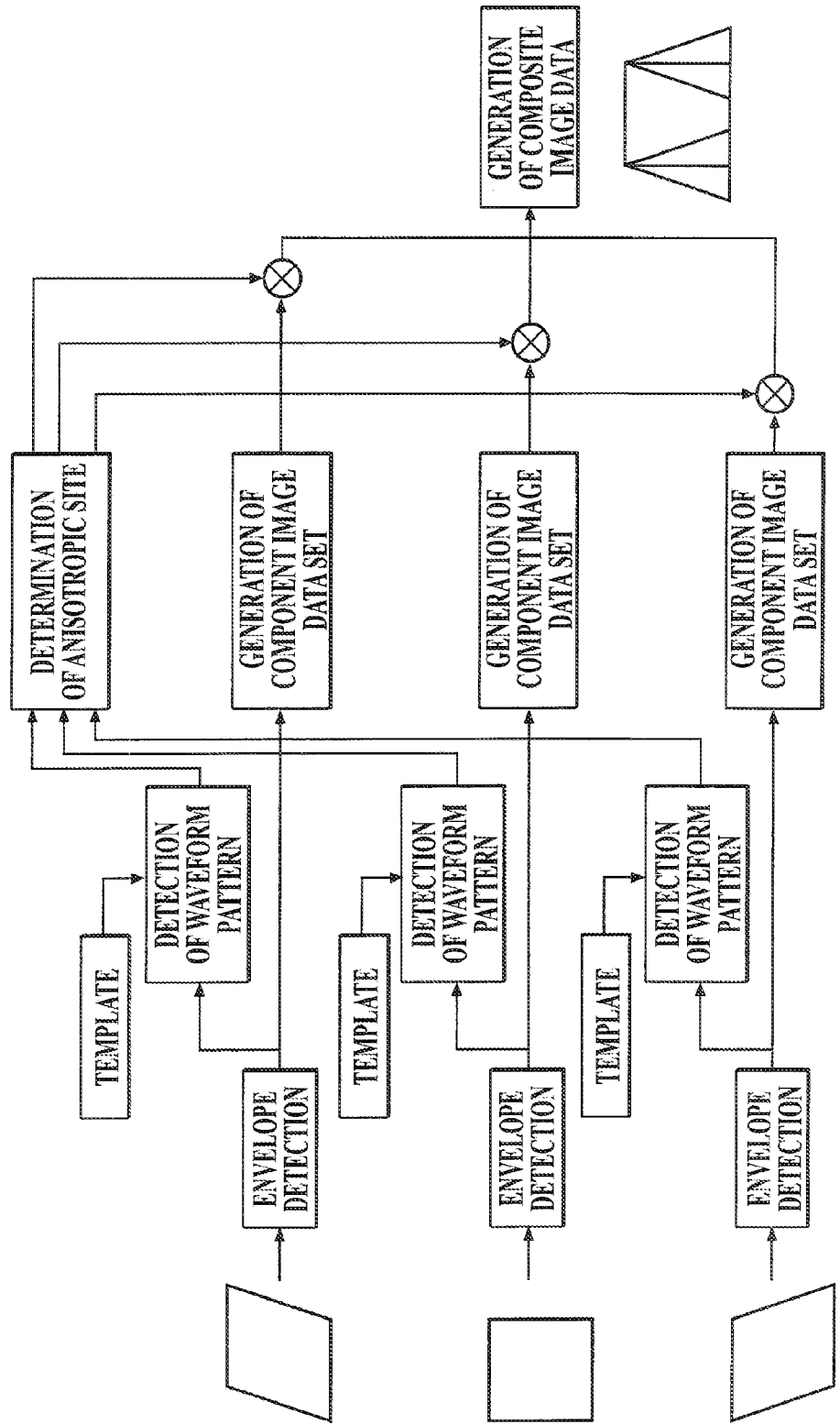
FIG. 17 is an explanatory diagram of a processing flow of the $3^{rd}$ example of spatial compounding.

Next, the $3^{rd}$ example of spatial compounding will be described with reference to FIG. 17.

In the $3^{rd}$ example of spatial compounding, synthetic image data is generated in a manner as described below. The anisotropic site detection unit 16 detects a waveform pattern in sound ray data to which envelop detection is performed by the image generating unit 15. The detection of the waveform pattern is performed by a template indicating a predetermined waveform being held in the anisotropic site detection unit 16 and comparing the sound ray data on which envelope detection is performed to the template, for example. The anisotropic site detection unit 16 determines the position of the anisotropic site from the detection results of the waveform patterns. In such way, the anisotropic site detection unit 16 evaluates the anisotropic aspect of ultrasound wave reflection. In particular, the position of the anisotropic site is specified by extracting the part in the signal waveform having high correlativity with the template in the sound ray data. Then, the image processing unit 15 generates component image data sets of the scan regions, and thereafter, the image processing unit 15 functions to perform the spatial compounding by carrying out weighting of the component image data sets according to the determination result of the position of the anisotropic site obtained by the anisotropic site detection unit 16 to generate synthetic image data.

In the $2^{nd}$ example of spatial compounding, the sound ray data of the anisotropic site such as a tendon or a ligament show a unique signal waveform as described above. Therefore, even in a case where envelope detection is performed for such sound ray data, the unique signal waveform is maintained. In the $3^{rd}$ example of spatial compounding, the sound ray data to which envelope detection is performed and the template are compared to each other and the anisotropic site is specified by extracting the part having high correlativity. In such way, the anisotropic site detection unit 16 can determine the position of the anisotropic site. Then, the anisotropic site detection unit 16 determines the scan region having a great signal intensity at the position corresponding to the anisotropic site among the plurality of scan regions to specify the scan region which best visualizes the anisotropic site. As a result of determining the anisotropic site as described above, the anisotropic site detection unit 16 sets weighting rates for the scan regions. Then, the image processing unit 15 generates component image data sets of the scan regions, and thereafter, carries out weighting of the component image data sets according to the weighting rates of their corresponding scan regions set by the anisotropic site detection unit 16 and synthesizes the weighted component image data sets to generate synthetic image data.

Figure 18:
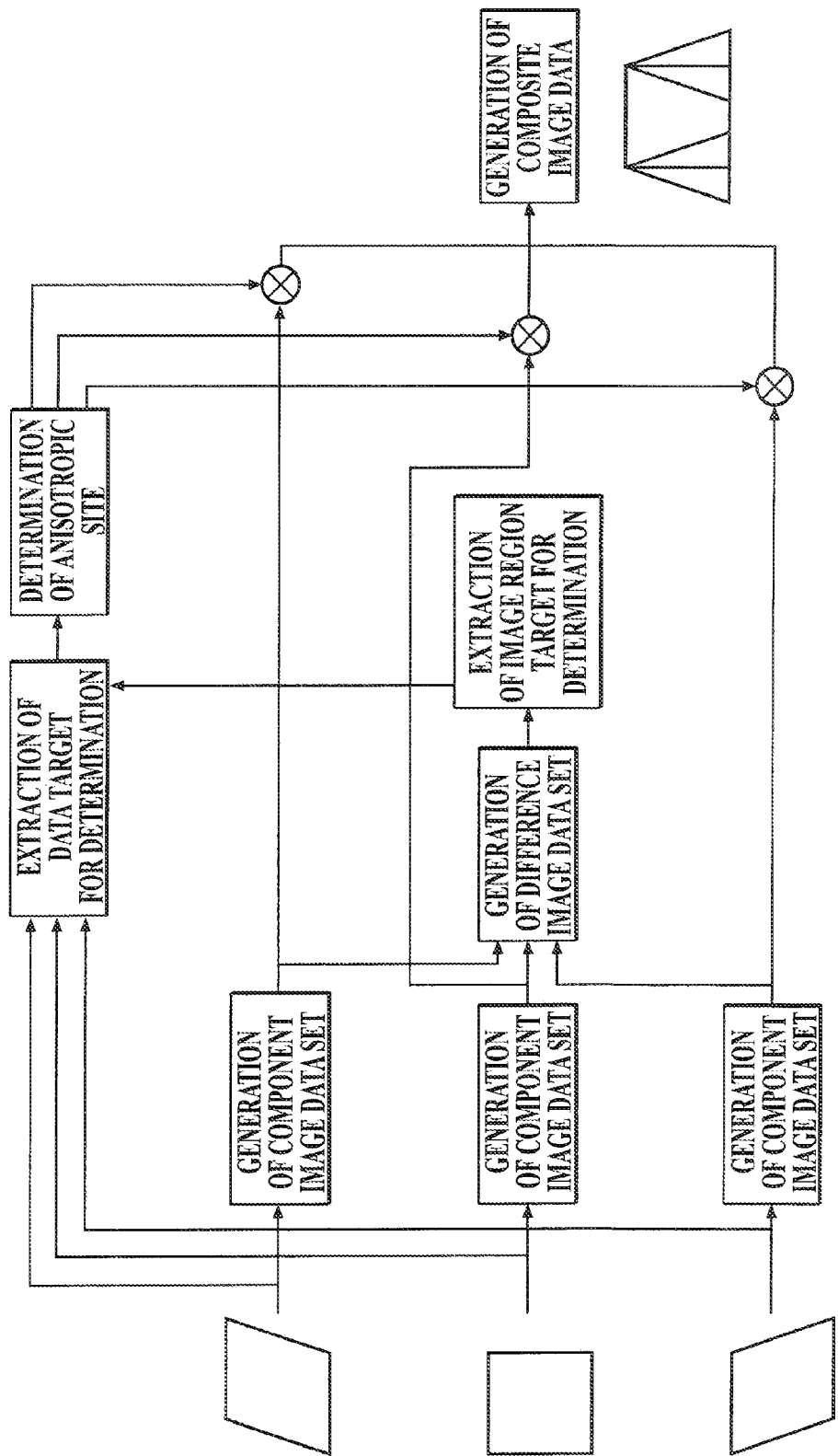
FIG. 18 is an explanatory diagram of a processing flow of the $4^{th}$ example of spatial compounding.

Next, the $4^{th}$ example of spatial compounding will be described with reference to FIG. 18.

In the $4^{th}$ example of spatial compounding, synthetic image data is generated in a manner as described below. The anisotropic site detection unit 16 generates a difference image data set which shows difference in luminescence between the component image data sets of the scan regions generated by the image processing unit 15. In a case where three component image data sets are generated, for example, the difference image data set is generated for any two component image data sets which are selected arbitrarily among the three component image data sets. Which component image data sets are to be used can be set arbitrarily. Further, the difference image data set can be generated for each of all combinations of two component image data sets among the three component image data sets. The anisotropic site detection unit 16 extracts an image region where the luminescence difference is equal to or greater than a predetermined threshold in the difference image data sets generated as described above. The anisotropic site detection unit 16 extracts the sound ray data of the part corresponding to the extracted image region as the data target for evaluation of anisotropic aspect of ultrasound wave reflection. The anisotropic site detection unit 16 performs the determination of the position of the anisotropic site described in the spatial compounding of the $1^{st}$ to $3^{rd}$ examples described above (anisotropic site determination processing) with respect to the extracted sound ray data. The image processing unit 15 carries out weighting of the component image data sets according to the determination results of the position of the anisotropic site obtained by the anisotropic site detection unit 16 to generate synthetic image data.

According to the $4^{th}$ example, determination of the position of the anisotropic site is performed on the partial sound ray data including the part corresponding to the anisotropic site. Therefore, detection accuracy of the position of the anisotropic site is improved and processing load is reduced.

Figure 19:
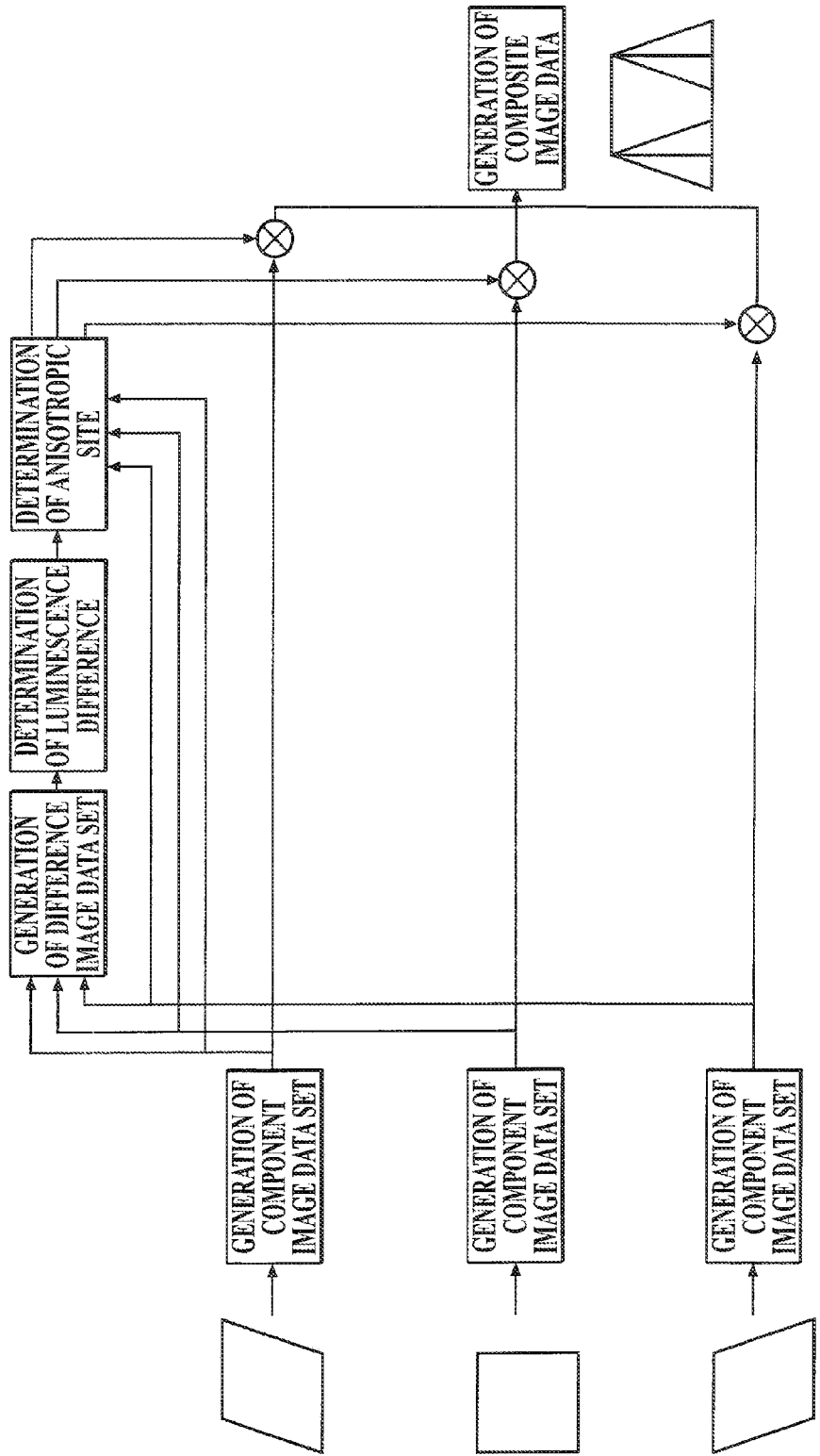
FIG. 19 is an explanatory diagram of a processing flow of the $5^{th}$ example of spatial compounding.

Next, the $5^{th}$ example of spatial compounding will be described with reference to FIG. 19.

In the $5^{th}$ example of spatial compounding, synthetic image data is generated in a manner as described below. The anisotropic site detection unit 16 generates difference image data sets which show differences in luminescence between the component image data sets of the scan regions generates by the image processing unit 15. In a case where three component image data sets are generated, for example, the difference image data sets are generated for all of the combinations of any two component image data sets among the three component image data sets. For example, in a case where component image data sets are obtained by carrying out scanning at the steering angles of 0°, +10° and −10°, the difference image data set showing the difference in luminescence between the component image data set obtained by carrying out scanning at the steering angle −10° and the component image data set obtained by carrying out scanning at the steering 0°, the difference image data set showing the difference in luminescence between the component image data set obtained by carrying out scanning at the steering angle 0° and the component image data set obtained by carrying out scanning at the steering +10° and the difference image data set showing the difference in luminescence between the component image data set obtained by carrying out scanning at the steering angle −10° and the component image data set obtained by carrying out scanning at the steering +10° are generated. The anisotropic site detection unit 16 performs a luminescence difference determination where the part where the luminescence difference is equal to or greater than a predetermine threshold is extracted from each of the above obtained difference image data sets. The anisotropic site detection unit 16 specifies the anisotropic site from the difference image data sets from which the parts where the luminescence difference is equal to or greater than the predetermined threshold is extracted and further specifies the difference image data set having the greatest luminescence difference at the part corresponding to the anisotropic site. As for the specifying of an anisotropic site, for example, the anisotropic site can be specified by extracting a region where the part the luminescence difference is equal to or greater than a predetermined threshold is expressed in a linear manner or a curved manner. The anisotropic site detection unit 16 determines the component image data set having the greatest luminescence at the region corresponding to the anisotropic site among the component image data sets used for generating the difference image data set having the greatest luminescence difference at the part corresponding to the anisotropic site. In such way, the anisotropic site detection unit 16 evaluates the anisotropic aspects of ultrasound wave reflection. Thereby, the scan region which best visualizes the anisotropic site is specified. As a result of determining the anisotropic site as described above, the anisotropic site detection unit 16 sets the weighting rates for the scan regions. The image processing unit 15 carries out weighting of the component image data sets according to the weighting rates set for their respective scan regions which are set by the anisotropic site detection unit 16 and synthesizes the weighted component image data sets to generate synthetic image data.

Figure 20:
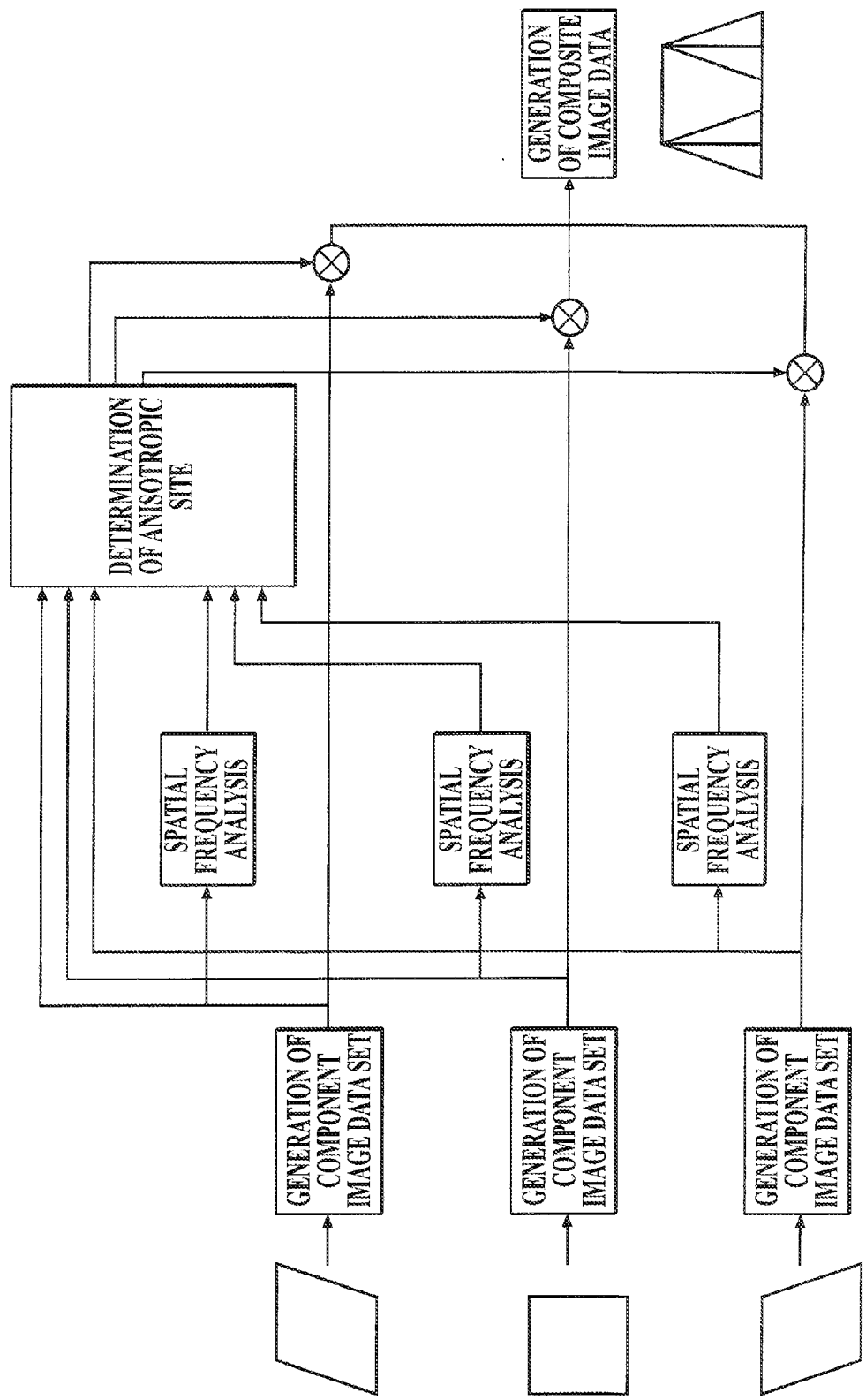
FIG. 20 is an explanatory diagram of a processing flow of the $6^{th}$ example of spatial compounding.

Next, the $6^{th}$ example of spatial compounding will be described with reference to FIG. 20.

In the $6^{th}$ example of spatial compounding, synthetic image data is generated in a manner as described below. The anisotropic site detection unit 16 analyzes the periodicity of each component image data set by performing spatial frequency analysis with respect to the component image data sets of the scan regions generated by the image processing unit 15. Spatial frequency analysis can be realized by performing, for example, a space FFT (Fast Fourier Transform) conversion with respect to each component image data set. In a case where an anisotropic site is included in a component image data set, a specific pattern is included in the result of spatial frequency analysis. The anisotropic site detection unit 16 specifies the position of the anisotropic site by detecting that the specific pattern is included in the result of spatial frequency analysis. Here, the position of the anisotropic site may be specified by generating difference image data sets of combinations of component image data sets of scan regions and performing spatial frequency analysis with respect to the difference image data sets. The anisotropic site detection unit 16 determines the component image data set having the greatest luminescence at the part corresponding to the anisotropic site among the component image data sets of the scan regions generated by the image processing unit 15. In such way, the anisotropic site detection unit 16 evaluates the anisotropic aspects of ultrasound wave reflection. Thereby, the scan region which best visualizes the anisotropic site is specified. The anisotropic site detection unit 16 sets the weighting rate for each scan region according to the determination of the anisotropic site determined as described above. The image processing unit 15 carries out weighting of the component image data sets according to the weighting rates of their respective scan regions set by the anisotropic site detection unit 16 and synthesizes the weighted component image data sets to generate synthetic image data.

Figure 21:
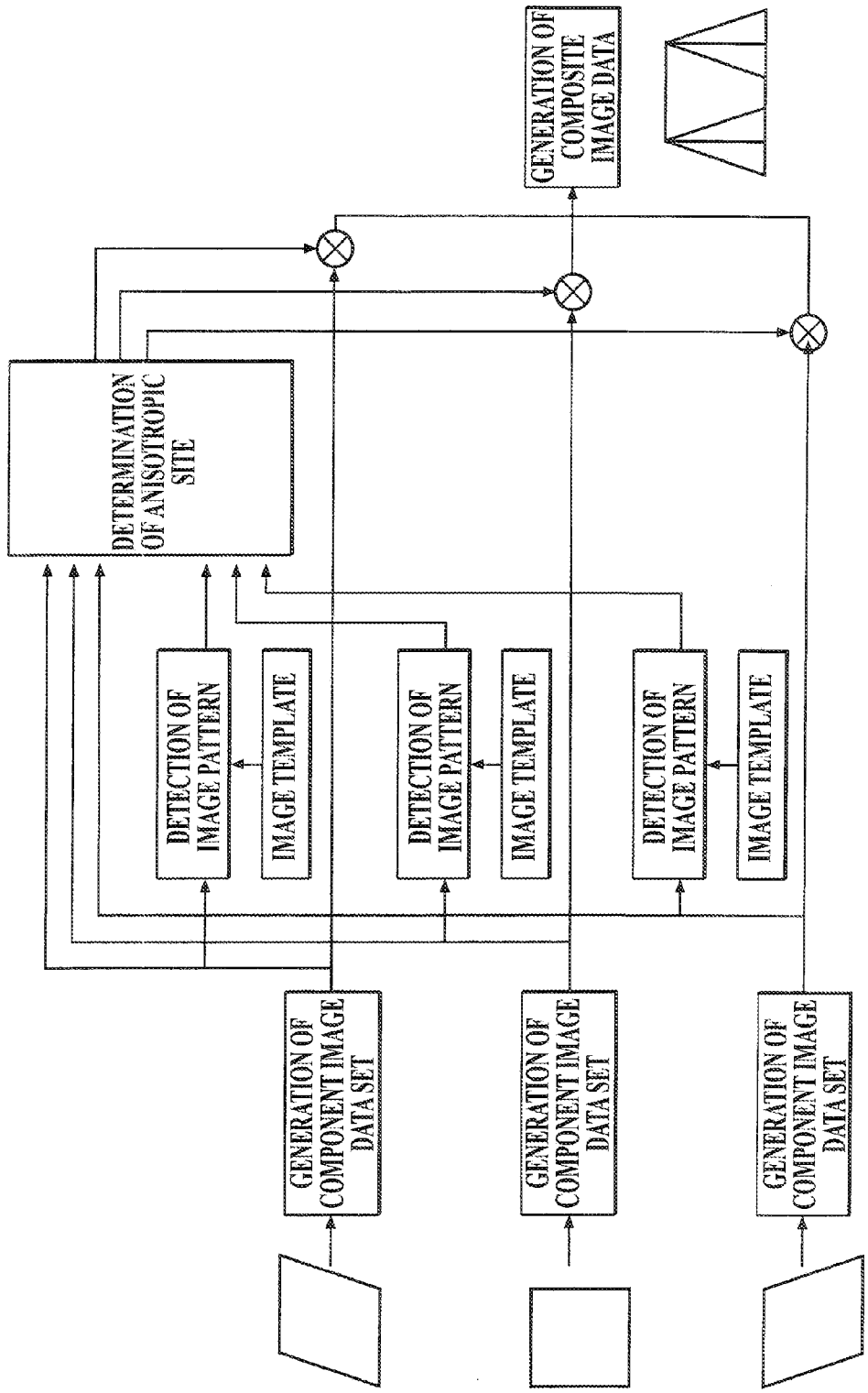
FIG. 21 is an explanatory diagram of a processing flow of the $7^{th}$ example of spatial compounding.

Next, the $7^{th}$ example of spatial compounding will be described with reference to FIG. 21.

In the $7^{th}$ example of spatial compounding, synthetic image data is generated in a manner as described below. With respect to each of the component image data sets of the scan regions generated by the image processing unit 15, the anisotropic site detection unit 16 performs detection of an image pattern that indicates an anisotropic site. Such image pattern may be referred to as the anisotropic site image pattern. The image pattern detection is carried out by, for example, a predetermined image template being held in the anisotropic site detection unit 16 and comparing the image template to the component image data sets. Then, the anisotropic site detection unit 16 determines the position of the anisotropic site from the detection results of the image pattern. In particular, the position of the anisotropic site is specified by extracting the regions having high correlativity with the image template of a predetermined size from the component image data sets. Then, the anisotropic site detection unit 16 determines the component image data set having the greatest luminescence at the part corresponding to the anisotropic site among the component image data sets of the scan regions generated by the image processing unit 15. In such way, the anisotropic site detection unit 16 evaluates the anisotropic aspects of ultrasound wave reflection. Thereby, the scan region which best visualizes the anisotropic site is specified. As a result of determining the anisotropic site as described above, the anisotropic site detection unit 16 sets the weighting rate for each of the scan regions. The image processing unit 15 carries out weighting of the component image data sets according to the weighting rates of their respective scan regions set by the anisotropic site detection unit 16 and synthesizes the weighted component image data sets to generate synthetic image data.

Figure 22:
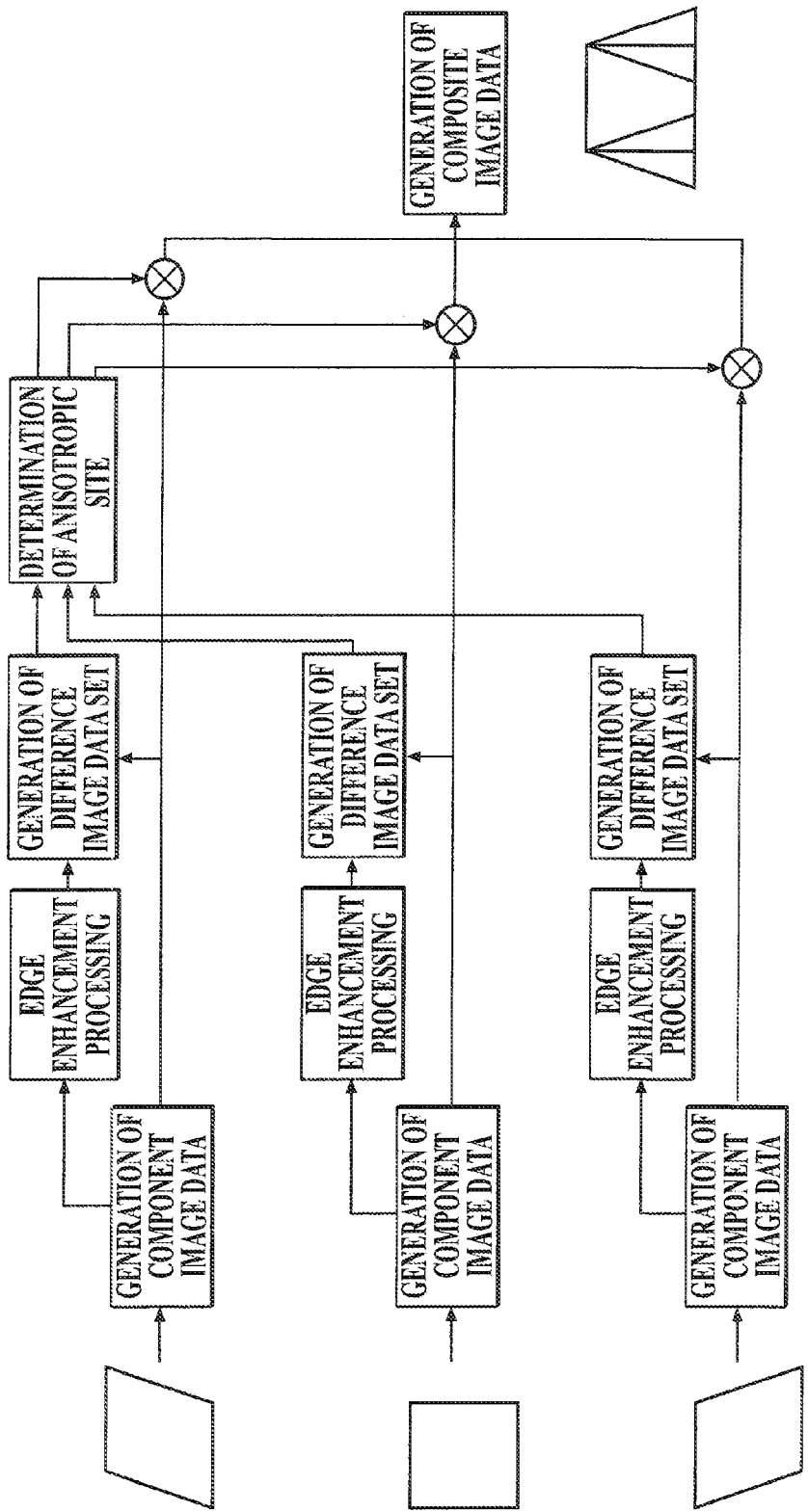
FIG. 22 is an explanatory diagram of a processing flow of the $8^{th}$ example of spatial compounding.

Next, the $8^{th}$ example of spatial compounding will be described with reference to FIG. 22.

In the $8^{th}$ example of spatial compounding, synthetic image data is generated in a manner as described below. With respect to each of the component image data sets of the scan regions generated by the image processing unit 15, the anisotropic site detection unit 16 performs edge enhancement processing to enhance the luminescence at the edge parts by using a predetermined edge filter. As for the method for enhancing the edges, an arbitrary method can be used. The anisotropic site detection unit 16 generates difference image data sets showing luminescence differences between the component image data sets in which edges are enhanced and the component image data sets before edge enhancement. Thereby, difference image data sets where only the edge parts are extracted are generated. In these difference image data sets, the anisotropic site detection unit 16 specifies the position of the anisotropic site. The specifying of the anisotropic site position can be realized by, for example, extracting a linear component or a curved component which is equal to or longer than a predetermined length in the difference image data sets. Then, the anisotropic site detection unit 16 determines the component image data set having the greatest luminescence at the part corresponding to the anisotropic site among the component image data sets of the scan regions generated by the image processing unit 15. In such way, the anisotropic site detection unit 16 evaluates the anisotropic aspects of ultrasound wave reflection. Thereby, the scan region which best visualizes the anisotropic site is specified. In a case where the edge parts constituted of lines or curves longer than a certain length is included in the difference image data sets from which edge parts are extracted, the content rate thereof may be calculated in each of the difference image data sets, and the scan region which best visualizes the anisotropic site may be specified by comparing the calculated content rates of the difference image data sets. As a result of detecting the anisotropic site as described above, the anisotropic site detection unit 16 sets the weighting rate for each of the scan regions. The image processing unit 15 carries out weighting of the component image data sets according to the weighting rates of their respective scan regions set by the anisotropic site detection unit 16 and synthesizes the weighted component image data sets to generate synthetic image data.

Figure 23:
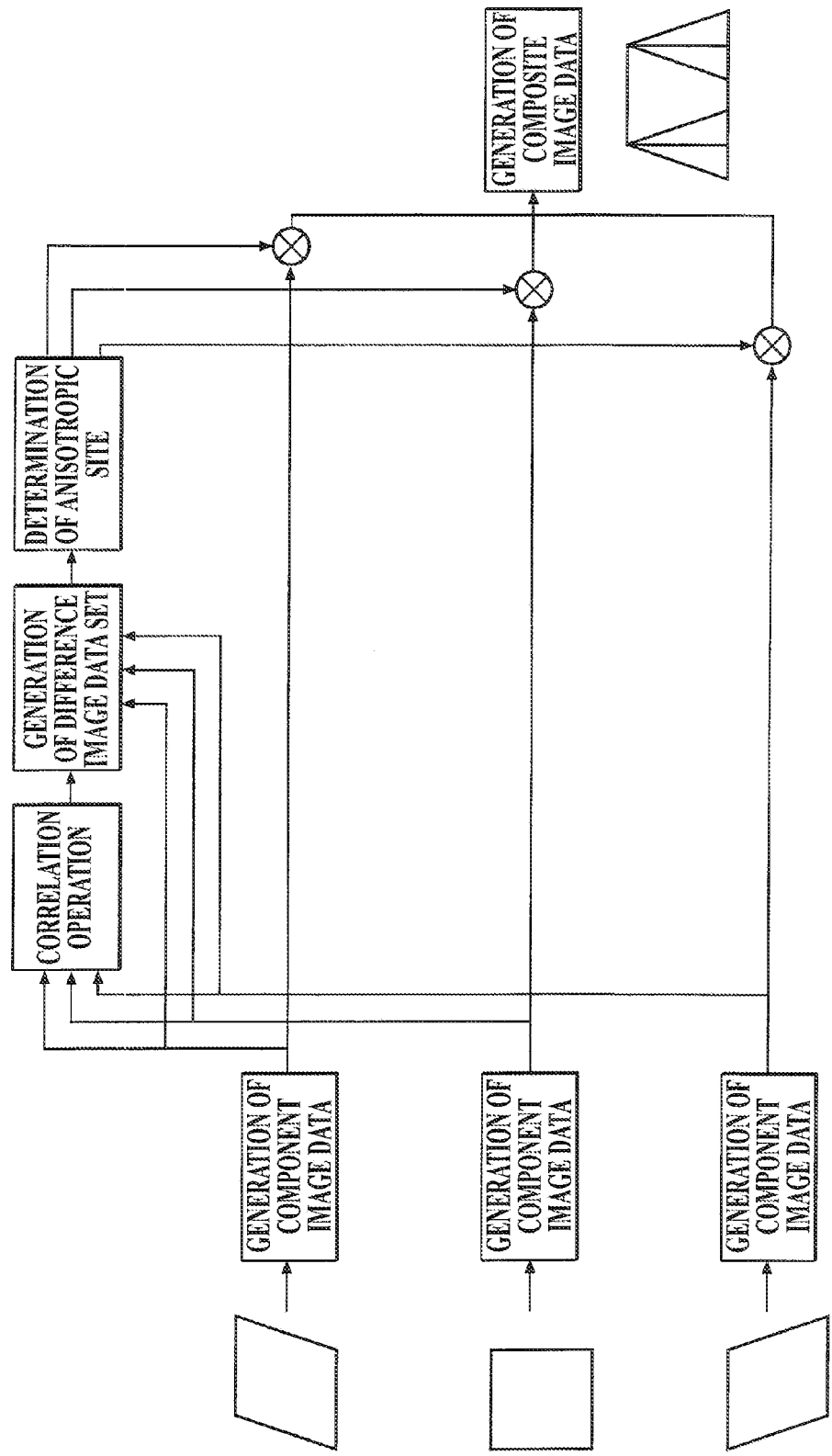
FIG. 23 is an explanatory diagram of a processing flow of the $9^{th}$ example of spatial compounding.

Next, the $9^{th}$ example of spatial compounding will be described with reference to FIG. 23.

In the $9^{th}$ example of spatial compounding, synthetic image data is generated in a manner as described below. The anisotropic site detection unit 16 carries out an operation to obtain the correlation coefficient between the component image data sets of the scan regions generated by the image processing unit 15 and specifies the position of the anisotropic site from the results. In particular, for example, in a case where three component image data sets are generated, correlation coefficient is obtained for each of the all combinations of two component image data sets of the three component image data sets. The correlation coefficient P can be obtained by the following formula (4).

[Formula 3]

$$P = \frac{\sum_{ij} \phi_i \phi_j}{\sum_i \phi_i^2} \quad (4)$$

If the correlation coefficient of each combination of the component image data sets obtained as described above is equal to or smaller than a predetermined threshold, the anisotropic site detection unit 16 determines that the anisotropic site is included in the component image data sets. When the anisotropic site detection unit 16 determines that the anisotropic site is included in the component image data sets, the anisotropic site detection unit 16 generates difference image data sets which show the luminescence difference between the component image data sets. Such difference image data sets are generated for all of the combinations of two component image data sets. The anisotropic site detection unit 16 determines the difference image data set having the greatest luminescence at the position corresponding to the anisotropic site among the difference image data sets generated as described above. The specifying method of the anisotropic site is as described above. The anisotropic site detection unit 16 determines the component image data set having the greatest luminescence at the region corresponding to the anisotropic site among the component image data sets used for generating the difference image data set having the greatest luminescence at the part corresponding to the anisotropic site. In such way, the anisotropic site detection unit 16 evaluates the anisotropic aspects of ultrasound wave reflection. Thereby, the scan region which best visualizes the anisotropic site is specified. As a result of detecting the anisotropic site as described above, the anisotropic site detection unit 16 sets the weighting rate for each of the scan regions. The image processing unit 15 carries out weighting of the component image data sets according to the weighting rates of their respective scan regions set by the anisotropic site detection unit 16 and synthesizes the weighted component image data sets to generate synthetic image data.

Figure 24:
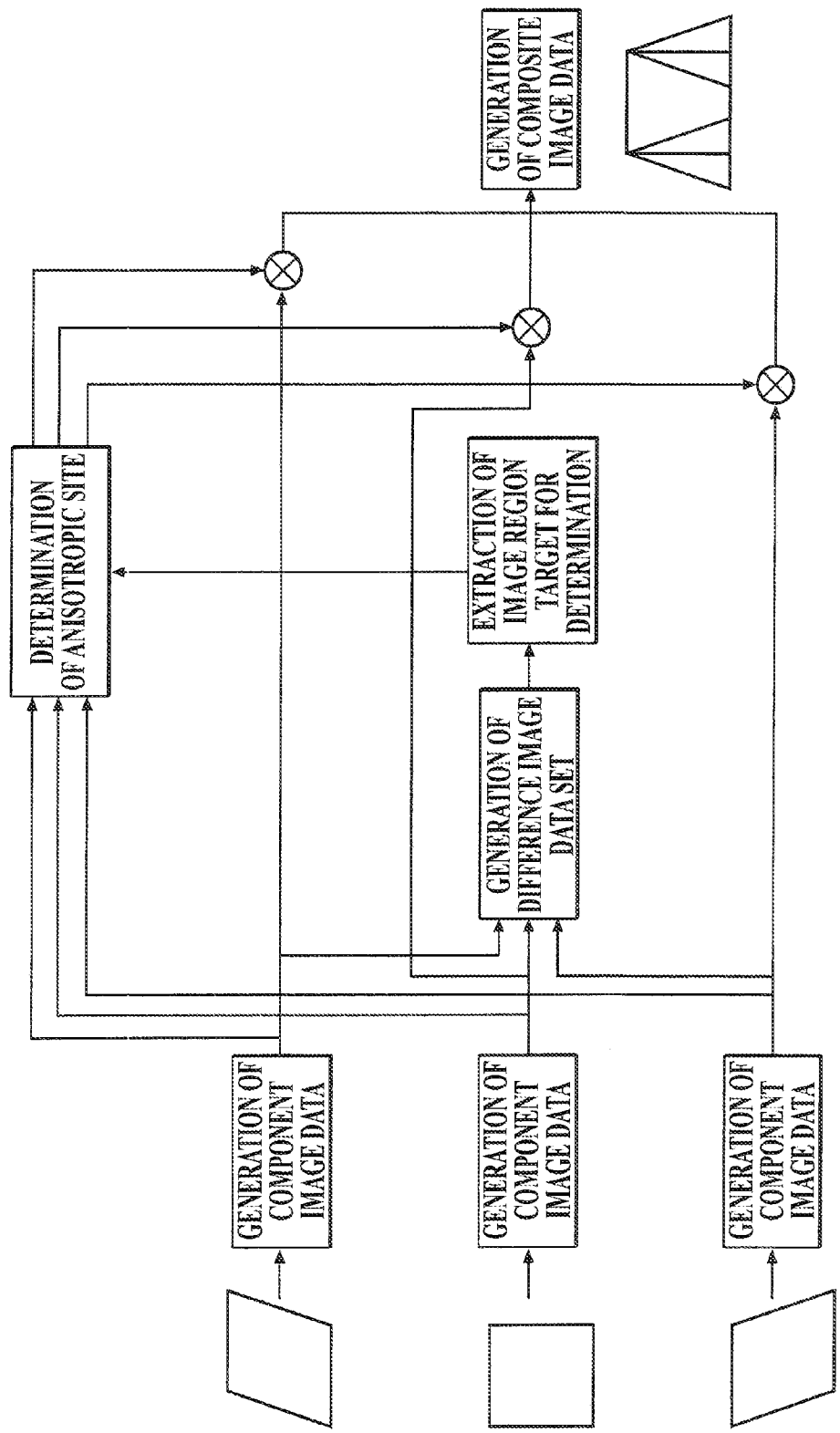
FIG. 24 is an explanatory diagram of a processing flow of the $10^{th}$ example of spatial compounding.

Next, the $10^{th}$ example of spatial compounding will be described with reference to FIG. 24.

In the $10^{th}$ example of spatial compounding, synthetic image data is generated in a manner as described below. The anisotropic site detection unit 16 generates a difference image data set which show luminescence differences between the component image data sets of scan regions generated by the image processing unit 15. In a case where three component image data sets are generated, for example, a difference image data set is generated for any two component image data sets of the three component image data sets. Which component image data sets are to be used can be set arbitrarily. Alternatively, difference image data sets may be generated for all of the combinations of two component image data sets of the three component image data sets. The anisotropic site detection unit 16 extracts the image region whose luminescence difference equals to or greater than a predetermined threshold in the difference image data set obtained as described above. With respect to the component image data sets of the part corresponding to the extracted image region, the anisotropic site detection unit 16 performs the determination of the position of the anisotropic site described in the spatial compounding of the $5^{th}$ to $9^{th}$ examples described above (anisotropic site determination processing). In such way, the anisotropic site detection unit 16 evaluates the anisotropic aspects of ultrasound wave reflection. The image processing unit 15 carries out weighting of the component image data sets according to the determination results of the position of the anisotropic site obtained by the anisotropic site detection unit 16 to generates synthetic image data.

According to the $10^{th}$ example, the determination of the position of the anisotropic site is performed with respect to a part of each component image data set that includes the anisotropic site. Therefore, detection accuracy of the position of the anisotropic site is improved and processing load is reduced.

Figure 25:
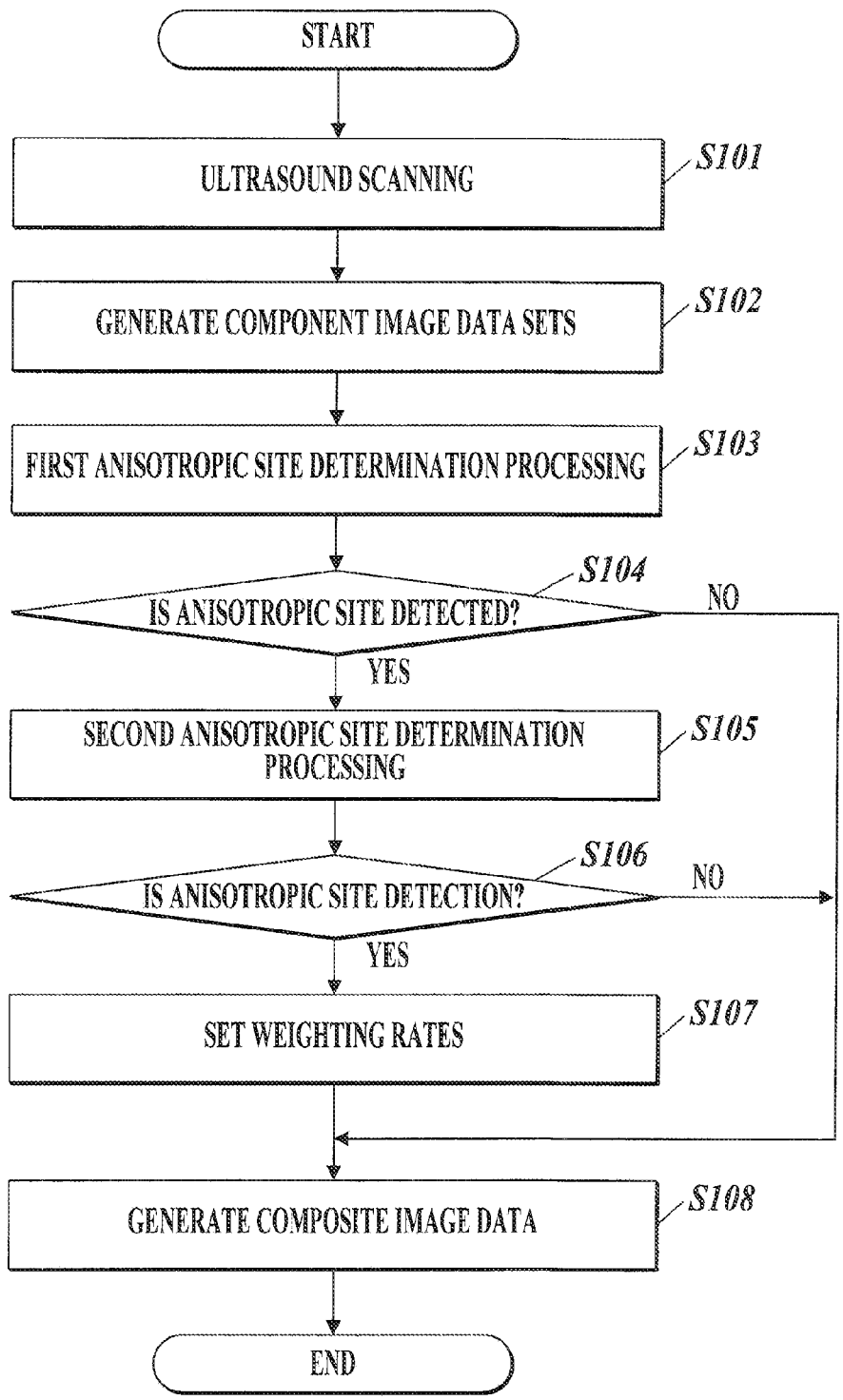
FIG. 25 is a flowchart for explaining a processing flow of the $11^{th}$ example of spatial compounding.

Next, the $11^{th}$ example of spatial compounding will be described with reference to FIG. 25.

In the $11^{th}$ example of spatial compounding, synthetic image data is generated in a manner as described below. The control unit 19 controls the transmitting unit 12 and the receiving unit 13 and performs ultrasound scanning with respect to each of the scan regions having different steering angles (step S101). The control unit 19 controls the image generation unit 14 and the image processing unit 15 and generates component image data sets of the scan regions according to the receive signals obtained by performing the ultrasound scanning as described above (step S102). The control unit 19 controls the anisotropic site detection unit 16 to perform the determination of the position of the anisotropic site described in either of the spatial compounding of the $1^{st}$ to $3^{rd}$ examples and the $5^{th}$ to $9^{th}$ examples (first anisotropic site determination processing) (step S103). The control unit 19 determines whether the anisotropic site is detected as a result of the first anisotropic site determination processing (step S104). If the control unit 19 determines that the anisotropic site is detected (step S104; Y), the control unit 19 controls the anisotropic site detection unit 16 to perform the determination of the position of the anisotropic site (second anisotropic site determination processing) described in the spatial compounding which is different from the determination performed for the first anisotropic site determination processing, the second anisotropic site determination processing being described in either of the spatial compounding of the $1^{st}$ to $3^{rd}$ examples and the $5^{th}$ to $9^{th}$ examples (step S105). The control unit 19 determines whether the anisotropic site is detected as a result of the second anisotropic site determination processing (step S106). If the control unit 19 determines that the anisotropic site is detected (step S106; Y), the control unit 19 controls the anisotropic site detection unit 16 and evaluates the anisotropic aspects of ultrasound wave reflection by specifying the component image data of the scan region, which best visualizes the anisotropic site, and sets the weighting rate for each scan region according to the evaluation result (step S107). The control unit 19 controls the image processing unit 15 to carry out weighting of the component image data sets according to the weighting rates of their respective scan regions set by the anisotropic site detection unit 16 and synthesizes the weighted component image data sets to generate synthetic image data (step S108) and ends the process. On the other hand, if the control unit 19 does not determine that the anisotropic site is detected in step S104 or step S106 (step S104; N, step S106; N), the control unit 19 equally weights the component image data sets and synthesizes the component image data sets to generate synthetic image data.

According to the $11^{th}$ example, detection accuracy of the position of the anisotropic site improves and the appropriate spatial compounding can be performed.

In the spatial compounding performed in the $11^{th}$ example, anisotropic site determination processing is performed twice. However, anisotropic site determination processing may be performed three times or more.

Figure 26:
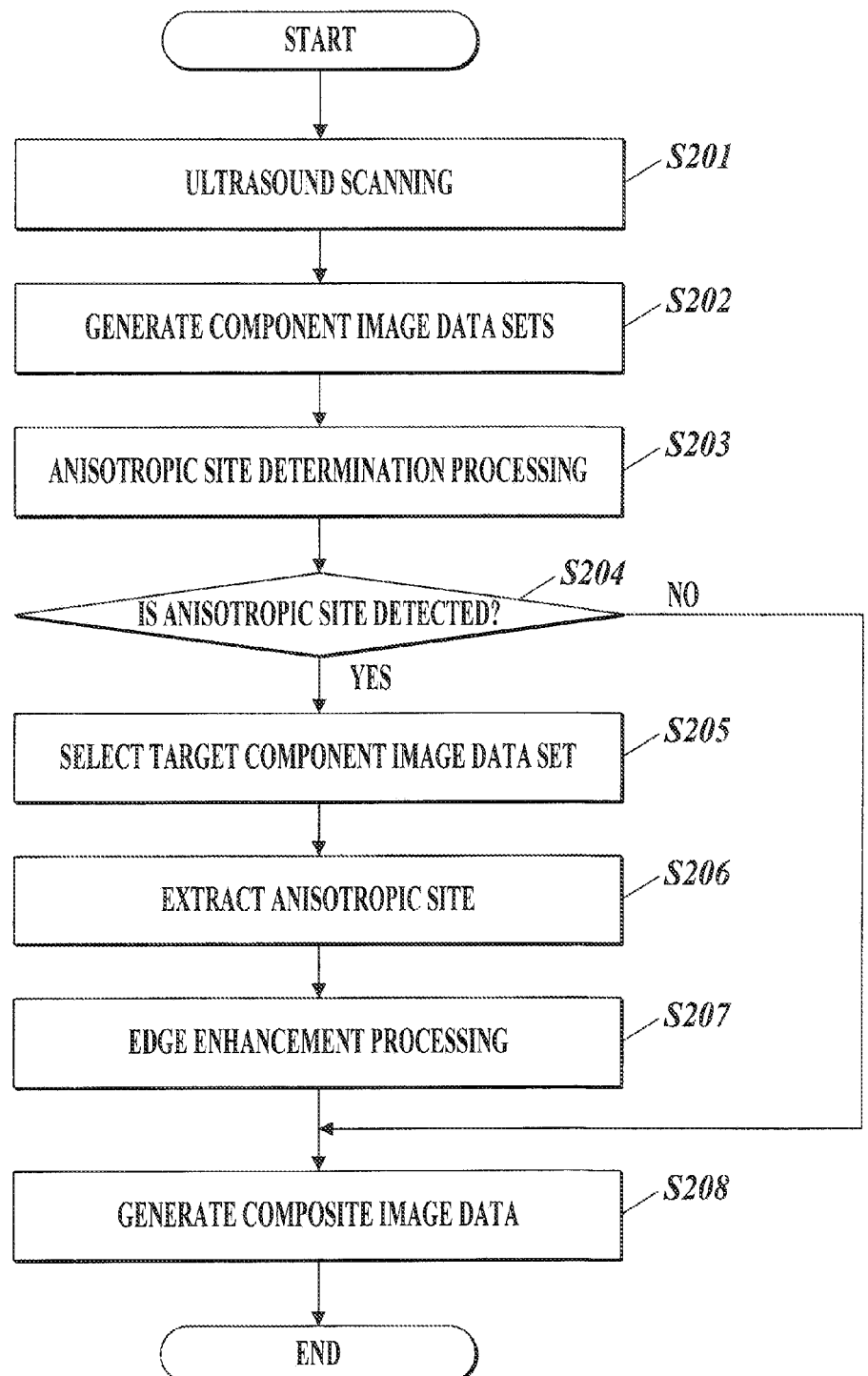
FIG. 26 is a flowchart for explaining a processing flow of the $12^{th}$ example of spatial compounding.

Next, the $12^{th}$ example of spatial compounding will be described with reference to FIG. 26.

In the $12^{th}$ example of spatial compounding, synthetic image data is generated in a manner as described below. The control unit 19 controls the transmitting unit 12 and the receiving unit 13 to perform ultrasound scanning with respect to each of a plurality of scan regions having different steering angles (step S201). The control unit 19 controls the image generation unit 14 and the image processing unit 15 to generate component image data sets of the scan regions according to the receive signals obtained by carrying out the ultrasound scanning as described above (step S202). The control unit 19 controls the anisotropic site detection unit 16 to perform the determination of the position of the anisotropic site (anisotropic site determination processing) described in either of the spatial compounding of the $1^{st}$ to $3^{rd}$ examples and the $5^{th}$ to $9^{th}$ examples (step S203). The control unit 19 determines whether an anisotropic site is detected as a result of the anisotropic site determination processing (step S204). In this embodiment, the anisotropic aspects of ultrasound wave reflection can be evaluated in such way. If the control unit 19 determines that the anisotropic site is detected (step S204; Y), the control unit 19 selects a component image data set which is to be target for the after-mentioned edge enhancement processing (step S205). In particular, the control unit 19 specifies the component image data set of the scan region which best visualizes the anisotropic site as described above and sets this component image data set as the target for edge enhancement processing. The control unit 19 controls the anisotropic site detection unit 16 to extract the region that is to be the anisotropic site in the selected component image data set (step S206). The control unit 19 controls the anisotropic site detection unit 16 to perform the edge enhancement processing with respect to the extracted region wherein luminescence of edge parts are enhanced by using a predetermined edge filter (step S207). The control unit 19 controls the image processing unit 15 to synthesize the component image data set to which the edge enhancement processing is performed and other component image data sets to generate synthetic image data (step S208), and hereby ends the process. Here, the component image data sets are equally weighted. Alternatively, each component image data sets may be weighted with different weighting rates to generate synthetic image data. On the other hand, if the control unit 19 does not determine that the anisotropic site is detected in step S204 (step S204; N), the process of step S208 is executed with out executing the processes from step S205 to step S207. In the $12^{th}$ example, the synthetic image data is generated after the edge enhancement processing is performed to the region that is to be the anisotropic site. However, the region that is to be the anisotropic site and the other region may be separated in each component image data set, and the weighting rate may be set for each of the regions that are to be the anisotropic site to be synthesizes and equal weighting may be performed with respect to each of the other regions to be synthesized in order to generate synthetic image data.

According to the $12^{th}$ example, each region can be optimized for image synthesis and therefore, the anisotropic site can be visualized clearer.

In the above described $1^{st}$ to $12^{th}$ examples of spatial compounding, if the receive F value indicating the depth rate of the receive focal point with respect to the aperture (receiving aperture) of the receive signals to be used for performing phasing addition, the aperture being configured of transducers 2a, is set to 0.8 or smaller, this is preferable because the anisotropic site is visualized clearer. However, the present invention is not limited to this. Further, if the transmission F value indicating the depth rate of the transmission focal point with respect to the aperture (transmission aperture), the aperture being configured of transducers which transmit ultrasound waves, is set to 3 ore greater with respect to the receive F value, this is preferable because the anisotropic site is visualized clearer. More preferably, the transmission F value is set to a value between 3.0 and 3.5. However, the present invention is not limited to this.

Figure 27:
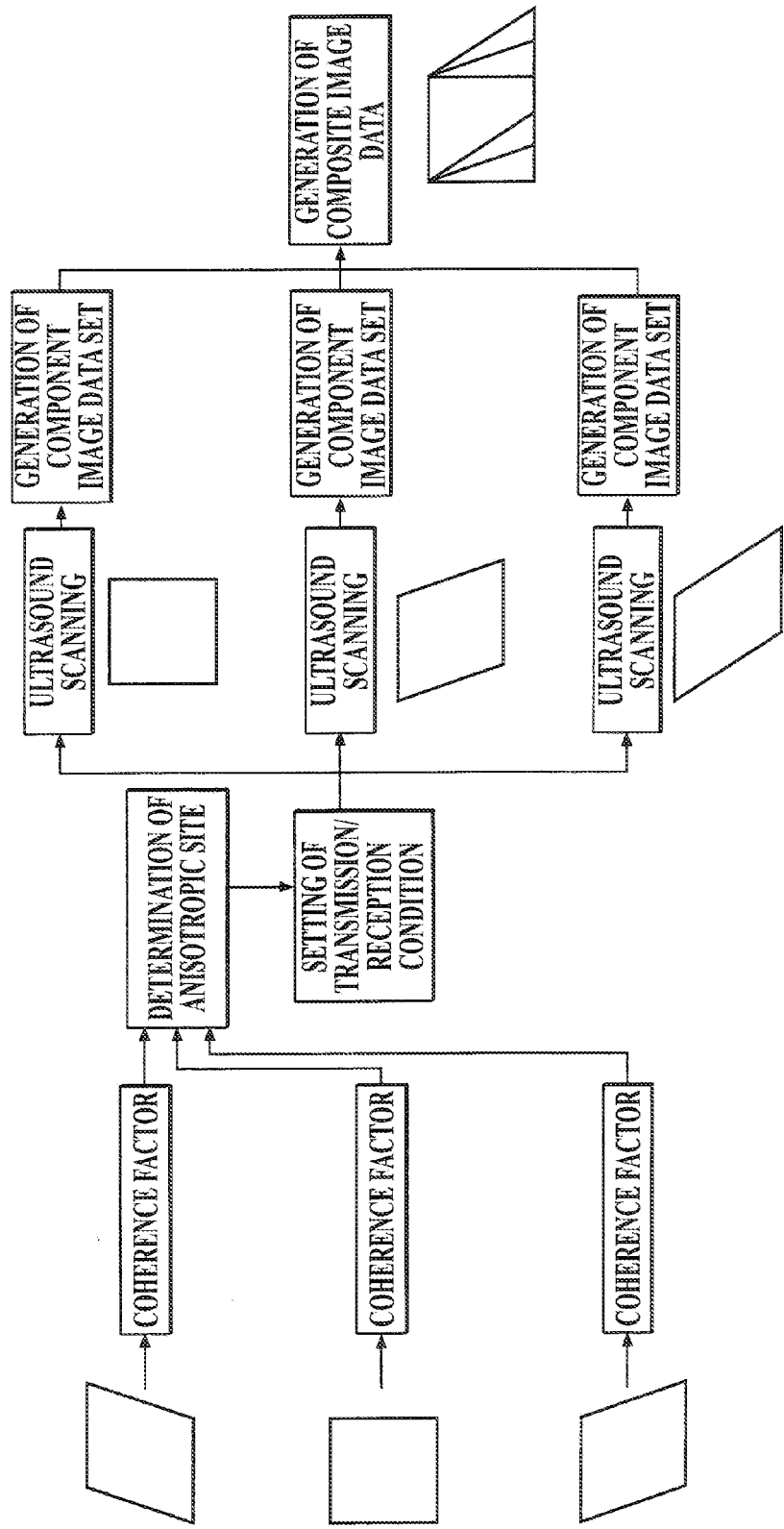
FIG. 27 is an explanatory diagram of a processing flow of the $13^{th}$ example of spatial compounding.

Next, the $13^{th}$ example of spatial compounding will be described with reference to FIG. 27.

In the $13^{th}$ example of spatial compounding, synthetic image data is generated in a manner as described below. The anisotropic site detection unit 16 calculates coherence factors according to the receive signals of the plurality of scan regions obtained by the receiving unit 13 as described in the $1^{st}$ example. Then, the anisotropic site detection unit 16 determines the position of the anisotropic site from the coherence factors. In such way, the anisotropic site detection unit 16 evaluates the anisotropic aspects of ultrasound wave reflection. According to the determined position of the anisotropic site, the anisotropic site detection unit 16 sets transmission/reception conditions of ultrasound waves. The transmission/reception conditions of ultrasound waves are, for example, the plurality of steering angles set when performing ultrasound scanning by the transmitting unit 12. After performing transmission and reception of ultrasound waves under the set transmission/reception conditions, component image data sets are respectively generated according to the receive signals of the plurality of scan regions which are received. The image processing unit 15 synthesizes the above generated component image data sets of the scan regions to generate synthetic image data. Here, the component image data sets are equally weighted when generating the synthetic image data.

For example, the coherence factors are calculated from the receive signals obtained for the plurality of scan regions by carrying out ultrasound scanning at each of the steering angles of 0°, +10° and −10°. Then, a scan region which visualizes the anisotropic site in a good condition is specified using the calculation results of the coherence factors. That is, the direction of the anisotropic site is specified. According to the specified direction of the anisotropic site, steering angles to be applied when carrying out ultrasound scanning are set. For example, as a result of coherence factor calculation, if it is determined that the anisotropic site in the scan region of steering angle −10° is best visualized, the steering angles to be applied when carrying out ultrasound scanning are set to 0°, −10° and −20°. Then, ultrasound scanning is carried out in each of the scan regions having steering angles of 0°, −10° and −20° to obtain component image data sets of the scan regions. The component image data sets of the scan regions obtained as described above are synthesized to generate synthetic image data.

In the $13^{th}$ example, if the differences between the coherence factors of the scan regions are greater than a predetermined value, ultrasound scanning is carried out again with changes in the steering angles and coherence factors are calculated again. This is repeated until the differences between the coherence factors of the scan regions become equal to or smaller than the predetermined value. In other words, when the steering angles fall on the angles which can visualize the anisotropic site in a good condition, the component image data sets of the scan regions obtained at those steering angles are used to generate the synthetic image data.

Figure 28:
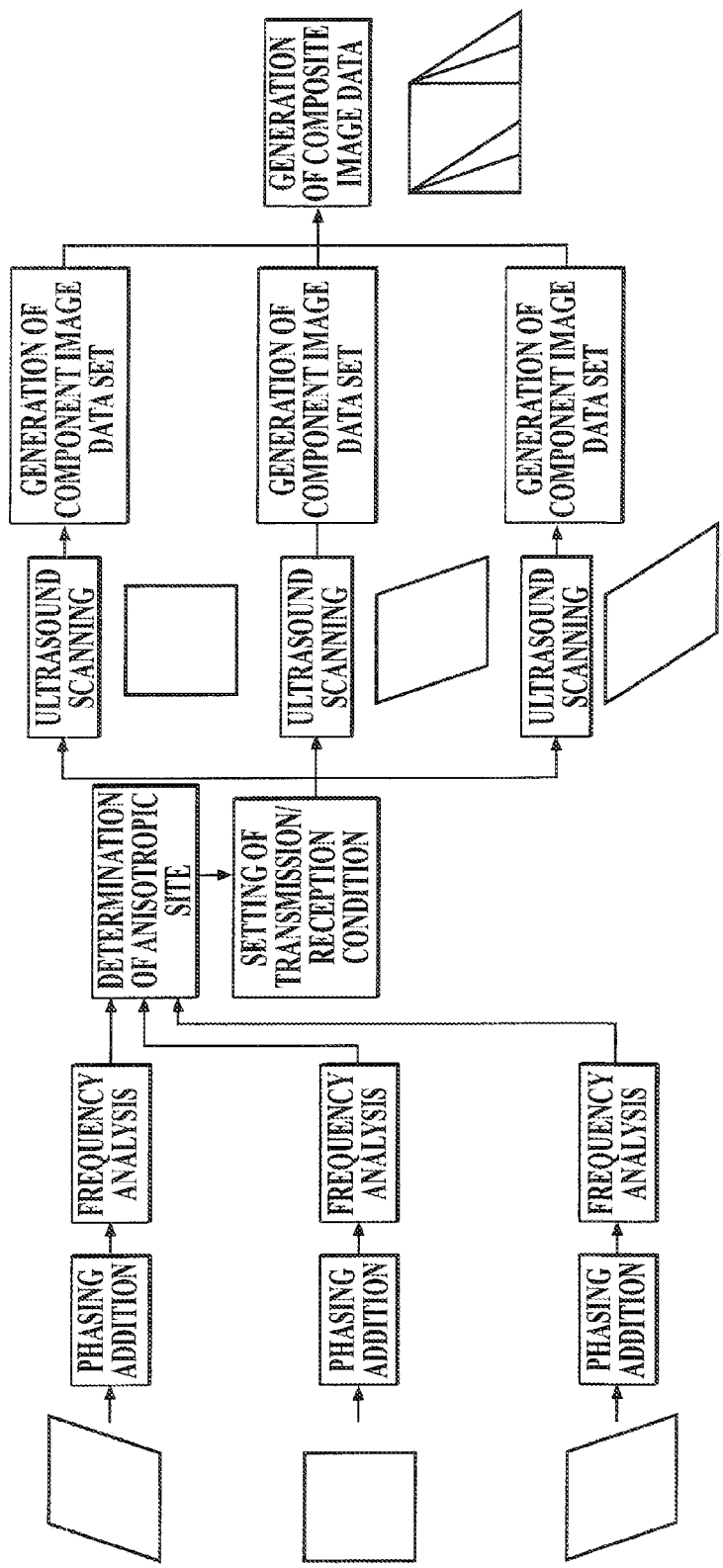
FIG. 28 is an explanatory diagram of a processing flow of the $14^{th}$ example of spatial compounding.

Next, the $14^{th}$ example of spatial compounding will be described with reference to FIG. 28.

In the $14^{th}$ example of spatial compounding, synthetic image data is generated in a manner as described below. The anisotropic site detection unit 16 performs frequency analysis based on sound ray data generated by the phasing addition circuit in the receiving unit 13 as described above in the $2^{nd}$ example. The anisotropic site detection unit 16 determines the position of the anisotropic site from the results of such frequency analysis. In such way, the anisotropic site detection unit 16 evaluates the anisotropic aspects of ultrasound wave reflection. According to the determined position of the anisotropic site, the anisotropic site detection unit 16 sets the transmission/reception conditions of ultrasound waves. Then, the transmitting unit 12 and the receiving unit 13 perform transmission and reception of ultrasound waves under the set transmission/reception conditions. The image processing unit 15 generates component image data sets according to receive signals of their respective scan regions obtained by the transmission and reception of ultrasound waves. The image processing unit 15 synthesizes the component image data sets of the scan regions generated as described above to generate synthetic image data.

Figure 29:
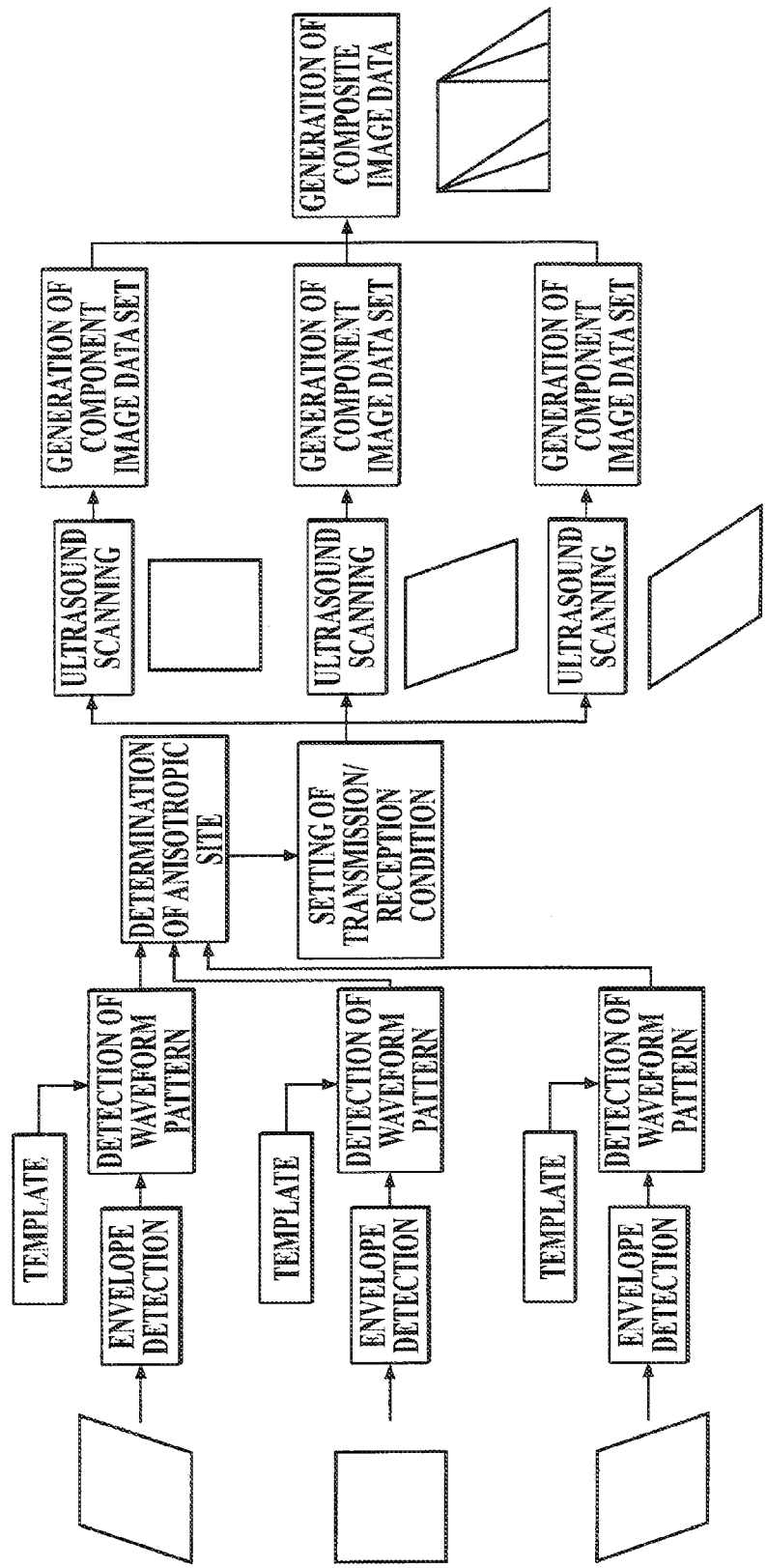
FIG. 29 is an explanatory diagram of a processing flow of the $15^{th}$ example of spatial compounding.

Next, the $15^{th}$ example of spatial compounding will be described with reference to FIG. 29.

In the 15th example of spatial compounding, synthetic image data is generated in a manner as described below. The anisotropic site detection unit 16 detects a waveform pattern based on sound ray data to which envelope detection is performed by the image generation unit 14 as described above in the 3rd example. The anisotropic site detection unit 16 determines the position of the anisotropic site using the detection results of such waveform pattern. In such way, the anisotropic site detection unit 16 evaluates the anisotropic aspects of ultrasound wave reflection. According to the determined position of the anisotropic site, the anisotropic site detection unit 16 sets the transmission/reception conditions of ultrasound waves. Then, the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 30:
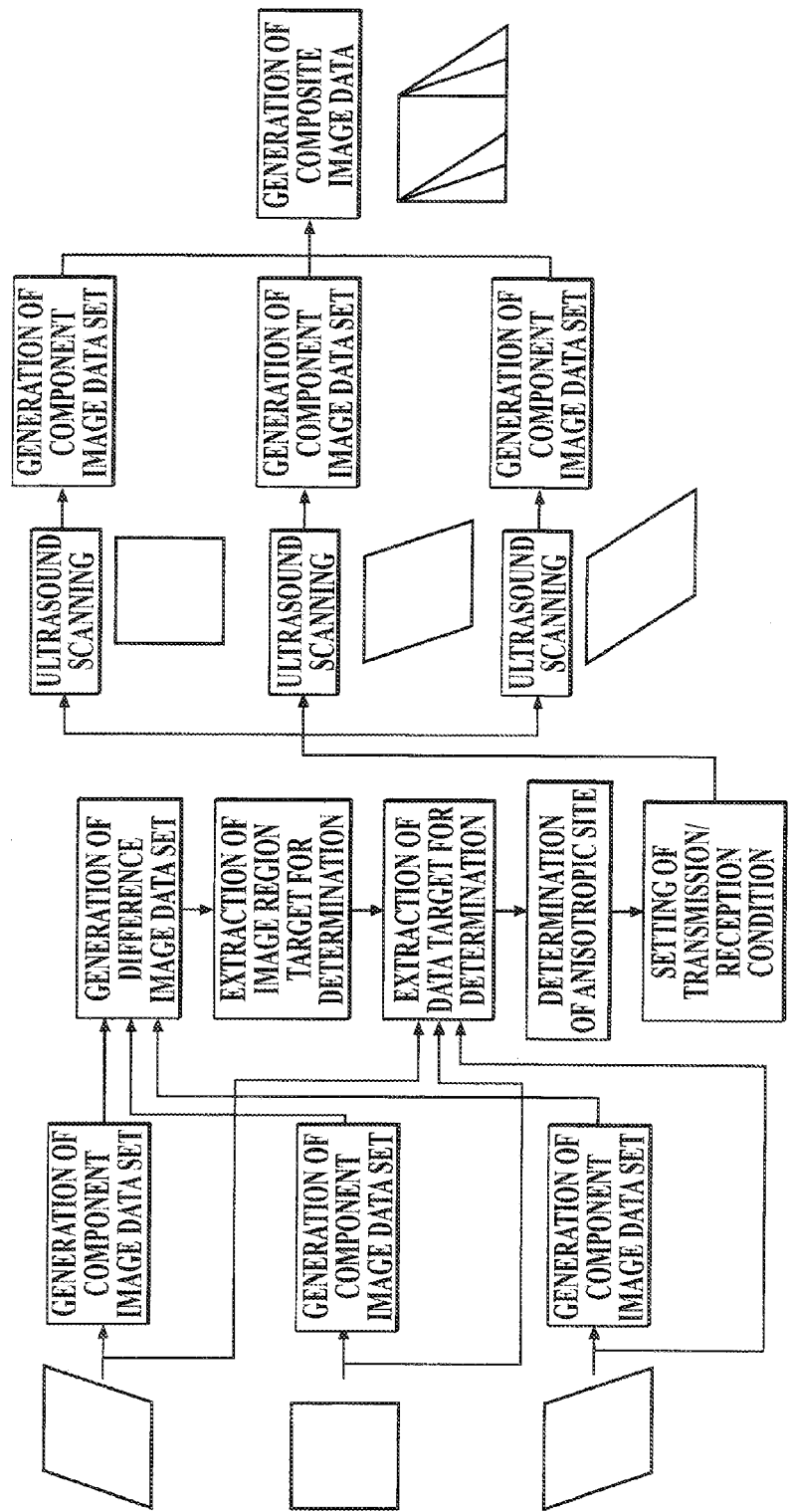
FIG. 30 is an explanatory diagram of a processing flow of the $16^{th}$ example of spatial compounding.

Next, the 16th example of spatial compounding will be described with reference to FIG. 30.

In the 16th example of spatial compounding, synthetic image data is generated in a manner as described below. The anisotropic site detection unit 16 generates a difference image data set which shows the luminescence difference between the component image data sets of the scan regions generated by the image processing unit 15 as described above in the 4th example. In the above generated difference image data, the anisotropic site detection unit 16 extracts an image region whose luminescence difference is equal to or greater than a predetermined threshold as the image region target for determination. The anisotropic site detection unit 16 extracts the sound ray data of the part corresponding to the extracted image region as the data target for determination. With respect to the extracted sound ray data, the anisotropic site detection unit 16 performs determination of the position of the anisotropic site (anisotropic site determination processing) described in the spatial compounding of the 13th to 15th examples. In such way, the anisotropic site detection unit 16 evaluates the anisotropic aspects of ultrasound wave reflection. According to the determination results of the position of the anisotropic site, the anisotropic site detection unit 16 sets the transmission/reception conditions of ultrasound waves. Then, the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 31:
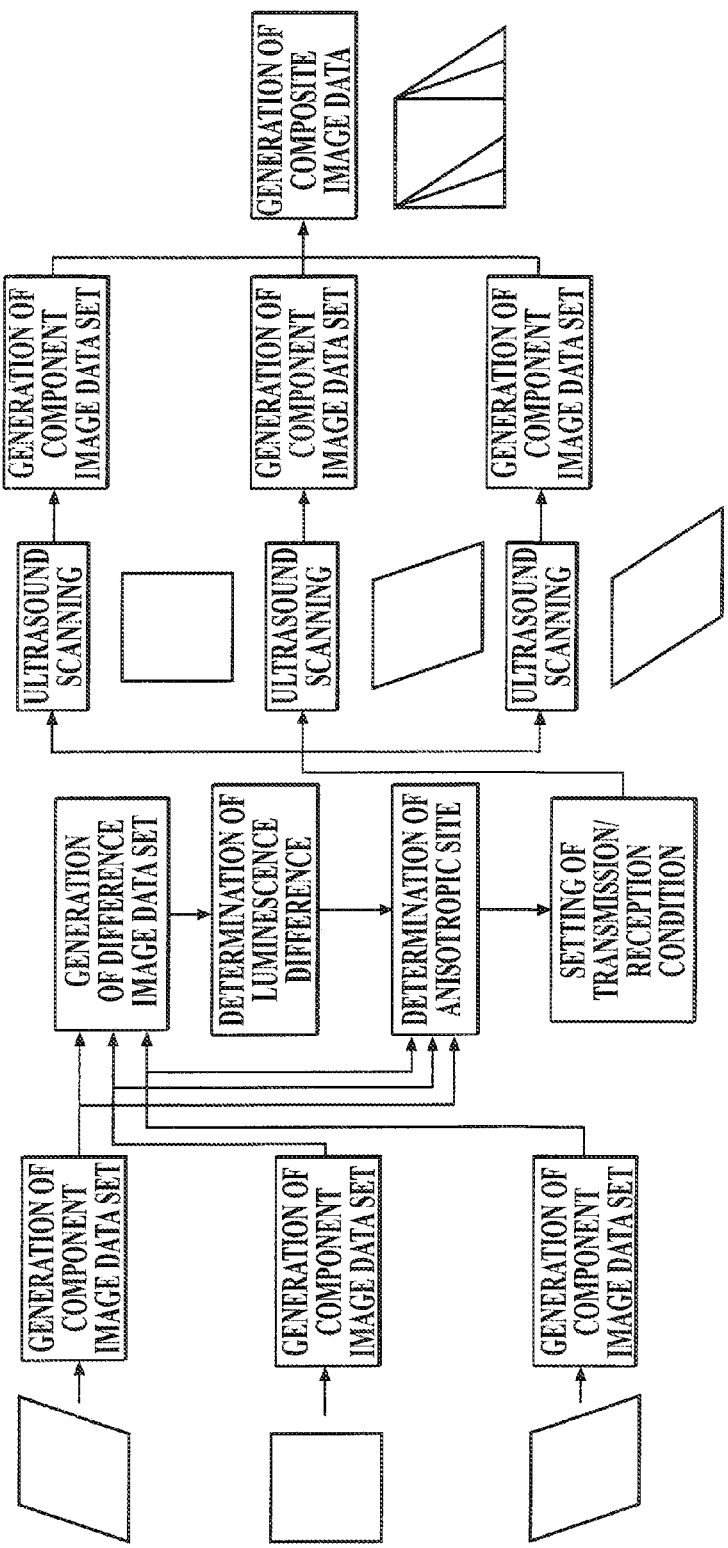
FIG. 31 is an explanatory diagram of a processing flow of the $17^{th}$ example of spatial compounding.

Next, the 17th example of spatial compounding will be described with reference to FIG. 31.

In the 17th example of spatial compounding, synthetic image data is generated in a manner as described below. The anisotropic site detection unit 16 generates difference image data sets which show the luminescence differences between the component image data sets of the scan regions generated by the image processing unit 15 as described above in the 5th example. The anisotropic site detection unit 16 performs the luminescence difference determination where a part where the luminescence difference is equal to or greater than a predetermined threshold is extracted in each of the difference image data sets obtained as described above. The anisotropic site detection unit 16 specifies the anisotropic site in the difference image data sets from which the parts where the luminescence difference is equal to or greater than the predetermined threshold are extracted and further specifies the difference image data set having the greatest luminescence difference at the part corresponding to the anisotropic site. The anisotropic site detection unit 16 determines the component image data set having the greatest luminescence at the region corresponding to the anisotropic site among the component image data sets used for generating the difference image data set having the greatest luminescence difference at the part corresponding to the anisotropic site. In such way, the anisotropic site detection unit 16 evaluates the anisotropic aspects of ultrasound wave reflection. Thereby, the scan region which best visualizes the anisotropic site is specified. According to the determination result, the anisotropic site detection unit 16 sets the transmission/reception conditions of ultrasound waves. Then the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 32:
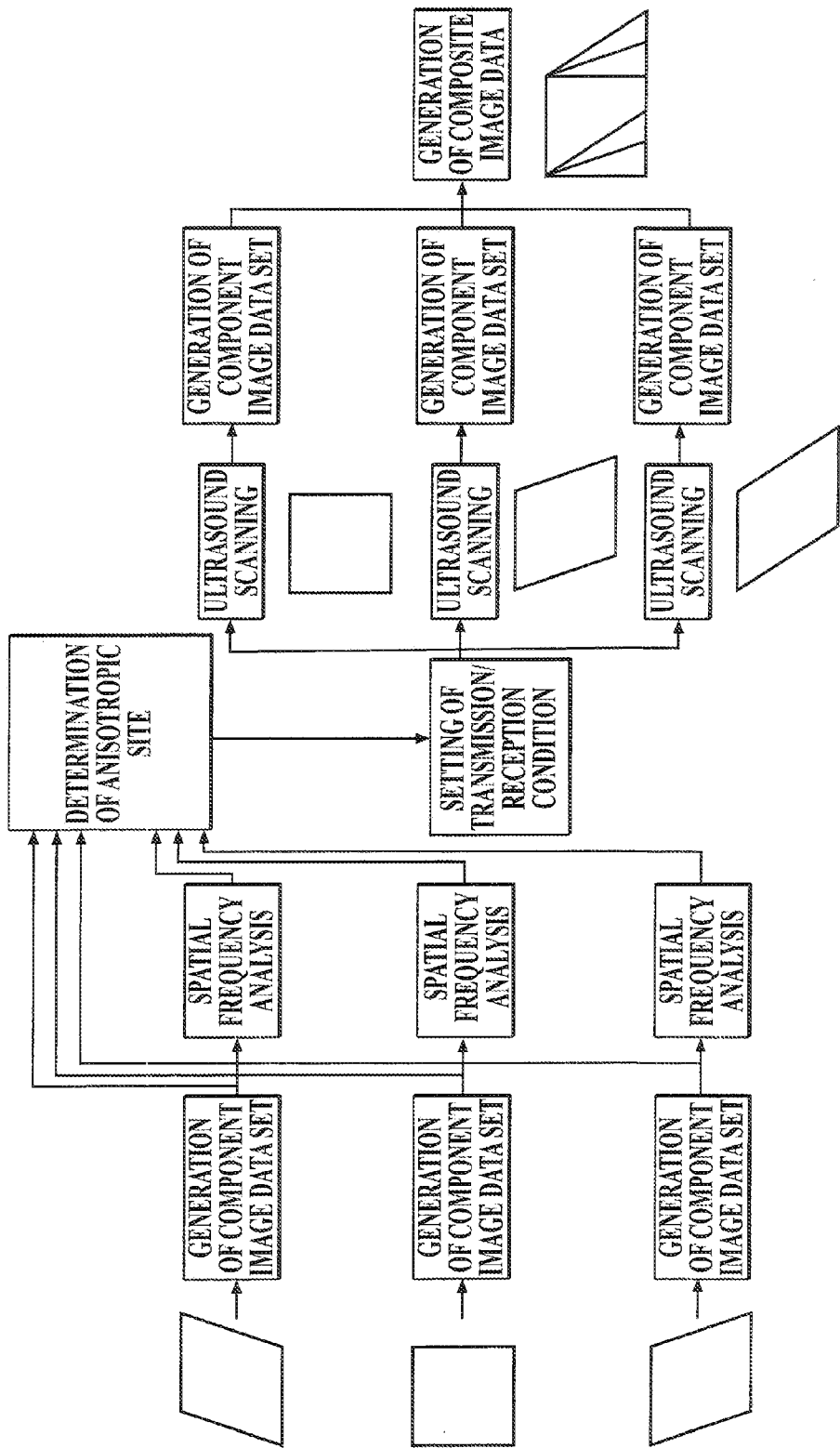
FIG. 32 is an explanatory diagram of a processing flow of the $18^{th}$ example of spatial compounding.

Next, the 18th example of spatial compounding will be described with reference to FIG. 32.

In the 18th example of spatial compounding, synthetic image data is generated in a manner as described below. With respect to the component image data sets of the scan regions generated by the image processing unit 15, the anisotropic site detection unit 16 analyzes the periodicity of each component image data set by performing spatial frequency analysis as described above in the 6th example. The anisotropic site detection unit 16 specifies the position of the anisotropic site by detecting that a specific pattern is included in the analysis results. The anisotropic site detection unit 16 determines a component image data set having a great luminescence at the part corresponding to the anisotropic site among the component image data sets of scan regions generated by the image processing unit 15. In such way, the anisotropic site detection unit 16 evaluates the anisotropic aspects of ultrasound wave reflection. Thereby, the scan region which best visualizes the anisotropic site is specified. According to the determination results, the anisotropic site detection unit 16 sets the transmission/reception condition of ultrasound waves. Then the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 33:
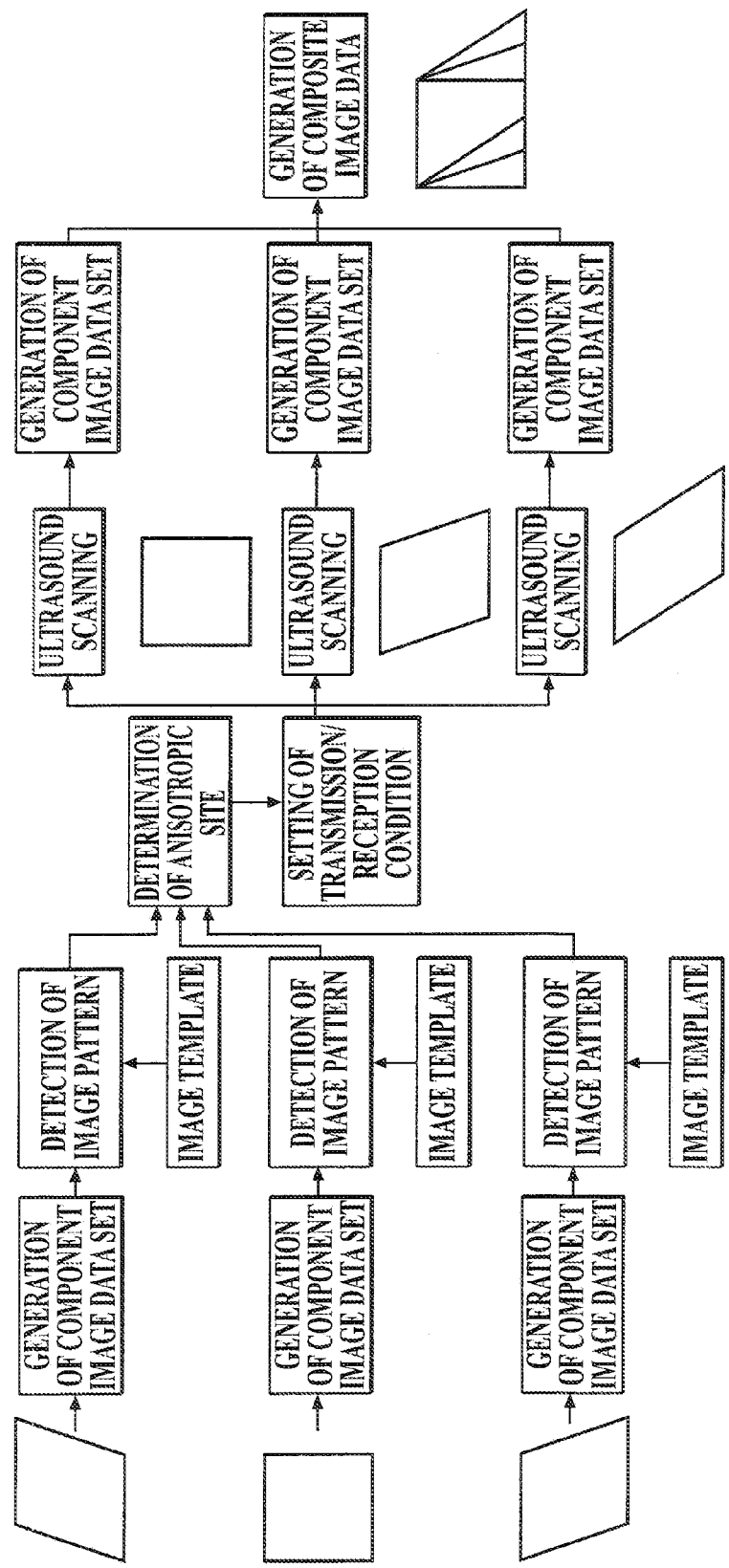
FIG. 33 is an explanatory diagram of a processing flow of the $19^{th}$ example of spatial compounding.

Next, the 19th example of spatial compounding will be described with reference to FIG. 33.

In the 19th example of spatial compounding, synthetic image data is generated in a manner as described below. With respect to the component image data sets of the scan regions generated by the image processing unit 15, the anisotropic site detection unit 16 detects an image patter in each of the component image data sets as describe above in the 7$^{th}$ example. The anisotropic site detection unit 16 determines the position of the anisotropic site using the detection results of the image pattern. Then, the anisotropic site detection unit 16 determines the component image data set having the greatest luminescence at the part corresponding to the anisotropic site among the component image data sets of the scan regions generated by the image processing unit 15. In such way, the anisotropic site detection unit 16 evaluates the anisotropic aspects of ultrasound wave reflection. Thereby, the scan region which best visualizes the anisotropic site is specified. According to the determination results, the anisotropic site detection unit 16 sets the transmission/reception condition of ultrasound waves. Then the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 34:
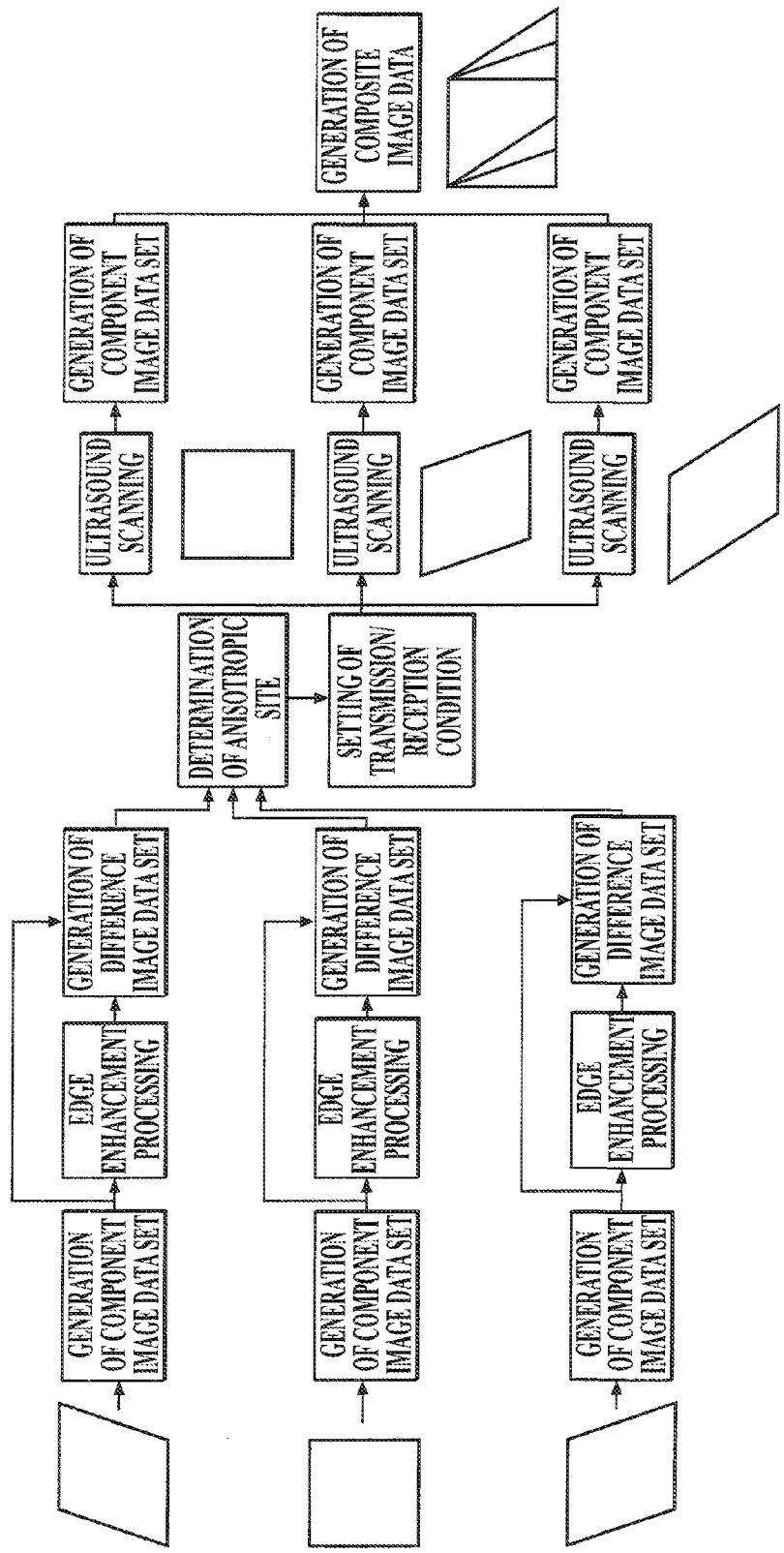
FIG. 34 is an explanatory diagram of a processing flow of the $20^{th}$ example of spatial compounding.

Next, the 20$^{th}$ example of spatial compounding will be described with reference to FIG. 34.

In the 20$^{th}$ example of spatial compounding, synthetic image data is generated in a manner as described below. With respect to each of the component image data sets of the scan regions generated by the image processing unit 15, the anisotropic site detection unit 16 performs edge enhancement processing as described above in the 8$^{th}$ example. The anisotropic site detection unit 16 generates difference image data sets showing luminescence differences between the component image data sets on which edge enhancement processing is performed and their corresponding component image data sets before edge enhancement processing. In such way, difference image data sets in which only the edge parts are extracted are generated. The anisotropic site detection unit 16 specified the position of the anisotropic site in each of the difference image data sets. The anisotropic site detection unit 16 determines the component image data set having the greatest luminescence at the part corresponding to the anisotropic site among the component image data sets of the scan regions generated by the image processing unit 15. In such way the anisotropic site detection unit 16 evaluates the anisotropic aspects of ultrasound wave reflection. Thereby, the scan region best visualizes the anisotropic site is specified. In a case where edge parts which constitute linear parts or curved parts exceeding a certain length are included in the difference image data sets from which the edge parts are extracted, the content rate thereof may be calculated in each of the difference image data sets and the scan region which best visualizes the anisotropic site may be specified by comparing the calculated content rates of the difference image data sets. According to the determination results, the anisotropic site detection unit 16 sets the transmission/reception conditions of ultrasound waves. Then, the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 35:
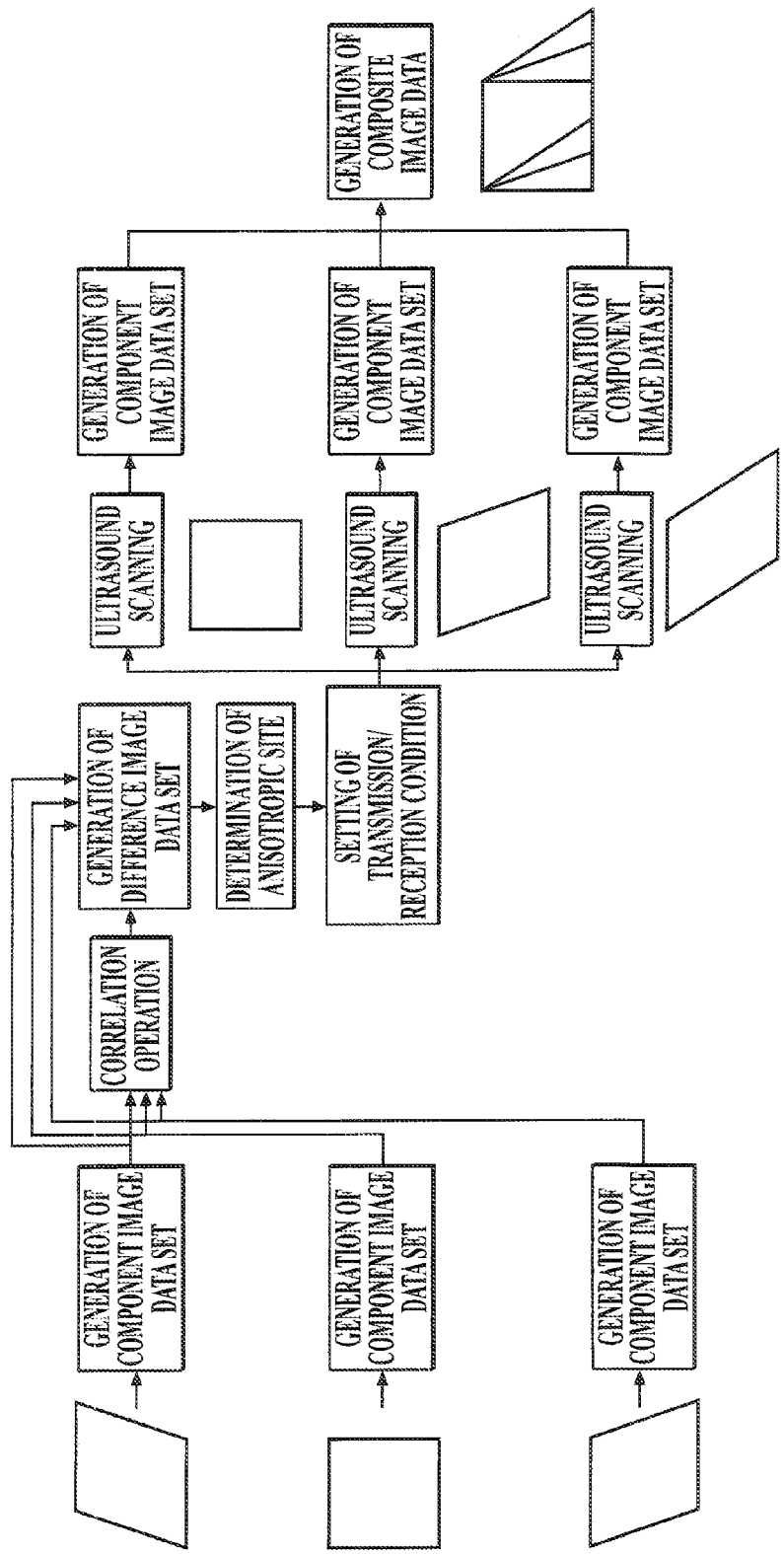
FIG. 35 is an explanatory diagram of a processing flow of the $21^{st}$ example of spatial compounding.

Next, the 21$^{st}$ example of spatial compounding will be described with reference to FIG. 35.

In the 21$^{st}$ example of spatial compounding, synthetic image data is generated in a manner as described below. The anisotropic site detection unit 16 carries out an operation to obtain the correlation coefficient between the component image data sets of the scan regions generated by the image processing unit 15 as described above in the 9$^{th}$ example and specifies whether the anisotropic site is included in the component image data sets from the results. If the anisotropic site detection unit 16 determines that the anisotropic site is included in the component image data sets, the anisotropic site detection unit 16 generates difference image data sets which show luminescence differences between the component image data sets. Difference image data sets are generates for all of the combinations of two component image data sets. The anisotropic site detection unit 16 specifies the difference image data set having the greatest luminescence difference at the position corresponding to the anisotropic site among the above generated difference image data sets. The anisotropic site detection unit 16 specifies the component image data set having the greatest luminescence at the region corresponding to the anisotropic site among the component image data sets used to generated the difference image data set having the greatest luminescence difference at the part corresponding to the anisotropic site. In such way, the anisotropic site detection unit 16 evaluates the anisotropic aspects of ultrasound wave reflection. Thereby, the scan region which best visualizes the anisotropic site is specified. According to the determination results, the anisotropic site detection unit 16 sets the transmission/reception condition of ultrasound waves. Then the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 36:
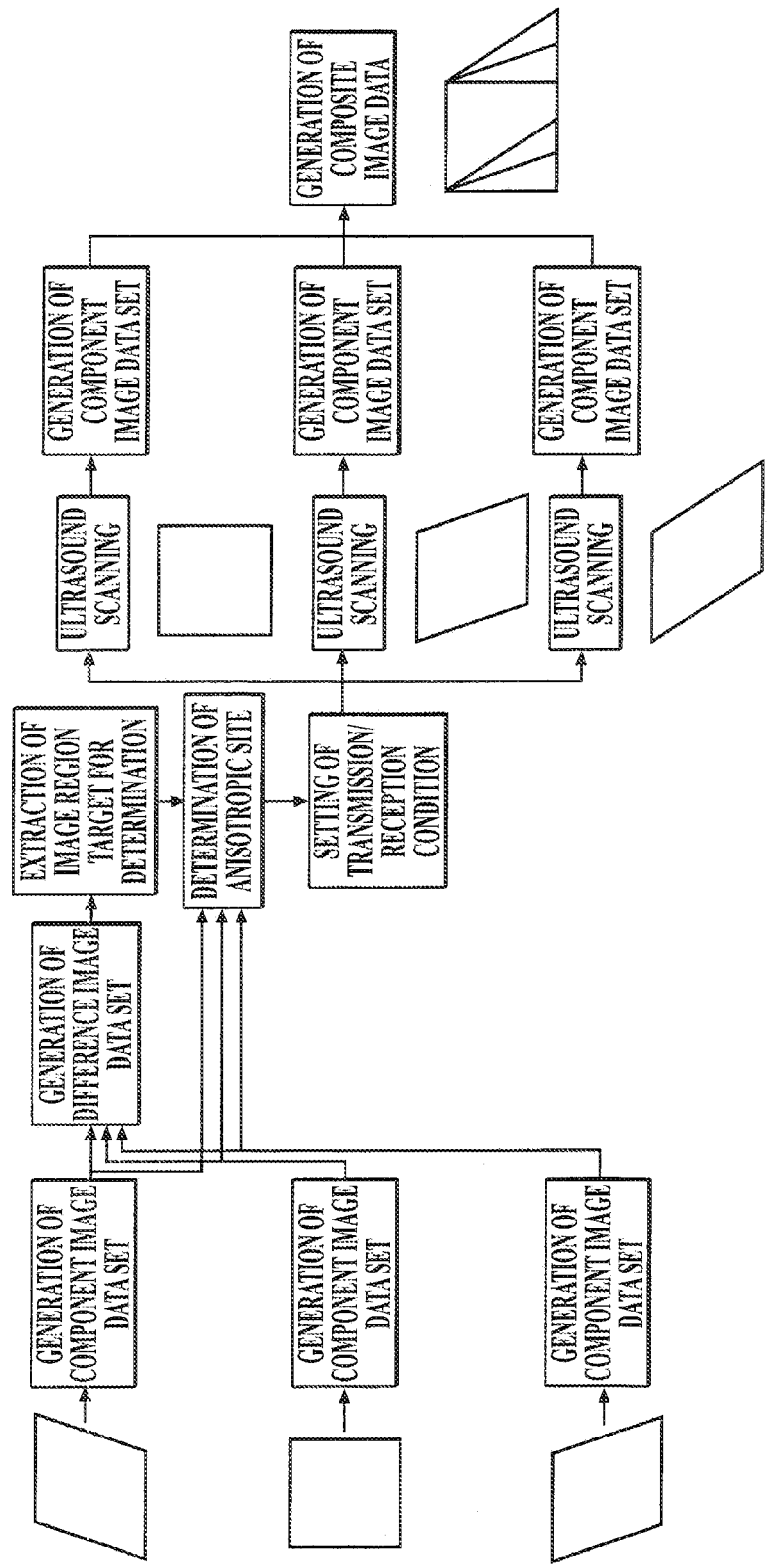
FIG. 36 is an explanatory diagram of a processing flow of the $22^{nd}$ example of spatial compounding.

Next, the 22$^{nd}$ example of spatial compounding will be described with reference to FIG. 36.

In the 22$^{nd}$ example of spatial compounding, synthetic image data is generated in a manner as described below. The anisotropic site detection unit 16 generates difference image data sets which show luminescence difference between the component image data sets of the scan regions generated by the image processing unit 15 as described above in the 10$^{th}$ example. Among the difference image data sets obtained in such way, the anisotropic site detection unit 16 extracts the image region whose luminescence difference equal to or greater than a predetermined threshold as the image region target for determination. With respect to the component image data sets of the part corresponding to the extracted image region, the anisotropic site detection unit 16 performs determination of the position of the anisotropic site (anisotropic site determination processing) described in the spatial compounding of the 17$^{th}$ to 21$^{st}$ examples. In such way, the anisotropic site detection unit 16 evaluates the anisotropic aspects of ultrasound wave reflection. According to the determination results of the position of the anisotropic site, the anisotropic site detection unit 16 sets the transmission/reception conditions of ultrasound waves. Then the transmitting unit 12 and the receiving unit 13 perform transmission and reception of ultrasound waves under the set transmission/reception conditions. The image processing unit 15 generates component image data sets according to the receive signals of their respective scan regions obtained by the transmission and reception of ultrasound waves. The image processing unit 15 synthesizes the component image data sets of the scan regions generated as described above to generate synthetic image data.

Figure 37:
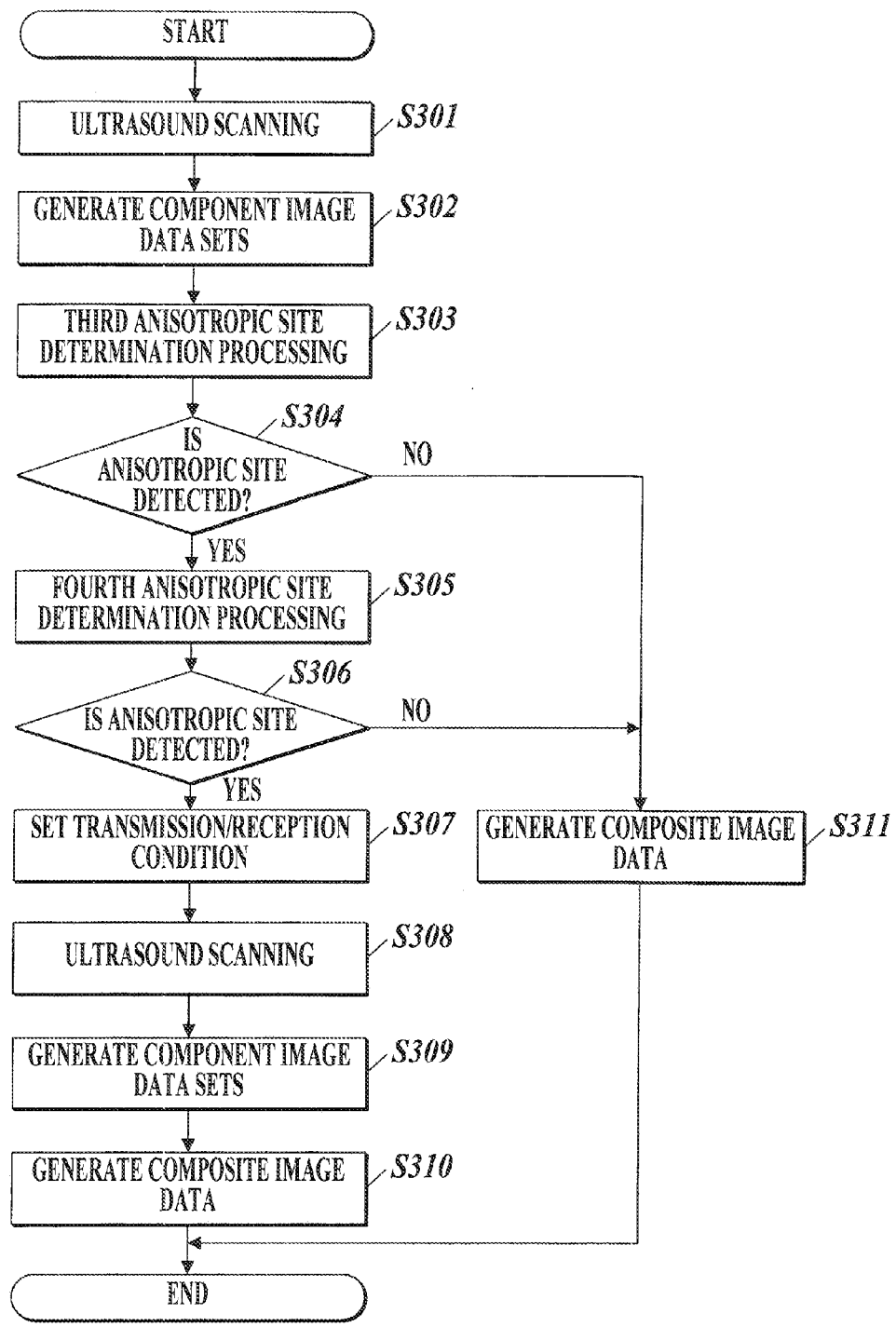
FIG. 37 is a flowchart for explaining a processing flow of the $23^{rd}$ example of spatial compounding.

Next, the $23^{rd}$ example of spatial compounding will be described with reference to FIG. 37.

In the $23^{rd}$ example of spatial compounding, synthetic image data is generated in a manner as described below. The control unit 19 controls the transmitting unit 12 and the receiving unit 13 to perform ultrasound scanning with respect to each of the plurality of scan regions having different steering angles (step S301). The control unit 19 controls the image generation unit 14 and the image processing unit 15 to generate component image data sets respectively for the scan regions according to the receive signals obtained by performed ultrasound scanning as described above (step S302). The control unit 19 controls the anisotropic site detection unit 16 to perform determination of the position of the anisotropic site (the third anisotropic site determination processing) described in either of the spatial compounding of the $13^{th}$ to $15^{th}$ examples and of the $17^{th}$ to $21^{st}$ examples (step S303). The control unit 19 determines whether the anisotropic site is detected as a result of performing the third anisotropic site determination processing (step S304). If the control unit 19 determines that the anisotropic site is detection (step S304; Y), the control unit 19 controls the anisotropic site detection unit 16 to perform the determination of the position of the anisotropic site (the fourth anisotropic site determination processing) described in either of the spatial compounding in the $13^{th}$ to $15^{th}$ examples and the $17^{th}$ to $21^{st}$ examples, different from the one used in the third anisotropic site determination processing (step S305). The control unit 19 determines whether the anisotropic site is detection as a result of the fourth anisotropic site determination processing (step S306). If the control unit 19 determines that the anisotropic site is detected (step S306; Y), the control unit 19 controls the anisotropic site detection unit 16 to evaluate the anisotropic aspects of ultrasound wave reflection by specifying the component image data set of the scan region which best visualizes the anisotropic site and sets the transmission/reception condition of ultrasound waves on the bases of the evaluation result (step S307). The control unit 19 controls the transmitting unit 12 and the receiving unit 13 to perform ultrasound scanning with respect to the plurality of scan regions having different steering angles under the transmission/reception condition of ultrasound waves set in step S307 (step S308). The control unit 19 controls the image generation unit 14 and the image processing unit 15 to respectively generate component image data sets of the scan regions again according to the receive signals obtained by performing ultrasound scanning as described above (step S309). The control unit 19 controls the image processing unit 15 to composite the component image data sets of the scan regions which are generated for the second time and generates synthetic image data (step S310), and hereby ends the process. On the other hand, if the control unit 19 does not determine that the anisotropic site is detected in step S304 or in step S306 (step S304; N, step S306; N), the control unit 19 controls the image processing unit 15 to synthesize the component image data sets of the scan regions obtained in step S302 and generate synthetic image data (step S311). According to the $23^{rd}$ example, detection accuracy of the position of the anisotropic site can be improved and the appropriate spatial compounding can be performed.

In the above described $20^{th}$ to $23^{rd}$ examples of spatial compounding, if the receive F value is set to 0.8 or smaller after the transmission/reception conditions of ultrasound waves are set, the anisotropic site appears more clearly, and therefore, this setting is preferred. However, the setting is not limited to such setting. Further, if the transmission F value with respect to the receive F value is set to 3 or more, the anisotropic site appears even clearer, and therefore, this setting is preferred, and it is more preferable if the transmission F value is set between 3.0 to 3.5. However, the setting is not limited to such settings.

The determination method of the position of the anisotropic site is not limited to what is described above. For example, morphological operation can be applied to determine the position of the anisotropic site.

As described above, according to the embodiment, the transmitting unit 12 and the receiving unit 13 drive a plurality of transducers 2a and repeat transmission and reception of ultrasound waves in a plurality of directions, the directions being different from one another, to perform ultrasound scanning for a plurality of times in such manner that a part of or the entire scan regions overlap. The image processing unit 15 generates a plurality of component image data sets from the receive signals obtained as a result of ultrasound scanning performed by the transmitting unit 12 and the receiving unit 13. On the basis of at least either of the ultrasound image data and the receive signals, the anisotropic site detection unit 16 evaluates the anisotropic aspects of ultrasound wave reflection in a subject. According to the evaluation results of the anisotropic site detection unit 16, the image processing unit 15 generates synthetic image data where the plurality of component image data sets are synthesizes. As a result, the synthetic image data can be generated adaptively by the spatial compounding according to the evaluation results of the anisotropic aspects of ultrasound wave reflection. Therefore, the anisotropic site can be visualized clearly.

Further, according to the embodiment, the image processing unit 15 generates the synthetic image data by synthesizing the plurality of component image data sets by the method according to the evaluation results of the anisotropic site detection unit 16. As a result, by adaptively changing the synthesis method of the ultrasound image data when generating the synthetic image data by the spatial compounding, the anisotropic site can be visualized clearly.

According to the $12^{th}$ example of spatial compounding, the anisotropic site detection unit 16 detects the anisotropic site indicating anisotropic aspects of ultrasound wave reflection. The image processing unit 15 applies different synthesis methods for the part where the anisotropic site is detected by the anisotropic site detection unit 16 and the other part when generating the synthetic image data. As a result, the best suited images can be obtained both at the anisotropic site and the other part.

According to the $1^{st}$ to $12^{th}$ examples of spatial compounding, because the depth rate of the receive focal point with respect to the aperture of the receive signals to be used for performing phasing addition, the aperture being configured of transducers 2a, is set to 0.8 or smaller, more reflection ultrasound waves reflected off the anisotropic site can be received and the anisotropic site can be visualized more clearer.

According to the $1^{st}$ to $12^{th}$ examples of spatial compounding, because the transmission F value with respect to the reception F value is set to 3 or greater, more reflection ultrasound waves reflected off the anisotropic site can be received and the anisotropic site can be visualized more clearer.

According to the embodiment, the transmitting unit 12 and the receiving unit 13 set the transmission/reception conditions for transmitting and receiving ultrasound waves according to the evaluation result of the anisotropic site detection unit 16 and perform ultrasound scanning under the set transmission/reception conditions. The image processing unit 15 generates the synthetic image data where the plurality of component image data sets generated from the receive signals obtained as the result of performing ultrasound scanning under the set transmission/reception conditions are synthesizes. As a result, by adaptively changing the transmission/reception conditions of ultrasound waves when generating the synthetic image data by spatial compounding, the anisotropic site can be visualizes clearly.

According to the $13^{th}$ to $23^{rd}$ examples of spatial compounding, the transmitting unit 12 and the receiving unit 13 set the directions to which ultrasound waves are transmitted as the transmission/reception condition to be set according to the evaluation results of the anisotropic site detection unit 16. As a result, the anisotropic site can be visualized clearer.

According to the $13^{th}$ to $23^{rd}$ examples of spatial compounding, the transmitting unit 12 and the receiving unit 13 set the number of scan regions subject to ultrasound scanning as the transmission/reception conditions to be set according to the evaluation results of the anisotropic site detection unit 16. As a result, the anisotropic site can be visualized clearer.

According to the $13^{th}$ to $23^{rd}$ examples of spatial compounding, the transmitting unit 12 and the receiving unit 13 set the transducers 2a of receive signals to be used for performing phasing addition as the transmission/reception conditions to be set according to the evaluation results of the anisotropic site detection unit 16. As a result, the anisotropic site can be visualized clearer.

According to the $13^{th}$ to $23^{rd}$ examples of spatial compounding, because the depth rate of the receive focal point with respect to the aperture formed of the transducers 2a of the receive signals to be used for performing phasing addition after the setting of the transmission/reception conditions is set to 0.8 or smaller, more reflection ultrasound waves reflected off the anisotropic site can be received and the anisotropic site can be visualized clearer.

According to the $13^{th}$ to $23^{rd}$ examples of spatial compounding, because the rate of transmission F value with respect to the receive F value after the setting of the transmission/reception conditions is set to 3 or more, more reflection ultrasound waves reflected off the anisotropic site can be received and the anisotropic site can be visualized clearer.

According to the $4^{th}$, $10^{th}$, $16^{th}$ and $22^{nd}$ examples of spatial compounding, the anisotropic site detection unit 16 calculates the luminescence difference between the overlapping parts in the scan regions of the two component image data sets among the plurality of component image data sets and evaluates the anisotropic aspects of the part where the calculated luminescence difference is equal to or greater than a predetermined threshold. As a result, the range for anisotropic aspect evaluation can be narrowed down and thus, accuracy of anisotropic aspect evaluation can be improved and processing efficiency of anisotropic aspect evaluation can be improved.

According to the $1^{st}$ and $13^{th}$ examples of spatial compounding, the anisotropic site detection unit 16 calculates the coherence factors according to the receive signals of transducers before performing phase addition, the receive signals being obtained by the plurality of transducers 2a, and evaluates the anisotropic aspects based on the calculated coherence factors. As a result, the anisotropic aspect evaluation can be carried out by using the reduction in signal correlativity between the receive signals of the transducers due to the anisotropic reflection characteristic of the anisotropic site. Therefore, the anisotropic site can be visualized clearer.

According to the $2^{nd}$ and $14^{th}$ examples of spatial compounding, the anisotropic site detection unit 16 evaluates the anisotropic aspects by detecting that a specified frequency component is included continuously in the receive signals. As a result, the anisotropic aspect evaluation can be carried out by detecting the frequency component corresponding to the anisotropic site. Therefore, the anisotropic site can be visualized clearly.

According to the $3^{rd}$ and $15^{th}$ examples of spatial compounding, the anisotropic site detection unit 16 evaluates the anisotropic aspects by detecting that the predetermined waveform pattern is included in the waveform of the receive signals to which envelope detection is performed. As a result, the anisotropic aspects evaluation can be carried out by detecting the enveloped waveform pattern corresponding to the anisotropic site. Therefore, the anisotropic site can be visualized clearly.

According to the $5^{th}$ and $17^{th}$ examples of spatial compounding, the anisotropic site detection unit 16 calculates the luminescence differences at the parts where the scan regions overlap in the plurality of component image data sets and carries out the anisotropic aspect evaluation based on the calculated levels of luminescence differences. As a result, the anisotropic aspect evaluation can be carried out by detecting the region corresponding to the anisotropic site in relevance to luminescence difference. Therefore, the anisotropic site can be visualized clearly.

According to the $6^{th}$ and $18^{th}$ examples of spatial compounding, the anisotropic site detection unit 16 performs spatial frequency analysis with respect to the component image data sets and evaluates the anisotropic aspects based on the spatial frequency analysis results. As a result, the anisotropic aspect evaluation can be carried out by detecting the frequency component corresponding to the anisotropic site. Therefore, the anisotropic site can be visualized clearly.

According to the $7^{th}$ and $19^{th}$ examples of spatial compounding, the anisotropic site detection unit 16 evaluates the anisotropic aspects by detecting that the predetermined anisotropic site image pattern is included in the component image data sets. As a result, the anisotropic aspect evaluation can be carried out by detecting the image pattern corresponding to the anisotropic site. Therefore, the anisotropic site can be visualized clearly.

According to the $8^{th}$ and $20^{th}$ examples of spatial compounding, the anisotropic site detection unit 16 performs the edge detection with respect to the component image data sets. As a result of the edge detection, the anisotropic site detection unit 16 evaluates the anisotropic aspects according to the fact that the edges of a predetermined length are continuously extracted. As a result, the anisotropic site which is derived of a fibrous tissue can be detected by the continuity of the edges. Therefore, the anisotropic site can be visualized clearly.

According to the $9^{th}$ and $21^{st}$ examples of spatial compounding, the anisotropic site detection unit 16 calculates the correlation coefficient of two component image data sets among the plurality of component image data sets by a predetermined correlation operation and evaluates the anisotropic aspect based on the calculated correlation coefficient. As a result, the anisotropic aspect evaluation can be carried out by correlation function. Therefore, the anisotropic site can be visualized clearly.

According to the 11$^{th}$ and 23$^{rd}$ examples of spatial compounding, the anisotropic site detection unit 16 executes a plurality of types of evaluation method for evaluating the anisotropic aspects. The image processing unit 15 generates synthetic image data according to the evaluation results of the anisotropic aspects under the condition that the anisotropic aspect evaluation is carried out by at least by a predetermined number of evaluation methods or more among the plurality of types of evaluation methods. As a result, evaluation accuracy of the anisotropic aspect can be improved.

According to the embodiment, the transmitting unit 12 and the receiving unit 13 set the transmission/reception condition for transmitting and receiving ultrasound waves according to the evaluation results of the anisotropic aspects of the anisotropic site detection unit 16 and perform transmission of ultrasound waves under the set transmission/reception condition. The image processing unit 15 generates the synthetic image data by synthesizing the plurality of component image data sets generated from the receive signals obtained as the result of performing ultrasound scanning under the set transmission/reception condition by the synthesis method according to the anisotropic aspect evaluation results of the anisotropic site detection unit 16. As a result, visualization of the anisotropic site can be synergistically clearer.

The above descriptions of the embodiment of the present invention are merely examples of the ultrasound diagnostic imaging apparatus according to the present invention and present invention is not limited to the examples. The detail configurations and detail operations of the functional parts which constitute the ultrasound diagnostic imaging apparatus can be changed arbitrarily.

In the embodiment, it is not necessary that all of the 1$^{st}$ to 23$^{rd}$ examples of spatial compounding are executable. It is sufficient that 1 or a plurality of the 1$^{st}$ to 23$^{rd}$ examples of spatial compounding can be executed.

In the embodiment, an example where a non-volatile memory such as a hard disk or a semiconductor is used as the computer readable medium for the programs according to the present invention is described. However, the present invention is not limited to such example. As other computer readable medium, a portable recording medium such as a CD-ROM can be applied. Further, as a medium for providing the programs according to the present invention via a communication circuit, a carrier wave can be applied.

Embodiment Example 1

Hereinafter, specific embodiment examples of the present invention will be described. However, the present invention is not limited to the examples.

By using the above described ultrasound diagnostic imaging apparatus, transmission and reception of ultrasound waves are performed with respect to the anterior talofibular ligament and its periphery and the ultrasound images which are displayed according to the synthetic image data obtained by performing the spatial compounding under the conditions described bellow (comparison examples 1 and 2, embodiment examples 1 to 25) are evaluated. The evaluation results are shown in the following tables 1 and 2.

In the evaluation of the ultrasound images, with respect to the anterior talofibular ligament portion, first, image luminosity evaluation where the rate of average image luminescent value of the anterior talofibular ligament region with respect to the average image luminescent value of the region excluding the actual anterior talofibular ligament is indicated in the evaluation of 11 levels which are 0 to 10 was performed. Evaluation values are as described bellow.

10: relative luminance value 130% or greater
9: relative luminance value not less than 110% and less than 130%
8: relative luminance value not less than 90% and less than 110%
7: relative luminance value not less than 75% and less than 90%
6: relative luminance value not less than 60% and less than 75%
5: relative luminance value not less than 50% and less than 60%
4: relative luminance value not less than 40% and less than 50%
3: relative luminance value not less than 30% and less than 40%
2: relative luminance value not less than 20% and less than 30%
1: relative luminance value not less than 10% and less than 20%
0: relative luminance value less than 10%

Secondly, visual evaluation was performed by total of 10 medical doctors and clinical technologists who work in the area of orthopedics. In such visual evaluation, evaluation points are obtained following the evaluation criteria described bellow and visibility evaluation of the anterior talofibular ligament is performed by obtaining the average of the obtained evaluation points (round off after the decimal point).

10: visibility similar to or greater than that of when facing a ligament, the visibility being perfect for grasping the condition
8: short of visibility similar to that of when facing a ligament, but the visibility is substantially enough for grasping the condition
6: less than the visibility similar to that of when facing a ligament, the visibility being at the level possible to grasp the condition
4: far less than the visibility similar to that of when facing a ligament, the visibility being at the level slightly difficult to grasp the condition
2: visibility being at the level that the existence of a ligament can be confirmed but difficult to grasp the condition
0: visibility being at the level that the existence of a ligament cannot be confirmed and very difficult to grasp the condition Further, in the evaluation of the ultrasound images, with respect to the region other than the anterior talofibular ligament, visual evaluation was performed by total of 10 medical doctors and clinical technologists who work in the area of orthopedics. In such visual evaluation, evaluation points are obtained following the evaluation criteria described bellow and visibility evaluation of the region other than the anterior talofibular ligament is performed by obtaining the average of the obtained evaluation points (round off after the decimal point).

10: perfect visibility for grasping tissue condition
8: substantially sufficient visibility for grasping tissue condition
6: visibility being not good but possible to grasp tissue condition 4: visibility being at the level difficult to grasp tissue condition 2: visibility being at the level very difficult to grasp tissue condition Comparison Example 1

In comparison example 1, only the component image data set corresponding to the scan region where the steering angle is 0° is obtained and the spatial compounding is not performed. The transmission F value is set to 3.5 (this also applies to comparison example 2 and embodiment examples 1 to 25). Further, the reception F value is set to 1.5 (this also applies to comparison example 2, embodiment examples 1 to 11, 13 to 21, 23 and 24).

Comparison Example 2

In comparison example 2, component image data sets corresponding to the scan regions having the steering angles of 0°, +10° and −10° are obtained and the spatial compounding is performed (this also applies to embodiment examples 1 to 25). Here, the synthesis rates of the component image data sets are equal.

Embodiment Example 1

In embodiment example 1, synthetic image data is generated by performing the spatial compounding of the $1^{st}$ example described above. When performing the spatial compounding, the component image data set corresponding to the scan region having the steering angle of 0° is weighted by 40%, the component image data set corresponding to the scan region having the steering angle of +10° is weighted by 20% and the component image data set corresponding to the scan region having the steering angle of −10° is weighted by 40% (this also applies to embodiment examples 2 to 9, 11 and 12).

Embodiment Example 2

In embodiment example 2, synthetic image data is generates by performing the spatial compounding of the $2^{nd}$ example described above.

Embodiment Example 3

In embodiment example 3, synthetic image data is generated by performing the spatial compounding of the $3^{rd}$ example described above.

Embodiment Example 4

In embodiment example 4, synthetic image data is generated by performing the spatial compounding of the $5^{th}$ example described above.

Embodiment Example 5

In embodiment example 5, synthetic image data is generated by performing the spatial compounding of the $6^{th}$ example described above.

Embodiment Example 6

In embodiment example 6, synthetic image data is generated by performing the spatial compounding of example 7 described above.

Embodiment Example 7

In embodiment example 7, synthetic image data is generated by performing the spatial compounding of the $8^{th}$ example described above.

Embodiment Example 8

In embodiment example 8, synthetic image data is generated by performing the spatial compounding of the $9^{th}$ example described above.

Embodiment Example 9

In embodiment example 9, the spatial compounding of the $7^{th}$ example described above is performed by applying the spatial compounding of the $10^{th}$ example described above to generate synthetic image data. In other words, the spatial compounding of the $10^{th}$ example described above is performed to extract an image region target for determination and the component image data sets of the part corresponding to the extracted image region are extracted. Then, the spatial compounding of the $7^{th}$ example described above is applied to the extracted component image data sets to generate the synthetic image data.

Embodiment Example 10

In embodiment example 10, the spatial compounding of the $11^{th}$ example described above is performed to generate synthetic image data. Here, as the first anisotropic site determination processing, the determination of the position of the anisotropic site by the spatial compounding described in the $5^{th}$ example is performed and as the second anisotropic site determination processing, the determination of the position of the anisotropic site by the spatial compounding shown described in the $8^{th}$ example is performed. Further, when performing the spatial compounding, the component image data set corresponding to the scan region having the steering angle 0° is weighted by 50%, the component image data set corresponding to the scan region having the steering angle +10° is weighted by 10% and the component image data set corresponding to the scan region having the steering angle −10° is weighted by 40%.

Embodiment Example 11

In embodiment example 11, the spatial compounding of the $12^{th}$ example described above is performed to generate synthetic image data. Here, as the anisotropic site determination processing, the determination of the position of the anisotropic site of the spatial compounding described in the $5^{th}$ example is performed. Then, edge enhancement processing is performed with respect to the anisotropic site region in the component image data set corresponding to the scan region having the steering angle −10°.

Embodiment Example 12

In embodiment example 12, the spatial compounding of the $5^{th}$ example described above is performed to generate synthetic image data. At this time, the reception F value is set to 0.8.

Embodiment Example 13

In embodiment example 13, the spatial compounding of the 13$^{th}$ example described above is performed to generate synthetic image data. After changing the transmission/reception conditions, component image data sets corresponding to the scan regions having steering angles 0°, −20° and −10° are respectively obtained and the spatial compounding is performed (this also applies to embodiment examples 14 to 20, 24 and 25). At this time, the synthesis rates of the component image data sets are equal (this also applies to embodiment examples 14 to 22).

Embodiment Example 14

In embodiment example 14, the spatial compounding of the 14$^{th}$ example described above is performed to generate synthetic image data.

Embodiment Example 15

In embodiment example 15, the spatial compounding of the 15$^{th}$ example described above is performed to generate synthetic image data.

Embodiment Example 16

In embodiment example 16, the spatial compounding of the 17$^{th}$ example described above is performed to generate synthetic image data.

Embodiment Example 17

In embodiment example 17, the spatial compounding of the 18$^{th}$ example described above is performed to generate synthetic image data.

Embodiment Example 18

In embodiment example 18, the spatial compounding of the 19$^{th}$ example described above is performed to generate synthetic image data.

Embodiment Example 19

In embodiment example 19, the spatial compounding of the 20$^{th}$ example described above is performed to generate synthetic image data.

Embodiment Example 20

In embodiment example 20, the spatial compounding of the 21$^{st}$ example described above is performed to generate synthetic image data.

Embodiment Example 21

In embodiment example 21, the spatial compounding of the 23$^{rd}$ example described above is performed to generate synthetic image data. At this time, the following processing is performed as the third anisotropic site determination processing. That is, the determination of the position of the anisotropic site of the spatial compounding described in the 16$^{th}$ example described above is performed. In particular, the spatial compounding of the 16$^{th}$ example described above is performed to extract an image region target for determination and the sound ray data of this corresponding part is extracted. Then, with respect to the extraction sound ray data, the determination of the position of the anisotropic site of the spatial compounding described in the 14$^{th}$ example described above is performed. Next, the following processing is performed as the fourth anisotropic site determination processing. In particular, the spatial compounding of the 22$^{nd}$ example described above is performed to extract an image region target for determination and the component image data sets of the part corresponding to the extracted image region are extracted. Then, with respect to the part of the extracted component image data sets, the determination the position of the anisotropic site of the spatial compounding described in the 17$^{th}$ example described above is performed. After the transmission/reception conditions are changed, ultrasound scanning is performed respectively at the scan regions having the steering angles 0°, −7.5° and −15° to obtain component image data sets and the spatial compounding is performed.

Embodiment Example 22

In embodiment example 22, aspects are the same as those of embodiment example 21 except that the reception F value is set to 0.8.

Embodiment Example 23

In embodiment example 23, the spatial compounding of the 23$^{rd}$ example described above is performed to generate synthetic image data. At this time, the following processing is performed as the third anisotropic site determination processing. That is, the determination of the position of the anisotropic site of the spatial compounding described in the 22$^{nd}$ example described above is performed. In particular, the spatial compounding of the 22$^{nd}$ example described above is performed to extract an image region target for determination and component image data sets of the part corresponding to the extracted image region are extracted. Then, with respect to the part of the extracted component image data sets, the determination of the position of the anisotropic site of the spatial compounding described in the 17$^{th}$ example described above is performed. Next, the following processing is performed as the fourth anisotropic site determination processing. That is, the spatial compounding of the 22$^{nd}$ example described above is performed to extract an image region target for determination and the component image data sets of the part corresponding to the extracted image region are extracted. Then, with respect to the part of the extracted component image data sets, the determination of the position of the anisotropic site of the spatial compounding described in the 20$^{th}$ example described above is performed. After the transmission/reception conditions are changed, ultrasound scanning is respectively performed in the scan regions having steering angles 0°, +10°, −10° and −15° to obtain component image data sets and the spatial compounding is performed.

Embodiment Example 24

In embodiment example 24, aspects are similar to those in embodiment example 16 except that when performing the spatial compounding, the component image data set corresponding to the scan region having the steering angle 0° is weighted by 40%, the component image data set corresponding to the scan region having the steering angle −20° is weighted by 20% and the component image data set corresponding to the scan region having the steering angle −10° is weighted by 40%.

Embodiment Example 25

In embodiment example 25, aspects are similar to those in embodiment example 24 except for that the reception F value is set to 0.8.

TABLE 1

| | determination parameter | | | | | | | | | | image synthesis condition | | | | visibility of anterior talofibular ligament | | |
|---|---|---|---|---|---|---|---|---|---|---|---|---|---|---|---|---|---|
| | select | | sound ray information | | | image information | | | | | | synthesis weighting rate | | | anterior talofibular ligament | | other than anterior talofibular ligament |
| | receiving aperture receive F value | termination region (luminescence difference) | coherence factors | frequency analysis | waveform pattern detection | luminescence difference b/w images | spatial frequency analysis | image pattern detection | edge detection | correlation operation b/w images | division synthesis of region | image (1) rate | image (2) rate | image (3) rate | image luminous score (1-10) | visibility score (1-10) | ligament visibility score (1-10) |
| Comparison example 1 | 1.5 | — | — | — | — | — | — | — | — | — | NO | 100.0% | — | — | 2 | | 3 |
| Comparison example 2 | 1.5 | — | — | — | — | — | — | — | — | — | NO | 33.3% | 33.3% | 33.3% | 4 | | 7 |
| Embodiment example 1 | 1.5 | — | ○ | — | — | — | — | — | — | — | NO | 40% | 20% | 40% | 6 | 6 | 7 |
| Embodiment example 2 | 1.5 | — | — | ○ | — | — | — | — | — | — | NO | 40% | 20% | 40% | 6 | 6 | 7 |
| Embodiment example 3 | 1.5 | — | — | — | ○ | — | — | — | — | — | NO | 40% | 20% | 40% | 6 | 6 | 7 |
| Embodiment example 4 | 1.5 | — | — | — | — | ○ | — | — | — | — | NO | 40% | 20% | 40% | 6 | 6 | 7 |
| Embodiment example 5 | 1.5 | — | — | — | — | — | ○ | — | — | — | NO | 40% | 20% | 40% | 6 | 6 | 7 |
| Embodiment example 6 | 1.5 | — | — | — | — | — | — | ○ | — | — | NO | 40% | 20% | 40% | 6 | 6 | 7 |
| Embodiment example 7 | 1.5 | — | — | — | — | — | — | — | ○ | — | NO | 40% | 20% | 40% | 6 | 6 | 7 |
| Embodiment example 8 | 1.5 | — | — | — | — | — | — | — | — | ○ | NO | 40% | 20% | 40% | 6 | 6 | 7 |
| Embodiment example 9 | 1.5 | ○ | — | — | — | — | — | ○ | — | — | NO | 40% | 20% | 40% | 6 | 6 | 7 |
| Embodiment example 10 | 1.5 | — | — | — | — | ○ | — | — | ○ | — | NO | 50% | 10% | 40% | 7 | 8 | 6 |
| Embodiment example 11 | 1.5 | — | — | — | — | ○ | — | — | — | — | YES | 40% | 20% | 40% | 8 | 7 | 7 |
| Embodiment example 12 | 0.8 | — | — | — | — | ○ | — | — | — | — | NO | 40% | 20% | 40% | 7 | 7 | 8 |

TABLE 2

| | the number of direction of transmittion and reception | | transmission/reception condition | | | | | | | | receive aperture receive F value | determination parameter | | | |
|---|---|---|---|---|---|---|---|---|---|---|---|---|---|---|---|
| | | | transmission and reception angle | | | | | | | | | select termination region (luminescence difference) | sound ray information | | |
| | | | (1) | | (2) | | (3) | | (4) | | | | coherence factors | frequency analysis | waveform pattern detection |
| | initial | after applied | initial | after applied | initial | after applied | initial | after applied | initial | after applied | | | | | |
| Comparison example 1 | 1 | — | ±0° | — | — | — | — | — | — | — | 1.5 | — | — | — | — |
| Comparison example 2 | 3 | — | ±0° | — | +10° | — | −10° | — | — | — | 1.5 | — | — | — | — |
| Embodiment example 13 | 3 | 3 | ±0° | ±0° | +10° | −20° | −10° | −10° | — | — | 1.5 | — | ○ | — | — |
| Embodiment example 14 | 3 | 3 | ±0° | ±0° | +10° | −20° | −10° | −10° | — | — | 1.5 | — | — | ○ | — |
| Embodiment example 15 | 3 | 3 | ±0° | ±0° | +10° | −20° | −10° | −10° | — | — | 1.5 | — | — | — | ○ |
| Embodiment example 16 | 3 | 3 | ±0° | ±0° | +10° | −20° | −10° | −10° | — | — | 1.5 | — | — | — | — |
| Embodiment example 17 | 3 | 3 | ±0° | ±0° | +10° | −20° | −10° | −10° | — | — | 1.5 | — | — | — | — |
| Embodiment example 18 | 3 | 3 | ±0° | ±0° | +10° | −20° | −10° | −10° | — | — | 1.5 | — | — | — | — |
| Embodiment example 19 | 3 | 3 | ±0° | ±0° | +10° | −20° | −10° | −10° | — | — | 1.5 | — | — | — | — |
| Embodiment example 20 | 3 | 3 | ±0° | ±0° | +10° | −20° | −10° | −10° | — | — | 1.5 | — | — | — | — |
| Embodiment example 21 | 3 | 3 | ±0° | ±0° | +10° | −7.5° | −10° | −15° | — | — | 1.5 | ○ | — | ○ | — |
| Embodiment example 22 | 3 | 3 | ±0° | ±0° | +10° | −7.5° | −10° | −15° | — | — | 0.8 | ○ | — | ○ | — |
| Embodiment example 23 | 3 | 4 | ±0° | ±0° | +10° | +10° | −10° | −10° | — | −15° | 1.5 | ○ | — | — | — |
| Embodiment example 24 | 3 | 3 | ±0° | ±0° | +10° | −20° | −10° | −10° | — | — | 1.5 | — | — | — | — |
| Embodiment example 25 | 3 | 3 | ±0° | ±0° | +10° | −20° | −10° | −10° | — | — | 0.8 | — | — | — | — |

| | determination parameter image information | | | | | synthesis weighting rate | | | | visibility of anterior talofibular ligament | | |
|---|---|---|---|---|---|---|---|---|---|---|---|---|
| | luminescence difference b/w images | spatial frequency analysis | image pattern detection | edge detection | correlation operation b/w images | image (1) rate | image (2) rate | image (3) rate | image (4) rate | interior talofibular ligamen | | other than anterior talofibular visibility score (1-10) |
| | | | | | | | | | | image luminous score (1-10) | visibility score (1-10) | |
| Comparison example 1 | — | — | — | — | — | 100.0% | — | — | — | 2 | | 3 |
| Comparison example 2 | — | — | — | — | — | 33.3% | 33.3% | 33.3% | — | 4 | | 7 |
| Embodiment example 13 | — | — | — | — | — | 33.3% | 33.3% | 33.3% | — | 7 | 6 | 6 |
| Embodiment example 14 | — | — | — | — | — | 33.3% | 33.3% | 33.3% | — | 7 | 6 | 6 |
| Embodiment example 15 | — | — | — | — | — | 33.3% | 33.3% | 33.3% | — | 7 | 6 | 6 |
| Embodiment example 16 | ○ | — | — | — | — | 33.3% | 33.3% | 33.3% | — | 7 | 6 | 6 |
| Embodiment example 17 | — | ○ | — | — | — | 33.3% | 33.3% | 33.3% | — | 7 | 6 | 6 |
| Embodiment example 18 | — | — | ○ | — | — | 33.3% | 33.3% | 33.3% | — | 7 | 6 | 6 |
| Embodiment example 19 | — | — | — | ○ | — | 33.3% | 33.3% | 33.3% | — | 7 | 6 | 6 |
| Embodiment example 20 | — | — | — | — | ○ | 33.3% | 33.3% | 33.3% | — | 7 | 6 | 6 |
| Embodiment example 21 | ○ | — | — | — | — | 33.3% | 33.3% | 33.3% | — | 6 | 6 | 7 |

TABLE 2-continued

| | | | | | | | | | | | | |
|---|---|---|---|---|---|---|---|---|---|---|---|---|
| Embodiment example 22 | ○ | — | — | — | — | 33.3% | 33.3% | 33.3% | — | 7 | 7 | 8 |
| Embodiment example 23 | ○ | — | — | ○ | — | 25% | 25% | 25% | 25% | 7 | 7 | 7 |
| Embodiment example 24 | ○ | — | — | — | — | 40% | 20% | 40% | — | 8 | 7 | 6 |
| Embodiment example 25 | ○ | — | — | — | — | 40% | 20% | 40% | — | 8 | 7 | 7 |

As it is clear from the results shown in Tables 1 and 2, all of embodiment examples 1 to 25 clearly show the anterior talofibular ligament comparing to comparison examples 1 and 2. Further, it was found that, by performing the spatial compounding, the region other than the anterior talofibular ligament is also visualized clearly.

The entire disclosure of Japanese Patent Application No. 2012-178125 filed on Aug. 10, 2012 is incorporated herein by reference in its entirety.

What is claimed is:

1. An ultrasound diagnostic imaging apparatus comprising:
    an ultrasound probe which has a plurality of transducers, and which:
        (i) obtains receive signals by driving the plurality of transducers and performing transmission and reception of ultrasound waves to and from a subject, and
        (ii) performs ultrasound scanning a plurality of times so that a part of or all of scan regions overlap by driving the plurality of transducers and performing the transmission and reception of the ultrasound waves in a plurality of directions, the directions being different from each other; and
    a CPU which:
        (i) generates a plurality of first ultrasound image data sets according to the receive signals obtained as a result of the ultrasound probe performing the ultrasound scanning,
        (ii) evaluates an anisotropic aspect of ultrasound wave reflection in the subject according to at least either of the first ultrasound image data sets and the receive signals,
        (iii) sets a condition including at least one of (a) a transmission condition for performing the transmission of the ultrasound waves and (b) a reception condition for performing the reception of the ultrasound waves, according to the evaluation result of the anisotropic aspect, and controls the ultrasound probe to newly perform the ultrasound scanning under the set condition, and
        (iv) generates synthetic image data in which a plurality of second ultrasound image data sets, which are generated from second receive signals obtained as a result of performing the ultrasound scanning under the set condition, are synthesized.

2. The ultrasound diagnostic imaging apparatus of claim 1, wherein the CPU synthesizes the plurality of second ultrasound image data sets by a synthesis method according to the evaluation result of the anisotropic aspect.

3. The ultrasound diagnostic imaging apparatus of claim 2, wherein:
    the CPU detects an anisotropic site showing the anisotropic aspect of ultrasound wave reflection; and
    the CPU applies different synthesis methods for a part where the anisotropic site is detected and a part other than the part where the anisotropic site is detected when generating the synthetic image data.

4. The ultrasound diagnostic imaging apparatus of claim 2, wherein a depth rate of a receive focal point with respect to an aperture formed of the transducers of the second receive signals which are to be used for performing phasing addition is set to 0.8 or smaller.

5. The ultrasound diagnostic imaging apparatus of claim 2, wherein if a depth rate of a receive focal point with respect to an aperture formed of the transducers of the second receive signals which are to be used for performing phasing addition is set to a receive F value and a depth rate of a transmission focal point with respect to an aperture formed of the transducers for transmitting the ultrasound waves is set to a transmission F value, a rate of the transmission F value with respect to the receive F value is set to 3 or greater.

6. The ultrasound diagnostic imaging apparatus of claim 1, wherein the CPU sets a direction in which the transmission and reception of the ultrasound waves are to be performed as the condition to be set according to the evaluation result of the anisotropic aspect.

7. The ultrasound diagnostic imaging apparatus of claim 1, wherein the CPU sets a number of scan regions in which the ultrasound scanning is to be performed as the condition to be set according to the evaluation result of the anisotropic aspect.

8. The ultrasound diagnostic imaging apparatus of claim 1, wherein the CPU sets the transducers of the second receive signals to be used for performing phase addition as the condition to be set according to the evaluation result of the anisotropic aspect.

9. The ultrasound diagnostic imaging apparatus of claim 1, wherein a depth rate of a receive focal point with respect to an aperture formed of the transducers of the second receive signals to be used for performing phasing addition is set to 0.8 or smaller after the condition is set.

10. The ultrasound diagnostic imaging apparatus of claim 1, wherein if a depth rate of a receive focal point with respect to an aperture formed of the transducers for the second receive signals which are to be used for performing phasing addition is set to a receive F value and a depth rate of a transmission focal point with respect to an aperture formed of the transducers for transmitting the ultrasound waves is set to a transmission F value, a rate of the transmission F value with respect to the receive F value is set to 3 or greater after the condition is set.

11. The ultrasound diagnostic imaging apparatus of claim 1,
    wherein the receive signals are converted into luminescence in the first ultrasound image data, and
    wherein the CPU calculates a luminescence difference at an overlapping part in the scan regions of two ultrasound image data sets among the plurality of first ultrasound image data sets and evaluates an anisotropic aspect of a part where the calculated luminescence difference is equal to a predetermined threshold or greater.

12. The ultrasound diagnostic imaging apparatus of claim 1, wherein the CPU calculates a coherence factor, which is a rate of a coherence sum with respect to an incoherence sum, based on the receive signals respectively obtained by the transducers, the receive signals being obtained by the plurality of transducers and not yet subjected to phase addition.

13. The ultrasound diagnostic imaging apparatus of claim 1, wherein the CPU performs anisotropic aspect evaluation by detecting that a specific frequency component is continuously included in the receive signals.

14. The ultrasound diagnostic imaging apparatus of claim 1, wherein the CPU performs anisotropic aspect evaluation by detecting that a predetermined waveform pattern is included in waveforms of the receive signals on which envelope detection is performed.

15. The ultrasound diagnostic imaging apparatus of claim 1,
wherein the receive signals are converted into luminescence in the first ultrasound image data, and
wherein the CPU calculates a luminescence difference at an overlapping part in the scan regions of two ultrasound image data sets among the plurality of first ultrasound image data sets and performs anisotropic aspect evaluation based on a size of the calculated luminescence difference.

16. The ultrasound diagnostic imaging apparatus of claim 1, wherein the CPU performs spatial frequency analysis with respect to the first ultrasound image data sets and performs anisotropic aspect evaluation based on results of the spatial frequency analysis.

17. The ultrasound diagnostic imaging apparatus of claim 1, wherein the CPU performs anisotropic aspect evaluation by detecting that a predetermined anisotropic site image pattern is included in the first ultrasound image data sets.

18. The ultrasound diagnostic imaging apparatus of claim 1, wherein the CPU performs edge detection with respect to the first ultrasound image data sets and performs anisotropic aspect evaluation based on a fact that an edge of a predetermined length are extracted continuously as a result of the edge detection.

19. The ultrasound diagnostic imaging apparatus of claim 1, wherein the CPU calculates a correlation coefficient of two ultrasound image data sets among the plurality of first ultrasound image data sets by a predetermined correlation operation and performs anisotropic aspect evaluation based on the calculated correlation coefficient.

20. The ultrasound diagnostic imaging apparatus of claim 1, wherein:
the CPU executes a plurality of types of evaluation methods for anisotropic aspect evaluation, and
the CPU generates the synthetic image data according to an anisotropic aspect evaluation result on condition that the anisotropic aspect evaluation is performed by applying at least a predetermined number of types of evaluation methods among the plurality of types of evaluation methods.

* * * * *